United States Patent
Phares et al.

(10) Patent No.: US 9,878,972 B2
(45) Date of Patent: *Jan. 30, 2018

(54) COMPOUNDS AND METHODS FOR DELIVERY OF PROSTACYCLIN ANALOGS

(71) Applicant: United Therapeutics Corporation, Silver Spring, MD (US)

(72) Inventors: Ken Phares, Chapel Hill, NC (US); David Mottola, Cary, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,014

(22) Filed: Aug. 17, 2016

(65) Prior Publication Data

US 2016/0355455 A1 Dec. 8, 2016

Related U.S. Application Data

(60) Continuation of application No. 14/881,379, filed on Oct. 13, 2015, now Pat. No. 9,422,223, which is a division of application No. 14/710,694, filed on May 13, 2015, now Pat. No. 9,278,901, which is a continuation of application No. 14/490,014, filed on Sep. 18, 2014, now Pat. No. 9,199,908, which is a continuation of application No. 13/906,585, filed on May 31, 2013, now Pat. No. 9,050,311, which is a division of application No. 13/558,757, filed on Jul. 26, 2012, now Pat. No. 8,536,363, which is a continuation of application No. 12/078,955, filed on Apr. 8, 2008, now Pat. No. 8,252,839, which is a division of application No. 11/603,124, filed on Nov. 22, 2006, now Pat. No. 7,384,978, which is a continuation of application No. 10/851,481, filed on May 24, 2004, now Pat. No. 7,417,070.

(60) Provisional application No. 60/472,407, filed on May 22, 2003.

(51) Int. Cl.

| | |
|---|---|
| C07C 59/13 | (2006.01) |
| C07C 69/716 | (2006.01) |
| A61K 9/00 | (2006.01) |
| A61K 31/216 | (2006.01) |
| C07C 59/70 | (2006.01) |
| C07C 69/712 | (2006.01) |
| C07C 229/08 | (2006.01) |
| C07C 235/06 | (2006.01) |
| C07C 235/08 | (2006.01) |
| C07C 259/06 | (2006.01) |
| C07F 9/09 | (2006.01) |
| C07F 9/117 | (2006.01) |
| C07C 51/41 | (2006.01) |
| A61K 31/235 | (2006.01) |
| A61K 31/192 | (2006.01) |
| A61K 31/223 | (2006.01) |

(52) U.S. Cl.
CPC ............ *C07C 59/13* (2013.01); *A61K 9/0019* (2013.01); *A61K 9/0053* (2013.01); *A61K 31/192* (2013.01); *A61K 31/216* (2013.01); *A61K 31/223* (2013.01); *A61K 31/235* (2013.01); *C07C 51/412* (2013.01); *C07C 59/70* (2013.01); *C07C 69/712* (2013.01); *C07C 229/08* (2013.01); *C07C 235/06* (2013.01); *C07C 235/08* (2013.01); *C07C 259/06* (2013.01); *C07F 9/091* (2013.01); *C07F 9/117* (2013.01); *C07C 2103/10* (2013.01); *C07C 2603/10* (2017.05)

(58) Field of Classification Search
None
See application file for complete search history.

(56) References Cited

U.S. PATENT DOCUMENTS

| | | | |
|---|---|---|---|
| 4,306,075 | A | 12/1981 | Aristoff |
| 4,306,076 | A | 12/1981 | Nelson |
| 4,338,457 | A | 7/1982 | Aristoff |
| 4,349,689 | A | 9/1982 | Aristoff |
| 4,420,632 | A | 12/1983 | Aristoff |
| 4,434,164 | A | 2/1984 | Lombardino |
| 4,486,598 | A | 12/1984 | Aristoff |
| 4,490,537 | A | 12/1984 | Johnson |
| 4,499,085 | A | 2/1985 | Masuda |
| 4,525,586 | A | 6/1985 | Aristoff |
| 4,544,764 | A | 10/1985 | Aristoff |
| 4,668,814 | A | 5/1987 | Aristoff |
| 4,683,330 | A | 7/1987 | Aristoff |
| 5,028,628 | A | 7/1991 | Tadepalli et al. |

(Continued)

FOREIGN PATENT DOCUMENTS

| | | |
|---|---|---|
| EP | 0 159 784 | 10/1985 |
| EP | 0947196 A1 | 10/1999 |

(Continued)

OTHER PUBLICATIONS

U.S. Appl. No. 60/472,407, filed May 22, 2003, Phares et al.

(Continued)

*Primary Examiner* — Kortney L Klinkel
*Assistant Examiner* — Tori M Strong
(74) *Attorney, Agent, or Firm* — Foley & Lardner LLP

(57) ABSTRACT

This invention pertains generally to prostacyclin formulations and methods for their use in promoting vasodilation, inhibiting platelet aggregation and thrombus formation, stimulating thrombolysis, inhibiting cell proliferation (including vascular remodeling), providing cytoprotection, preventing atherogenesis and inducing angiogenesis.

34 Claims, 25 Drawing Sheets

(56) References Cited

U.S. PATENT DOCUMENTS

| | | |
|---|---|---|
| 5,049,582 A | 9/1991 | Adler et al. |
| 5,153,222 A | 10/1992 | Tadepalli et al. |
| 5,190,972 A | 3/1993 | Dumble |
| 5,234,953 A | 8/1993 | Crow et al. |
| 5,321,043 A | 6/1994 | Dumble |
| 5,466,713 A | 11/1995 | Blitstein-Willinger et al. |
| 5,496,850 A | 3/1996 | Mutoh et al. |
| 5,506,265 A | 4/1996 | Blitstein-Willinger |
| 5,545,671 A | 8/1996 | Schneider et al. |
| 5,663,203 A | 9/1997 | Ekerdt et al. |
| 5,814,301 A | 9/1998 | Klopp et al. |
| 6,054,486 A | 4/2000 | Crow et al. |
| 6,171,786 B1 | 1/2001 | Shtil et al. |
| 6,242,482 B1 | 6/2001 | Shorr et al. |
| 6,441,245 B1 | 8/2002 | Moriarty et al. |
| 6,451,815 B1 | 9/2002 | Hwang et al. |
| 6,469,022 B1 | 10/2002 | Schellens |
| 6,521,212 B1 | 2/2003 | Cloutier et al. |
| 6,528,688 B2 | 3/2003 | Moriarty et al. |
| 6,700,025 B2 | 3/2004 | Moriarty et al. |
| 6,706,283 B1 | 3/2004 | Appel et al. |
| 6,765,117 B2 | 7/2004 | Moriarty et al. |
| 6,809,223 B2 | 10/2004 | Moriarty et al. |
| 7,132,453 B2 | 11/2006 | Peebles, Jr. et al. |
| 7,384,978 B2 | 6/2008 | Phares et al. |
| 7,417,070 B2 | 8/2008 | Phares et al. |
| 7,544,713 B2 | 6/2009 | Phares et al. |
| 8,232,316 B2 | 7/2012 | Phares et al. |
| 8,252,839 B2 | 8/2012 | Phares et al. |
| 8,350,079 B2 | 1/2013 | Walsh |
| 8,481,782 B2 | 7/2013 | Batra et al. |
| 8,497,393 B2 | 7/2013 | Batra et al. |
| 8,536,363 B2 | 9/2013 | Phares et al. |
| 9,050,311 B2 | 6/2015 | Phares et al. |
| 2001/0038855 A1 | 11/2001 | Desjardin et al. |
| 2001/0056095 A1 | 12/2001 | Mylari |
| 2002/0090388 A1 | 7/2002 | Humes et al. |
| 2003/0053958 A1 | 3/2003 | Cloutier et al. |
| 2003/0108512 A1* | 6/2003 | Shorr .................. A61K 31/557 424/78.24 |
| 2003/0216474 A1 | 11/2003 | Peebles, Jr. et al. |
| 2005/0085540 A1 | 4/2005 | Phares et al. |
| 2005/0101608 A1 | 5/2005 | Santel |
| 2005/0254032 A1 | 11/2005 | Ozaki et al. |
| 2005/0282901 A1 | 12/2005 | Phares et al. |
| 2007/0078095 A1 | 4/2007 | Phares et al. |
| 2007/0078182 A1 | 4/2007 | Phares et al. |
| 2007/0082948 A1 | 4/2007 | Phares et al. |
| 2015/0005374 A1 | 1/2015 | Phares et al. |

FOREIGN PATENT DOCUMENTS

| | | |
|---|---|---|
| GB | 2 070 596 A | 9/1981 |
| WO | WO 98/18452 A1 | 5/1998 |
| WO | WO 99/21830 A1 | 5/1999 |
| WO | WO 99/25357 | 5/1999 |
| WO | WO 00/055314 A3 | 9/2000 |
| WO | WO 00/57701 A1 | 10/2000 |
| WO | WO 2002/053517 A2 | 7/2002 |
| WO | WO 03/049676 A2 | 6/2003 |
| WO | WO 03/070163 A2 | 8/2003 |
| WO | WO 2005/007081 A | 1/2005 |
| WO | WO 2005/058303 A | 6/2005 |

OTHER PUBLICATIONS

Badesch et al., "Prostanoid Therapy for Pulmonary Arterial Hypertension," Journal of the American College of Cardiology, 2004, 43(12:SupplS):56S-61S.
Bayés et al., "Gateways to Clinical Trials," Methods Find Exp. Clin. Pharmacol., Sep. 2003, 25(7):565-597.
Belch et al., "Randomized, Double-Blind, Placebo-Controlled Study Evaluating the Efficacy and Safety of AS-013, a Prostaglandin $E_1$ Prodrug, in Patients With Intermittent Claudication," Circulation, The American Heart Association, Inc., vol. 95, No. 9, May 1997, pp. 2298-2301.
Berge et al., "Pharmaceutical Salts," Journal of Pharmaceutical Sciences, Jan. 1977, 66(1):1-20.
Braun-Moscovici et al., "Endothelin and Pulmonary Arterial Hypertension," Seminars in Arthritis and Rheumatism, Aug. 2004, 34(1):442-453.
Dumble et al., "15 AU81, A Prostacyclin Analog, Potentiates Immunosuppression and Mitigates Renal Injury Due to Cyclosporine," Transplantation, May 1, 1993, 55(5):1124-1128.
Eells et al., "Advances in Prostacyclin Therapy for Pulmonary Arterial Hypertension," Critical Care Nurse, Apr. 2004, 24(2):42-48, 50-54.
Galiè et al., "Emerging Medical Therapies for Pulmonary Arterial Hypertension," Progress in Cardiovascular Diseases, Nov./Dec. 2002, 45(3):213-224.
Galiè et al., "Medical Therapy of Pulmonary Hypertension," Clinics in Chest Medicine, Sep. 2001, 22(3):529-537.
Galiè et al., "Prostanoids for Pulmonary Arterial Hypertension," Am. J. Respir. Med., 2003, 2(2):123-137.
Galiè et al., "The new clinical trials on pharmacological treatment in pulmonary arterial hypertension" Eur. Respir. J., 2002, 20:1037-1049.
Gould et al., "Salt selection for basic drugs," International Journal of Pharmaceutics, 1986, 33:201-217.
Hassner et al., "Direct Room Temperature Esterification of Carboxylic Acids" Tetrahedron Letters, Perganon Press Ltd., vol. 46, 1978, pp. 4475-4478.
Hoeper, M.M., "Pulmonary hypertension in collagen vascular disease," Eur. Respir. J., 2002, 19:571-576.
Horn et al., "Treprostinil therapy for pulmonary artery hypertension," Expert Opin. Investig. Drugs, 2002, 11(11):1615-1622.
Huffman et al., "Pulmonary Arterial Hypertension: New Management Options," Curr. Treat. Options Cardiovasc. Med., Dec. 2004, 6(6):451-458.
Hussar, Daniel A., "New Drugs 2003, Part II," Nursing, Jul. 2003, 33(7):57-64.
Keith et al., "Manipulation of Pulmonary Prostacyclin Synthase Expression Prevents Murine Lung Cancer," Cancer Research, Feb. 1, 2002, 62:734-740.
Lee et al., "Efficient In Situ Esterification of Carboxylic Acids Using Cesium Carbonate," Organic Preparations and Procedures International, vol. 28, No. 4, Aug. 1996, pp. 480-483.
Maloney, James P., M.D., "Advances in the treatment of secondary pulmonary hypertension," Curr. Opin. Pulm. Med., Mar. 2003, 9(2):139-143.
Mann et al., Organic Syntheses, John Wiley & Sons, Inc., vol. 75, 1998, pp. 139-145.
McLaughlin et al., "Pulmonary Hypertension," Curr. Probl. Cardiol., Oct. 2004, 29(10):575-634.
Mohler et al., "Trial of a novel prostacyclin analog, UT-15, in patients with severe intermittent claudication," Vascular Medicine, Nov. 1, 2000, 5(4):231-237.
Mohler, "Medical Management of Claudication," Up to Date, Inc., Mar. 31, 1997, pp. 1-6.
Mohler, "Clinical Manifestations of Claudication," Up to Date, Inc., Sep. 30, 1996, pp. 1-4.
Murohara et al., "Vascular Endothelial Growth Factor/Vascular Permeability Factor Enhances Vascular Permeability Via Nitric Oxide and Prostacyclin," Circulation, Jan. 13, 1998, 97(1):99-107.
Nagaya, Noritoshi, "Drug Therapy of Primary Pulmonary Hypertension," Am. J. Cardiovasc. Drugs, 2004, 4(2):75-85.
Nielsen et al., "Evaluation of Glycolamide Esters and Various Other Esters of Aspirin as True Aspirin Prodrugs," J. Med. Chem., 1989, 32(3):727-734.
Okuda et al., "Acute Effect of Beraprost Sodium on Lower Limb Circulation in Patients with Non-Insulin-Dependent Diabetes Mellitus-Evaluation by Color Doppler Ultrasonography and Laser Cutaneous Blood Flowmetry," Prostaglandins, Elsevier, vol. 52, Nov. 1996, pp. 375-384.

(56) References Cited

OTHER PUBLICATIONS

Paramothayan et al., "Prostacyclin for pulmonary hypertension in adults (Review)," Cochrane Database Syst. Rev., 2003, 2:CD002994, 1-80.

Pass et al., "Current and Emerging Therapy for Primary Pulmonary Hypertension," The Annals of Pharmacotherapy, Sep. 2002, 36:1414-1423.

Patterson et al., "Acute Hemodynamic Effects of the Prostacyclin Analog 15AU81 in Service Congestive Heart Failure," The American Journal of Cardiology, vol. 75, Jan. 19, 1995, pp. 26A-33A.

Phares et al., "Stabilith and preservative effectiveness of treprostinil sodium after dilution in common intravenous diluents," Am. J. Health-Syst. Pharm., May 1, 2003, 60:916-922.

Remodulin® Product Information brochure, United Therapeutics Corporation, approved by FDA for marketing on May 21, 2002, 13 pages.

Schermuly et al., "Subthreshold Doses of Specific Phosphodiesterase Type 3 and 4 Inhibitors Enhance the Pulmonary Vasodilatory Response to Nebulized Prostacyclin with Improvement in Gas Exchange," The Journal of Pharmacology and Experimental Therapeutics, 2000, 292(2):512-520.

Simonneau et al., "Continuous Subcutaneous Infusion of Treprostinil, a Prostacyclin Analogue, in Patients with Pulmonary Arterial Hypertension," Am. J. Respir. Crit. Care Med., 2002, 165:800-804.

Stahl et al., Eds., Handbook of Pharmaceutical Salts, 2002, 214-216, 314, 315 and 322.

Suleman et al., "Transition from Epoprostenol and Treprostinil to the Oral Endothelin Receptor Antagonist Bosentan in Patients with Pulmonary Hypertension," Chest, Sep. 2004, 126(3):808-815.

Sulica et al,. "Current Medical Treatment of Pulmonary Arterial Hypertension," Mount Sinai Journal of medicine, Mar. 2004, 71(2):103-114.

U.S. Food and Drug Administration Website entry regarding Diethanolamine, Dec. 21, 1999, updated Oct. 27, 2006, 1 page.

Vemuri et al., "Preparation and characterization of liposomes as therapeutic delivery systems: a review," Pharmaceutical Acta Helvetiae, Jul. 1, 1995, 70(2):95-111.

Wade et al., "Effect of Continuous Subcutaneous Treprostinil Therapy on the Pharmacodynamics and Pharmacokinetics of Warfarin," J. Cardiovasc. Pharmacol., Jun. 2003, 41(6):908-915.

Zamudio, Tomas Pulido, "Que es lo nuevo en el tratamiento de la hipertension arterial pulmonar?" Archivos de Cardiologia de Mexico, Apr.-Jun. 2003, 73(Supp1):S121-S124.

Channick et al., "New and Experimental Therapies for Pulmonary Hypertension," Clinics in Chest Medicine, Sep. 2001, 22(3):539-545.

Findlay et al., "Radioimmunoassay for the Chemical Stable Prostacyclin Analog, 15AU81: a Preliminary Pharmacokinetics Study in the Dog," Prostaglandins Leukotrienes and Essential Fatty Acids, Feb. 1993, 48(2):167-174.

Fink et al., "Use of Prostacyclin and its Analogues in the Treatment of Cardiovascular Disease," Heart Disease, 1999, 1:29-40.

Hoeper et al., "New Treatments for Pulmonary Arterial Hypertension," Am. J. Repir. Crit. Care Med., 2002, 165:1209-1216.

McLaughlin et al., "Efficacy and Safety of Treprostinil: An Epoprostenol Analog for Primary Pulmonary Hypertension," Journal of Cardiovascular Pharmacology, 2003, 41:293-299.

McNulty et al., "The Pharmacokinetics and Pharmacodynamics of the Prostacyclin Analog 15AU81 in the Anesthetized Beagle Dog," Prostaglandins Leukot. Essent. Fatty Acids, Feb. 1993, 48(2):159-166.

Shitrit et al., "Elevation of ELISA D-Dimer Levels in Patients with Primary Pulmonary Hypertension," Respiration, 2002, 69:327-329.

Steffen et al., "The Effects of 15AU81, a Chemically Stable Prostacyclin Analog, on the Cardiovascular and Renin-Angiotensis Systems of Anesthetized Dogs," Prostaglandins Leukotrienes and Essential Fatty Acids, 1991, 43:277-286.

Defendant Actavis Laboratories FL, Inc. Preliminary Invalidity Contentions, dated Aug. 30, 2016, *United Therapeutics Corporation, and Supernus Pharmaceuticals, Inc.*, (Plaintiff) v. *Actavis Laboratories FL, Inc.*, (Defendant), In The United States District Court for the Distritc of New Jersey, Civil Action No. 3:16-cv-01816-PGS-LHG, Civil Action No. 3:16-cv-03642-PGS-LHG, 330 pages, (see particularly pp. 20-35, 39-41, 62-203 and Exhibits B, C, D, E, F and I).

Alberts et al., Ed., Molecular Biology of the Cell, $3^{rd}$ Ed., 1994, 478-480.

Allen et al., Eds., Ansel's Pharmaceutical Dosage Forms and Drug Delivery Systems, 2005, $8^{th}$ Ed., 152-162; 262.

Ansel et al., Eds., Pharmaceutical Dosage Forms and Drug Delivery Systems, 1999, $7^{th}$ Ed., 102-106; 116-117; 196-203 tablets; 548.

Beghetti et al,. "Aerosolized iloprost induces a mild but sustained inhibition of platelet aggregation," Eur. Respir. J., 2002, 19:518-524.

Bighley et al., "Salt Forms of Drugs and Absorption," Encyclopedia of Pharmaceutical Technology, Swarbrick et al., Eds., 1995, 13:453-499.

Byrn et al. "Pharmaceutical Solids: A Strategic Approach to Regulatory Considerations" Pharmaceutical Research, 1995, 12(7):945-954.

Caira, M. R., "Crystalline Polymorphism of Organic Compounds," Design of Organic Solids, 1998, E. Weber Ed., Springer, New York, 163-208.

Center for Drug Evaluation and Research, NDA 203496—Treprostinil diethanolamine, Clinical Pharmacology and Biopharmaceutics Reviews, 2012, 96 pages.

Chattaraj et al., "Treprostinil sodium Pharmacia," Current Opinion in Investigational Drugs, 2002, 3(4):582-586.

Desiraju, Gautam R., "Crystal Gazing: Structure Prediction and Polymorphism," Science, Oct. 17, 1997, 278:404-405.

Diethanolamine, U.S. Food and Drug Administration Protecting and Promoting Your Health, 1999, 2 pages.

Fischer, Andrew, "United Therapeutics Receives FDA Approvable Letter for Remodulin to Treat Pulmonary Arterial Hypertension," United Therapeutics Corporation Press Release, 2002, 2 pages.

Grant et al., Grant & Hackh's Chemical Dictionary, $5^{th}$ Ed., 1987, 160-161.

Gu et al., "Polymorph Screening: Influence of Solvents on the Rate of Solvent-Mediated Polymorphic Transformation," Journal of Pharmaceutical Sciences, Nov. 2001, 90(11):1878-1890.

Guideline for Submitting Supporting Documentation in Drug Applications for the Manufacture of Drug Substances, U.S. Department of Health and Human Services Food and Drug Administration Center for Drug Evaluation and Research, Feb. 1987, 48 pages.

Guillory, J. Keith, "Generation of Polymorphs, Hydrates, Solvates, and Amorphous Solids," Polymorphism in Pharmaceutical Sciences, H. Brittain ed., 1999, 183-226.

Haleblian et al., "Pharmaceutical Applications of Polymorphism," J. Pharm. Sci., Aug. 1969, 58(8):911-929.

Haleblian, John K., "Characterization of Habits and Crystalline Modification of Solids 37 and Their Pharmaceutical Applications," J. Pharm. Sci., Aug. 1975, 64(8):1269-1288.

Lehman-McKeeman et al., "Diethanolamine Induces Hepatic Choline Deficiency in Mice," Toxicological Sciences, 2002, 67:38-45.

McCrone, Walter C., :Polymorphism, Physics and Chemistry of the Organic Solid State, 1965, Fox, et al., Eds., 725-767.

Olmsted III et al., Chemistry, The Molecular Science, Mosby-Year Book, Inc., Chapter 10 "Effects of Intermolecular Forces," 1994, 428-486.

Orenitram Highlights of Prescribing Information, Initial US Approval 2002, 13 pages.

Pavia et al., Introduction to Organic Laboratory Techniques, First Edition, 1998, 648.

Reepmeyer et al., "Characterization and Crystal Structure of Two Polymorphic Forms of Racemic Thalidomide," J. Chem. Soc. Perkin Trans., 1994, 2:2063-2067.

Rodriguez-Hornedo et al., "Significance of Controlling Crystallization Mechanisms and Kinetics in Pharmaceutical Systems," Journal of Pharmaceutical Sciences, Jul. 1999, 88(7):651-660.

Sharp et al., Eds., Practical Organic Chemistry: A student handbook of techniques, 1989, 64-85.

(56) References Cited

OTHER PUBLICATIONS

Shekunov et al., "Crystallization processes in pharmaceutical technology and drug delivery design," Journal of Crystal Growth, 2000, 211:122-136.
Threlfall, Terence L., "Analysis of Organic Polymorphs. A Review," Analyst, Oct. 1995, 120:2435-2460.
Tyvaso® Label, Jul. 2009, with package insert, 16 pages.
Ulrich, Anne S., "Biophysical Aspects of Using Liposomes as Delivery Vehicles," Bioscience Reports, Apr. 2002, 22(2):129-150.
Vippagunta et al., "Crystalline solids," Advanced Drug Delivery Reviews, 2001, 48:3-26.
Vizza et al., "Long term treatment of pulmonary arterial hypertension with Beraprost, an oral prostacyclin analogue," Heart, 2001, 86:661-665.
Yeo et al., "Formation of Microparticulate Protein Powders Using a Supercritical Fluid Antisolvent," Biotechnology and Bioengineering, 1993, 41:341-346.
Yu et al., "Crystallization and Polymorphism of Conformationally Flexible Molecules: Problems, Patterns, and Strategies," Organic Process Research & Development, 2000, 4:396-402.
Yu et al., "Physical Characterization of Polymorphic Drugs: An Integrated Characterization Strategy," PSTT, 1998, 1(3):118-127.

\* cited by examiner

COMPOUNDS AND METHODS FOR DELIVERY OF PROSTACYCLIN ANALOGS

CROSS-REFERENCE TO RELATED PATENT APPLICATIONS

This application is a continuation of U.S. application Ser. No. 14/881,379, filed Oct. 13, 2015, which is a divisional of U.S. application Ser. No. 14/710,694, filed May 13, 2015, which is a continuation of U.S. application Ser. No. 14/490,014, filed Sep. 18, 2014, which is a Continuation of U.S. application Ser. No. 13/906,585, filed May 31, 2013, which is a divisional of U.S. application Ser. No. 13/558,757, filed Jul. 26, 2012, which is a continuation of U.S. application Ser. No. 12/078,955, filed Apr. 8, 2008, which is a divisional of U.S. application Ser. No. 11/603,124, filed Nov. 22, 2006, which is a continuation of U.S. application Ser. No. 10/851,481, filed May 24, 2004, which claims benefit of U.S. Provisional Application Ser. No. 60/472,407, filed on May 22, 2003, the entire contents of which applications are incorporated by reference herein.

FIELD OF THE INVENTION

This invention pertains generally to prostacyclin analogs and methods for their use in promoting vasodilation, inhibiting platelet aggregation and thrombus formation, stimulating thrombolysis, inhibiting cell proliferation (including vascular remodeling), providing cytoprotection, preventing atherogenesis and inducing angiogenesis. Through these prostacyclin-mimetic mechanisms, the compounds of the present invention may be used in the treatment of/for: pulmonary hypertension, ischemic diseases (e.g., peripheral vascular disease, Raynaud's phenomenon, Scleroderma, myocardial ischemia, ischemic stroke, renal insufficiency), heart failure (including congestive heart failure), conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation and other emerging therapeutic areas where prostacyclin treatment appears to have a beneficial role. These compounds may also demonstrate additive or synergistic benefit in combination with other cardiovascular agents (e.g., calcium channel blockers, phosphodiesterase inhibitors, endothelial antagonists, antiplatelet agents).

BACKGROUND OF THE INVENTION

Many valuable pharmacologically active compounds cannot be effectively administered orally for various reasons and are generally administered via intravenous or intramuscular routes. These routes of administration generally require intervention by a physician or other health care professional, and can entail considerable discomfort as well as potential local trauma to the patient.

One example of such a compound is treprostinil, a chemically stable analog of prostacyclin. Although treprostinil sodium (Remodulin®) is approved by the Food and Drug Administration (FDA) for subcutaneous administration, treprostinil as the free acid has an absolute oral bioavailability of less than 10%. Accordingly, there is clinical interest in providing treprostinil orally.

Thus, there is a need for a safe and effective method for increasing the systemic availability of treprostinil via administration of treprostinil or treprostinil analogs.

SUMMARY OF THE INVENTION

In one embodiment, the present invention provides a compound having structure I:

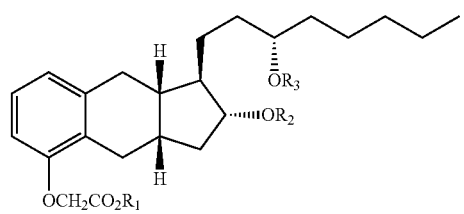

wherein, $R^1$ is independently selected from the group consisting of H, substituted and unsubstituted benzyl groups, and groups wherein $OR^1$ are substituted or unsubstituted glycolamide esters;

$R^2$ and $R^3$ may be the same or different and are independently selected from the group consisting of H, phosphate and groups wherein $OR^2$ and $OR^3$ form esters of amino acids or proteins, with the proviso that all of $R^1$, $R^2$ and $R^3$ are not H;

an enantiomer of the compound;

and pharmaceutically acceptable salts of the compound and polymorphs.

In some of these embodiments, $R^1$ is a substituted or unsubstituted benzyl group, such as $CH_2C_6H_5$. In other embodiments, $OR^1$ is a substituted or unsubstituted glycolamide ester, $R^1$ is $-CH_2CONR^4R^5$, $R^4$ and $R^5$ may be the same or different and are independently selected from the group consisting of H, OH, substituted and unsubstituted alkyl groups, $-(CH_2)_mCH_3$, $-CH_2OH$, and $-CH_2(CH_2)_n OH$, with the proviso that m is 0, 1, 2, 3 or 4, and n is 0, 1, 2, 3 or 4. In certain of these embodiments one or both of $R^4$ and $R^5$ are independently selected from the group consisting of H, $-OH$, $-CH_3$, or $-CH_2CH_2OH$. In any of the previously discussed embodiments, one or both of $R^2$ and $R^3$ can be H. In some embodiments, one or both of $R^2$ and $R^3$ can be H. In some enantiomers of the compound $R^1=R^2=R^3=H$, or $R^2=R^3=H$ and $R^1$=valinyl amide.

In still further embodiments of the present compounds $R^2$ and $R^3$ are independently selected from phosphate and groups wherein $OR^2$ and $OR^3$ are esters of amino acids, dipeptides, esters of tripeptides and esters of tetrapeptides. In some compounds only one of $R^2$ or $R^3$ is a phosphate group. In other compounds $R^2$ and $R^3$ are independently selected from groups wherein $OR^2$ and $OR^3$ are esters of amino acids, such as esters of glycine or alanine. In any of the above embodiments, one of $R^2$ and $R^3$ are H. In certain of the present compounds, the oral bioavailability of the compound is greater than the oral bioavailability of treprostinil, such as at least 50% or 100% greater than the oral bioavailability of treprostinil. The above compounds can further comprise an inhibitor of p-glycoprotein transport. Any of these compounds can also further comprise a pharmaceutically acceptable excipient.

The present invention also provides a method of using the above compounds therapeutically of/for: pulmonary hypertension, ischemic diseases, heart failure, conditions requiring anticoagulation, thrombotic microangiopathy, extracorporeal circulation, central retinal vein occlusion, atherosclerosis, inflammatory diseases, hypertension, reproduction and parturition, cancer or other conditions of unregulated cell growth, cell/tissue preservation and other emerging therapeutic areas where prostacyclin treatment appears to have a beneficial role. A preferred embodiment is a method of treating pulmonary hypertension and/or peripheral vascular disease in a subject comprising orally administering a pharmaceutically effective amount of a compound of structure II:

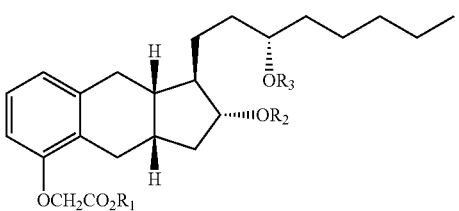

wherein, $R^1$ is independently selected from the group consisting of H, substituted and unsubstituted alkyl groups, arylalkyl groups and groups wherein $OR^1$ form a substituted or unsubstituted glycolamide ester;

$R^2$ and $R^3$ may be the same or different and are independently selected from the group consisting of H, phosphate and groups wherein $OR^2$ and $OR^3$ form esters of amino acids or proteins, with the proviso that all of $R^1$, $R^2$ and $R^3$ are not H;

an enantiomer of the compound; and a pharmaceutically acceptable salt or polymorph of the compound.

In some of these methods, when $OR^1$ forms a substituted or unsubstituted glycolamide ester, $R^1$ is —$CH_2CONR^4R^5$, wherein $R^4$ and $R^5$ may be the same or different and are independently selected from the group consisting of H, OH, substituted and unsubstituted alkyl groups, —$(CH_2)_mCH_3$, —$CH_2OH$, and —$CH_2(CH_2)_nOH$, with the proviso that m is 0, 1, 2, 3 or 4, and n is 0, 1, 2, 3 or 4. In other methods $R^1$ is a $C_1$-$C_4$ alkyl group, such as methyl, ethyl, propyl or butyl. In the disclosed methods, $R^1$ can also be a substituted or unsubstituted benzyl group. In other methods, $R^1$ can be —$CH_3$ or —$CH_2C_6H_5$. In still other methods $R^4$ and $R^5$ are the same or different and are independently selected from the group consisting of H, OH, —$CH_3$, and —$CH_2CH_2OH$. In yet other methods, one or both of $R^2$ and $R^3$ are H. Alternatively, one or both of $R^2$ and $R^3$ are not H and $R^2$ and $R^3$ are independently selected from phosphate and groups wherein $OR^2$ and $OR^3$ are esters of amino acids, dipeptides, esters of tripeptides and esters of tetrapeptides. In some methods, only one of $R^2$ or $R^3$ is a phosphate group. In additional methods, $R^2$ and $R^3$ are independently selected from groups wherein $OR^2$ and $OR^3$ are esters of amino acids, such as esters of glycine or alanine. In further methods one of $R^1$ and $R^2$ is H. In some methods, enantiomers of the compound where $R^1=R^2=R^3=H$, or $R^2=R^3=H$ and $R^1$=valinyl amide are used.

In various methods the oral bioavailability of the compound is greater than the oral bioavailability of treprostinil, such as at least 50% or 100% greater than the oral bioavailability of treprostinil. The present methods can also comprise administering pharmaceutically effective amount of a p-glycoprotein inhibitor, simultaneously, sequentially, or prior to administration of the compound of structure II. In some embodiments the p-glycoprotein inhibitor is administered orally or intravenously. The disclosed methods can be used to treat pulmonary hypertension.

The present invention also provides a method of increasing the oral bioavailability of treprostinil or pharmaceutically acceptable salt thereof, comprising administering a pharmaceutically effective amount of a p-glycoprotein inhibitor and orally administering a pharmaceutically effective amount of treprostinil to a subject. In certain of these embodiments the p-glycoprotein inhibitor is administered prior to or simultaneously with the treprostinil. The route of the p-glycoprotein inhibitor administration can vary, such as orally or intravenously. The present invention also provides a composition comprising treprostinil or a pharmaceutically acceptable salt thereof and a p-glycoprotein inhibitor.

The present compound can also be administered topically or transdermally.

Pharmaceutical formulations according to the present invention are provided which include any of the compounds described above in combination with a pharmaceutically acceptable carrier.

The compounds described above can also be used to treat cancer.

Further objects, features and advantages of the invention will be apparent from the following detailed description.

DETAILED DESCRIPTION OF THE INVENTION

Figure 1A:
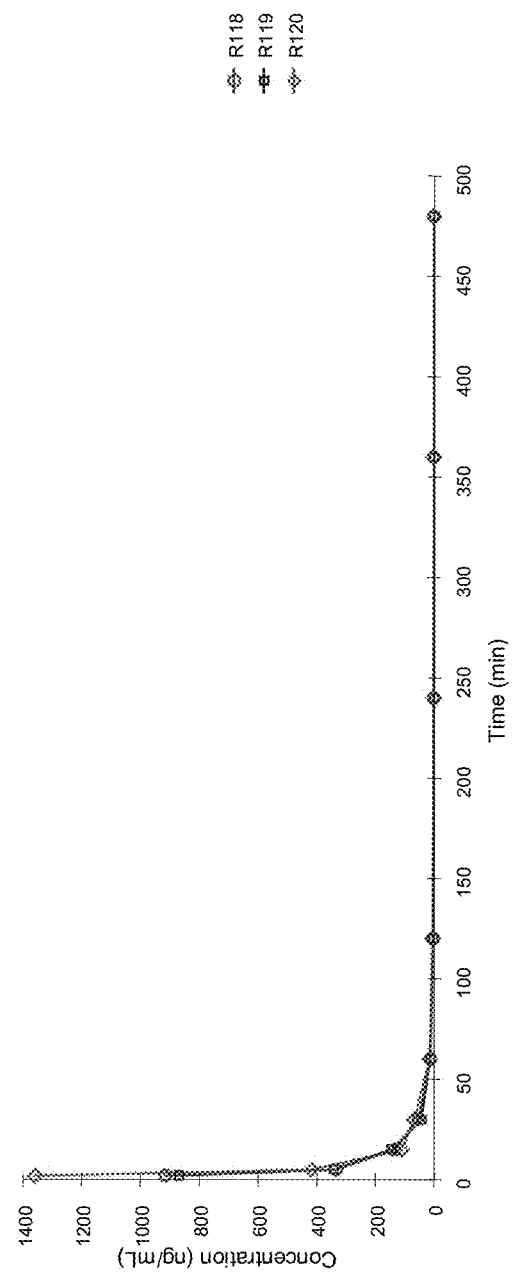
FIGS. 1A and 1B respectively show plasma concentration versus time curves for intravenous and intraportal dosing of treprostinil diethanolamine salt in rats as described in Example 1.

Unless otherwise specified, "a" or "an" means "one or more". The present invention provides compounds and methods for inducing prostacyclin-like effects in a subject or patient. The compounds provided herein can be formulated into pharmaceutical formulations and medicaments that are useful in the methods of the invention. The invention also provides for the use of the compounds in preparing medicaments and pharmaceutical formulations and for use of the compounds in treating biological conditions related to insufficient prostacyclin activity as outlined in the Field of Invention. The present invention also provides compounds and methods for the treatment of cancer and cancer related disorders.

In some embodiments, the present compounds are chemical derivatives of (+)-treprostinil, which has the following structure:

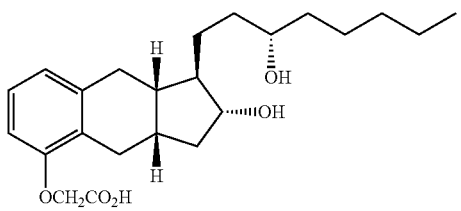

Treprostinil is a chemically stable analog of prostacyclin, and as such is a potent vasodilator and inhibitor of platelet aggregation. The sodium salt of treprostinil, (1R,2R,3aS,9aS)-[[2,3,3a,4,9,9a-Hexahydro-2-hydroxy-1-[(3S)-3-hydroxyoctyl]-1H-benz[f]inden-5-yl]oxy]acetic acid monosodium salt, is sold as a solution for injection as Remodulin® which has been approved by the Food and Drug Administration (FDA) for treatment of pulmonary hypertension. In some embodiments, the present compounds are derivatives of (−)-treprostinil, the enantiomer of (+)-treprostinil. A preferred embodiment of the present invention is the diethanolamine salt of treprostinil. The present invention further includes polymorphs of the above compounds, with two forms, A and B, being described in the examples below. Of the two forms, B is preferred. A particularly preferred embodiment of the present invention is form B of treprostinil diethanolamine.

In some embodiments, the present compounds are generally classified as prodrugs of treprostinil that convert to treprostinil after administration to a patient, such as through ingestion. In some embodiments, the prodrugs have little or no activity themselves and only show activity after being converted to treprostinil. In some embodiments, the present compounds were produced by chemically derivatizing treprostinil to make stable esters, and in some instances, the compounds were derivatized from the hydroxyl groups. Compounds of the present invention can also be provided by modifying the compounds found in U.S. Pat. Nos. 4,306,075 and 5,153,222 in like manner.

In one embodiment, the present invention provides compounds of structure I:

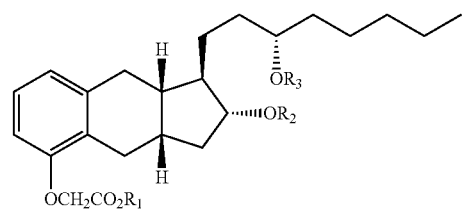

wherein, $R^1$ is independently selected from the group consisting of H, substituted and unsubstituted benzyl groups and groups wherein $OR^1$ are substituted or unsubstituted glycolamide esters;

$R^2$ and $R^3$ may be the same or different and are independently selected from the group consisting of H, phosphate and groups wherein $OR^2$ and $OR^3$ form esters of amino acids or proteins, with the proviso that all of $R^1$, $R^2$ and $R^3$ are not H;

enantiomers of the compound; and pharmaceutically acceptable salts of the compound.

In some embodiments wherein $OR^1$ are substituted or unsubstituted glycolamide esters, $R^1$ is —$CH_2CONR^4R^5$ and $R^4$ and $R^5$ may be the same or different and are independently selected from the group consisting of H, OH, substituted and unsubstituted alkyl groups, —$(CH_2)_mCH_3$, —$CH_2OH$, and —$CH_2(CH_2)_nOH$, with the proviso that m is 0, 1, 2, 3 or 4, and n is 0, 1, 2, 3 or 4.

One skilled in the art will also readily recognize that where members are grouped together in a common manner, such as in a Markush group or the groups described in the R of structures I and II above and below, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention. For example, $R^1$ can specifically exclude H, substituted and unsubstituted benzyl groups, or groups wherein $OR^1$ are substituted or unsubstituted glycolamide esters.

In some embodiments, $R^1$ is a substituted or unsubstituted benzyl groups, such as —$CH_2C_6H_5$, —$CH_2C_6H_4NO_2$, —$CH_2C_6H_4OCH_3$, —$CH_2C_6H_4Cl$, —$CH_2C_6H_4(NO_2)_2$, or —$CH_2C_6H_4F$. The benzyl group can be ortho, meta, para, ortho/para substituted and combinations thereof. Suitable substituents on the aromatic ring include halogens (fluorine, chlorine, bromine, iodine), —$NO_2$ groups, —$OR^{16}$ groups wherein $R^{16}$ is H or a $C_1$-$C_4$ alkyl group, and combinations thereof.

Alternatively, when $R^1$ is —$CH_2CONR^4R^5$ then $R^4$ and $R^5$ may be the same or different and are independently selected from the group consisting of H, OH, —$CH_3$, and —$CH_2CH_2OH$. In these compounds where $R^1$ is not H, generally one or both of $R^2$ and $R^3$ are H.

In some embodiment one or both of $R^2$ and $R^3$ are H and $R^1$ is —$CH_2CONR^4R^5$, and one or both of $R^4$ and $R^5$ are H, —OH, —$CH_3$, —$CH_2CH_2OH$.

In compounds where one or both of $R^2$ and $R^3$ are not H, $R^2$ and $R^3$ can be independently selected from phosphate and groups wherein $OR^2$ and $OR^3$ are esters of amino acids, dipeptides, esters of tripeptides and esters of tetrapeptides. In some embodiments, only one of $R^2$ or $R^3$ is a phosphate group. In compounds where at least one of $R^2$ and $R^3$ is not H, generally $R^1$ is H. In additional embodiments, one of $R^2$ and $R^3$ are H and thus the compound of structure I is derivatized at only one of $R^2$ and $R^3$. In particular compounds, $R^2$ is H and $R^3$ is defined as above. In additional embodiments, $R^1$ and $R^3$ are H and $R^2$ is a group wherein $OR^2$ is an ester of an amino acid or a dipeptide. In further embodiments, $R^1$ and $R^2$ are H and $R^3$ is a group wherein $OR^3$ is an ester of an amino acid or a dipeptide.

When one or both of the $OR^2$ and $OR^3$ groups form esters of amino acids or peptides, i.e., dipeptides, tripeptides or tetrapeptides, these can be depicted generically as —$COCHR^6NR^7R^8$ wherein $R^6$ is selected from the group consisting of amino acid side chains, $R^7$ and $R^8$ may be the same or different and are independently selected from the group consisting of H, and —$COCHR^9NR^{10}R^{11}$. Generally, reference to amino acids or peptides refers to the naturally occurring, or L-isomer, of the amino acids or peptides. However, the present compounds and methods are not limited thereto and D-isomer amino acid residues can take the place of some or all of L-amino acids. In like manner, mixtures of D- and L-isomers can also be used. In the embodiments wherein the amino acid is proline, $R^7$ together with $R^6$ forms a pyrrolidine ring structure. $R^6$ can be any of the naturally occurring amino acid side chains, for example —$CH_3$ (alanine), —$(CH_2)_3NHCNH_2NH$ (arginine), —$CH_2CONH_2$ (asparagine), —$CH_2COOH$ (aspartic acid), —$CH_2SH$ (cysteine), —$(CH_2)_2CONH_2$ (glutamine), —$(CH_2)_2COOH$ (glutamic acid), —H (glycine), —$CHCH_3CH_2CH_3$ (isoleucine), —$CH_2CH(CH_3)_2$ (leucine), —$(CH_2)_4NH_2$ (lysine), —$(CH_2)_2SCH_3$ (methionine), —$CH_2Ph$ (phenylalanine), —$CH_2OH$ (serine), —$CHOHCH_3$ (threonine), —$CH(CH_3)_2$ (valine),

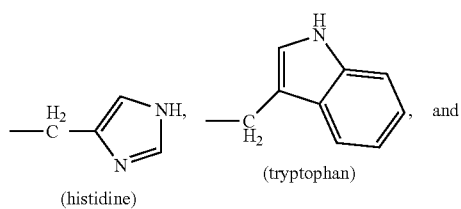
(histidine)     (tryptophan)     and

(tyrosine)

—$(CH_2)_3NHCONH_2$ (citrulline) or —$(CH_2)_3NH_2$ (ornithine). Ph designates a phenyl group.

In the above compounds, $R^7$ and $R^8$ may be the same or different and are selected from the group consisting of H, and —$COCHR^9NR^{10}R^{11}$, wherein $R^9$ is a side chain of amino acid, $R^{10}$ and $R^{11}$ may be the same or different and are selected from the group consisting of H, and —$COCHR^{12}NR^{13}R^{14}$, wherein $R^{12}$ is an amino acid side chain, $R^{13}$ and $R^{14}$ may be the same or different and are independently selected from the group consisting of H, and —$COCHR^{15}NH_2$. One skilled in the art will realize that the peptide chains can be extended on the following scheme to the desired length and include the desired amino acid residues.

In the embodiments where either or both of $OR^2$ and $OR^3$ groups form an ester of a peptide, such as dipeptide, tripeptide, tetrapeptide, etc. the peptides can be either homopeptides, i.e., repeats of the same amino acid, such as arginyl-arginine, or heteropeptides, i.e., made up of different combinations of amino acids. Examples of heterodipeptides include alanyl-glutamine, glycyl-glutamine, lysyl-arginine, etc.

As will be understood by the skilled artisan when only one $R^7$ and $R^8$ includes a peptide bond to further amino acid, such as in the di, tri and tetrapeptides, the resulting peptide chain will be linear. When both $R^7$ and $R^8$ include a peptide bond, then the peptide can be branched.

In still other embodiments of the present compounds $R^1$ is H and one of $R^2$ or $R^3$ is a phosphate group or H while the other $R^2$ or $R^3$ is a group such the $OR^2$ or $OR^3$ is an ester of an amino acid, such as an ester of glycine or alanine.

Pharmaceutically acceptable salts of these compounds as well as pharmaceutical formulation of these compounds are also provided.

Generally, the compounds described herein have enhanced oral bioavailability compared to the oral bioavailability of treprostinil, either in free acid or salt form. The described compounds can have oral bioavailability that is at least 25%, 50% 100%, 200%, 400% or more compared to the oral bioavailability of treprostinil. The absolute oral bioavailability of these compounds can range between 10%, 15%, 20%, 25%, 30% and 40%, 45%, 50%, 55%, 60% or more when administered orally. For comparison, the absolute oral bioavailability of treprostinil is on the order of 10%, although treprostinil sodium has an absolute bioavailability approximating 100% when administered by subcutaneous infusion.

As will be understood by one skilled in the art, for any and all purposes, particularly in terms of providing a written description, all ranges disclosed herein, and in particular the bioavailability ranges described herein also encompass any and all possible subranges and combinations of subranges thereof. As only one example, a range of 20% to 40%, can be broken down into ranges of 20% to 32.5% and 32.5% to 40%, 20% to 27.5% and 27.5% to 40%, etc. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

Administration of these compounds can be by any route by which the compound will be bioavailable in effective amounts including oral and parenteral routes. The compounds can be administered intravenously, topically, subcutaneously, intranasally, rectally, intramuscularly, transdermally or by other parenteral routes. When administered orally, the compounds can be administered in any convenient dosage form including, for example, capsule, tablet, liquid, suspension, and the like.

Testing has shown that that treprostinil can be irritating upon skin contact. In contrast, some of the compounds disclosed herein, generally as prodrugs of treprostinil, are not irritating to the skin. Accordingly, the present compounds are well suited for topical or transdermal administration.

When administered to a subject, the above compounds, and in particular the compounds of structure I, are prostacyclin-mimetic and are useful in treating conditions or disorders where vasodilation and/or inhibition of platelet aggregation or other disorders where prostacyclin has shown benefit, such as in treating pulmonary hypertension. Accordingly, the present invention provides methods for inducing prostacyclin-like effects in a subject comprising administering a pharmaceutically effective amount of one or more of the compounds described herein, such as those of structure I above, preferably orally, to a patient in need of such treatment. As an example, the vasodilating effects of the present compounds can be used to treat pulmonary hypertension, which result from various forms of connective tissue disease, such as lupus, scleroderma or mixed connective tissue disease. These compounds are thus useful for the treatment of pulmonary hypertension.

In another embodiment, the present invention also provides methods of promoting prostacyclin-like effect in a subject by administering a pharmaceutically effective amount of a compound of structure II:

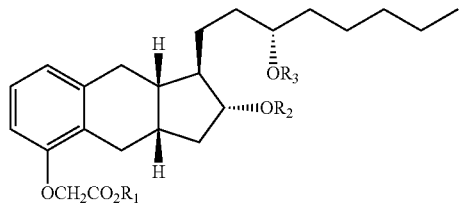

wherein, $R^1$ is independently selected from the group consisting of H, substituted and unsubstituted alkyl groups, arylalkyl groups and groups wherein $OR^1$ form a substituted or unsubstituted glycolamide ester;

$R^2$ and $R^3$ may be the same or different and are independently selected from the group consisting of H, phosphate and groups wherein $OR^2$ and $OR^3$ form esters of amino acids or proteins, with the proviso that all of $R^1$, $R^2$ and $R^3$ are not H;

an enantiomer of the compound; and a pharmaceutically acceptable salt of the compound.

In groups wherein $OR^1$ form a substituted or unsubstituted glycolamide ester, $R^1$ can be —$CH_2CONR^4R^5$, wherein $R^4$ and $R^5$ may be the same or different and are independently selected from the group consisting of H, OH, substituted and unsubstituted alkyl groups, —$(CH_2)_mCH_3$, —$CH_2OH$, and —$CH_2(CH_2)_nOH$, with the proviso that m is 0, 1, 2, 3 or 4, and n is 0, 1, 2, 3 or 4.

In other methods of inducing vasodilation or treating hypertension, $R^1$ can be a $C_1$-$C_4$ alkyl group, such as methyl, ethyl, propyl or butyl. In other methods $R^1$ is a substituted or unsubstituted benzyl groups, such as —$CH_2C_6H_5$, —$CH_2C_6H_4NO_2$, —$CH_2C_6H_4OCH_3$, —$CH_2C_6H_4Cl$, —$CH_2C_6H_4(NO_2)_2$, or —$CH_2C_6H_4F$. The benzyl group can be ortho, meta, para, ortho/para substituted and combinations thereof. Suitable substituents on the aromatic ring include halogens (fluorine, chlorine, bromine, iodine), —$NO_2$ groups, —$OR^{16}$ groups wherein $R^{16}$ is H or a $C_1$-$C_1$ alkyl group, and combinations thereof.

Alternatively, when $R^1$ is —$CH_2CONR^4R^5$ then $R^4$ and $R^5$ may be the same or different and are independently selected from the group consisting of H, OH, —$CH_3$, and —$CH_2CH_2OH$. In these methods, where $R^1$ is not H, generally one or both of $R^2$ and $R^3$ are H.

In some methods, one or both of $R^2$ and $R^3$ are H and $R^1$ is —$CH_3$, —$CH_2C_6H_5$. In other methods where one or both of $R^2$ and $R^3$ are H, then $R^1$ is —$CH_2CONR^4R^5$, and one or both of $R^4$ and $R^5$ are H, —OH, —$CH_3$, —$CH_2CH_2OH$.

In methods where one or both of $R^2$ and $R^3$ are not H, $R^2$ and $R^3$ can be independently selected from phosphate and groups wherein $OR^2$ and $OR^3$ are esters of amino acids, dipeptides, esters of tripeptides and esters of tetrapeptides. In some embodiments, only one of $R^2$ or $R^3$ is a phosphate group. In methods where at least one of $R^2$ and $R^3$ is not H, generally $R^1$ is H. In other methods, one of $R^2$ or $R^3$ is H and the other $R^2$ or $R^3$ is as defined elsewhere herein. In some methods, $R^2$ is H and $R^3$ is not H. In additional embodiments, $R^1$ and $R^3$ are H and $R^2$ is a group wherein $OR^2$ is an ester of an amino acid or a dipeptide. In further embodiments, $R^1$ and $R^2$ are H and $R^3$ is a group wherein $OR^3$ is an ester of an amino acid or a dipeptide.

In the methods, where one or both of the $OR^2$ and $OR^3$ groups form esters of amino acids or peptides, i.e., dipeptides, tripeptides or tetrapeptides, these can be depicted generically as —$COCHR^6NR^7R^8$ wherein $R^6$ is selected from the group consisting of amino acid side chains, $R^7$ and $R^8$ may be the same or different and are independently selected from the group consisting of H, and —$COCHR^9NR^{10}R^{11}$. In the embodiments wherein the amino acid is proline, $R^7$ together with $R^6$ forms a pyrrolidine ring structure. $R^6$ can be any of the naturally occurring amino acid side chains, for example —$CH_3$ (alanine), —$(CH_2)_3NHCNH_2NH$ (arginine), —$CH_2CONH_2$ (asparagine), —$CH_2COOH$ (aspartic acid), —$CH_2SH$ (cysteine), —$(CH_2)_2CONH_2$ (glutamine), —$(CH_2)_2COOH$ (glutamic acid), —H (glycine), —$CHCH_3CH_2CH_3$ (isoleucine), —$CH_2CH(CH_3)_2$ (leucine), —$(CH_2)_4NH_2$ (lysine), —$(CH_2)_2SCH_3$ (methionine), —$CH2Ph$ (phenylalanine), —$CH_2OH$ (serine), —$CHOHCH_3$ (threonine), —$CH(CH_3)_2$ (valine),

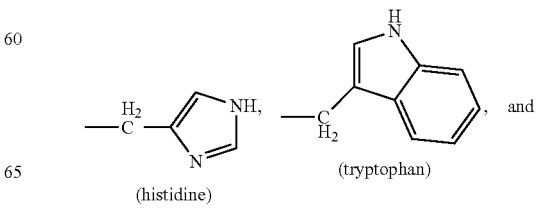

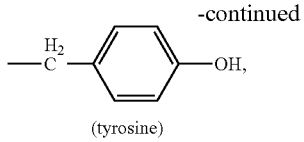

(tyrosine)

—$(CH_2)_3NHCONH_2$ (citrulline) or —$(CH_2)_3NH_2$ (ornithine). Ph designates a phenyl group.

In the above methods, $R^7$ and $R^8$ may be the same or different and are selected from the group consisting of H, and —$COCHR^9NR^{10}R^{11}$, wherein $R^9$ is a side chain of amino acid, $R^{10}$ and $R^{11}$ may be the same or different and are selected from the group consisting of H, and —$COCHR^{12}NR^{13}R^{14}$, wherein $R^{12}$ is an amino acid side chain, $R^{13}$ and $R^{14}$ may be the same or different and are independently selected from the group consisting of H, and —$COCHR^{15}NH_2$. One skilled in the art will realize that the peptide chains can be extended on the following scheme to the desired length and include the desired amino acid residues.

In the embodiments where either or both of $OR^2$ and $OR^3$ groups form an ester of a peptide, such as dipeptide, tripeptide, tetrapeptide, etc. the peptides can be either homopeptides, i.e., repeats of the same amino residue, or heteropeptides, i.e., made up of different combinations of amino acids.

As will be understood by the skilled artisan when only one of $R^7$ and $R^8$ includes a peptide bond to further amino acid, such as in the di, tri and tetrapeptides, the resulting peptide chain will be linear. When both $R^7$ and $R^8$ include a peptide bond, then the peptide can be branched.

In still other methods $R^1$ is H and one of $R^2$ or $R^3$ is a phosphate group or H while the other $R^2$ or $R^3$ is a group such the $OR^2$ or $OR^3$ is an ester of an amino acid, such as an ester of glycine or alanine.

In some methods, the administered compound can have an oral bioavailability that is at least 25%, 50% 100%, 200%, 400% of the oral bioavailability of treprostinil. It is generally preferred to administer compounds that have higher absolute oral bioavailabilities, such as 15%, 20%, 25%, 30% and 40%, 45%, 50%, 55%, 60% or more when administered orally.

Treprostinil has also been discovered to inhibit metastasis of cancer cells as disclosed in U.S. patent application Ser. No. 10/006,197 filed Dec. 10, 2001 and Ser. No. 10/047,802 filed Jan. 16, 2002, both of which are hereby incorporated into this application. Accordingly, the compounds described above, and in particular those of structure I and II, can also be used in the treatment of cancer and cancer related disorders, and as such the present invention provides pharmaceutical compositions and methods for treating cancer. Suitable formulations and methods of using the present compounds can be achieved by substituting the compounds of the present invention, such as those of structure I and II and in particular prodrugs of treprostinil, for the active compounds disclosed in U.S. patent application Ser. Nos. 10/006,197 and 10/047,802 filed Jan. 16, 2002.

Synthesis of the following compounds of structure I and structure II can be achieved as follows:

Synthesis of Methyl Ester of Treprostinil (2) and Biphosphate Ester of Treprostinil

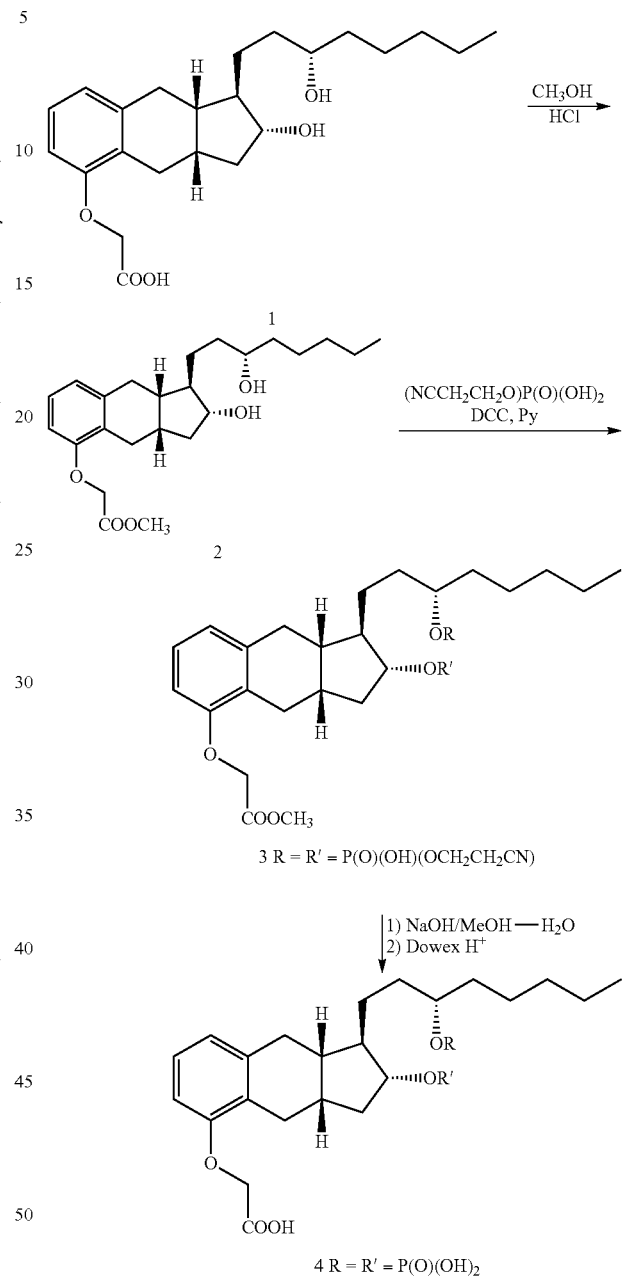

Synthesis of Methyl Ester of Treprostinil (2)

Methyl ester of treprostinil (2) was prepared by treating 1.087 g (2.8 mmoles) of treprostinil (1) with 50 ml of a saturated solution of dry hydrochloric acid in methanol. After 24 hours at room temperature, the methanol was evaporated to dryness and the residue was taken in 200 ml dichloromethane. The dichloromethane solution was washed with a 10% aqueous potassium carbonate solution, and then with water to a neutral pH, it was dried over sodium sulfate, filtered and the solvent was removed in vacuo affording treprostinil methyl ester (2) in 98% yield as a yellow oil. The crude methyl ester was used as such in subsequent reactions.

Synthesis of Biphosphate Ester of Treprostinil (4)

The procedure was adapted after Steroids, 2(6), 567-603 (1963). The methyl ester of treprostinil (2) (60 mg, 0.15 mmoles) was dissolved in 2 ml dry pyridine and a pyridinium solution of the previously prepared pyridinium solution of 2-cyanoethylphosphate 1M (0.3 ml, 0.3 mmoles) (cf. Methods in Enzymology, 1971, 18(c), 54-57) were concentrated to dryness in vacuo at 40° C. Anhydrous pyridine was added and the reaction mixture was again concentrated; the operation was repeated twice in order to remove water completely. Finally the residue was dissolved in 2 ml anhydrous pyridine and 190 mg (0.9 mmoles) dicyclohexylcarbodiimide were added as a solution in 2 ml anhydrous pyridine. The reaction mixture in a closed flask was stirred magnetically for 48 hours at room temperature. 1 ml water was added and after one hour, the mixture was concentrated to a thick paste in vacuo. The reaction mixture was treated overnight at room temperature with 3 ml of a 1/9 water/methanol solution containing 35 mg sodium hydroxide. The white solid (dicyclohexylurea) formed was removed by filtration and it was washed well with water. The aqueous-methanolic solution was concentrated almost to dryness in vacuo, water was added and the solution was extracted with n-butanol (3×2 ml), then with methylene chloride (1×2 ml). The pH of the solution was adjusted to 9.0 by treatment with a sulfonic acid ion exchange resin (H+ cycle-Dowex), treatment with Dowex resin for a longer time (~12 hours) lead to both the cleavage of the TBDMS group and the recovery of the free carboxyl group. The resin was filtered and the solution was concentrated to dryness affording the corresponding bisphosphate 4 (43 mg, yield 52%).

Synthesis of 3'-Monophosphate Ester of Treprostinil (8) and 2-Monophosphate Ester of Treprostinil (10)

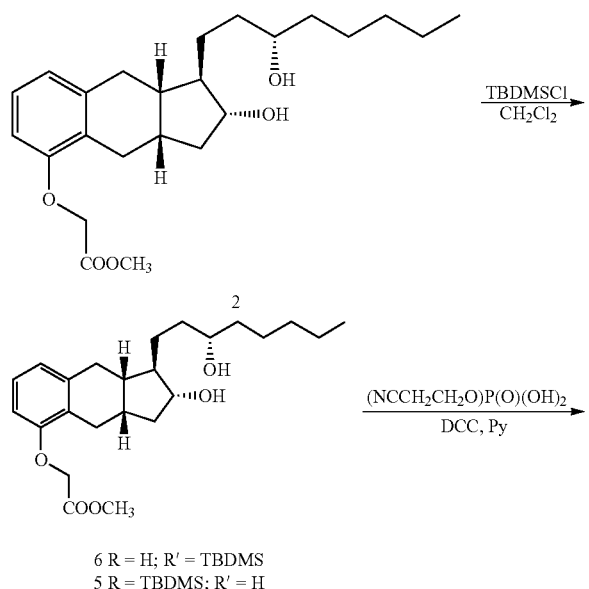

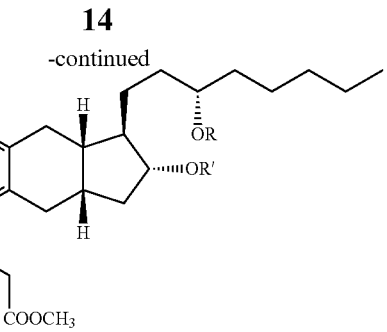

7 R = P(O)(OH)(OCH$_2$CH$_2$CN); R' = TBDMS
9 R = TBDMS; R' = P(O)(OH)(OCH$_2$CH$_2$CN)

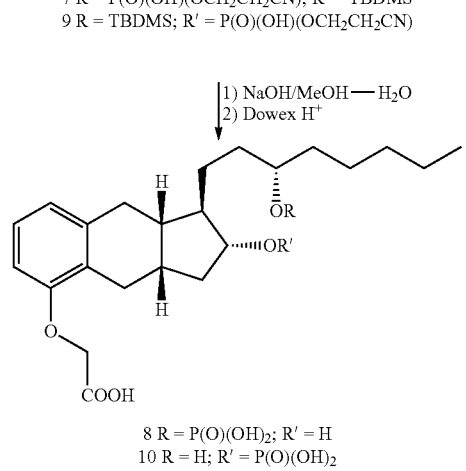

8 R = P(O)(OH)$_2$; R' = H
10 R = H; R' = P(O)(OH)$_2$

Synthesis of Monoprotected TBDMS Methyl Ester of Treprostinil (5 and 6)

The procedure was adapted from Org. Synth., 1998, 75, 139-145. The treprostinil methyl ester (2) (305.8 mg, 0.75 mmoles) was dissolved in 15 ml anhydrous dichloromethane and the solution was cooled on an ice bath to 0° C. Imidazole (102 mg, 1.5 mmoles) and tert-butyldimethyl silyl chloride (226.2 mg, 1.5 mmoles) were added and the mixture was maintained under stirring at 0° C. for 30 minutes, then stirred overnight at room temperature. Water (25 ml) was added and the organic layer was separated. The aqueous layer was then extracted with dichloromethane (3×50 ml). The organic layers were dried over Na$_2$SO$_4$, the solution was filtered and the solvent was removed in vacuo affording 447 mg crude reaction product. The crude reaction product was separated by column chromatography (silica gel, 35% ethyl acetate/hexanes) affording 140 mg bis-TBDMS protected Treprostinil methyl ester, 160 mg 2-TBDMS protected treprostinil methyl ester (6) and 60 mg 3'-TBDMS protected Treprostinil methyl ester (5).

Synthesis of Monophosphate Ester of Treprostinil 8/10

The procedure was adapted after Steroids, 1963, 2(6), 567-603 and is the same for (8) and (10) starting from (6) and (5), respectively. The TBDMS protected methyl ester of treprostinil (6) (46 mg, 0.09 mmoles) was dissolved in 2 ml dry pyridine and a pyridinium solution of the previously prepared pyridinium solution of 2-cyanoethylphosphate 1M (0.2 ml, 0.2 mmoles) (cf. Methods in Enzymology, 1971, 18(c), 54-57) were concentrated to dryness in vacuo at 40° C. Anhydrous pyridine was added and the reaction mixture was again concentrated; the operation was repeated twice in order to remove water completely. Finally the residue was dissolved in 2 ml anhydrous pyridine and 116 mg (0.56 mmoles) dicyclohexylcarbodiimide were added as a solution in 2 ml anhydrous pyridine. The reaction mixture in a closed flask was stirred magnetically for 48 hours at room temperature in the dark. 5 ml water were added and after one hour, the mixture was concentrated to a thick paste in vacuo. The reaction mixture was treated overnight at room temperature with 10 ml of a 1/9 water/methanol solution containing 100 mg sodium hydroxide. The white solid (dicyclohexylurea) formed was removed by filtration and it was washed well with water. The aqueous-methanolic solution was concentrated almost to dryness in vacuo, water was added and the solution was extracted with n-butanol (3×10 ml), then with methylene chloride (1×10 ml). The pH of the solution was adjusted to 9.0 by treatment with a sulfonic acid ion exchange resin (H+ cycle-Dowex); treatment with Dowex resin for a longer time (~~12 hours) lead to both the cleavage of the TBDMS group and the recovery of the free carboxyl group. The resin was filtered and the solution was concentrated to dryness affording the corresponding monophosphate 8 (33 mg, yield 68%).

Synthesis of Methyl Ester of Treprostinil (2)

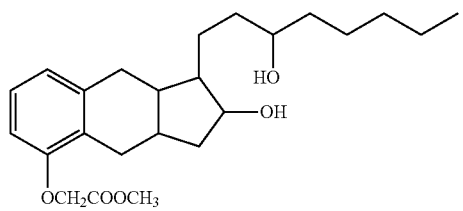

2

(2) (1 g; 2.56 mmol) was added to methanol (50 ml) prior saturated with gaseous hydrochloric acid and the mixture swirled to give a clear solution that was left to stand overnight at room temperature. Solvent was removed in vacuo and the residue was neutralized with a 20% potassium carbonate solution and extracted in dichloromethane. The organic layer was washed with water, dried over anhydrous magnesium sulfate and evaporated to yield the crude product (0.96 g). Purification by preparative tlc (silica gel plate; eluent: 7:3 (v/v) hexane-ethyl acetate) afforded 2 (0.803; 77.5%), colorless oil.

Synthesis of Treprostinil Diethanolamine (UT-15C)

Treprostinil acid is dissolved in a 1:1 molar ratio mixture of ethanol:water and diethanolamine is added and dissolved. The solution is heated and acetone is added as an antisolvent during cooling.

Synthesis of Diglycil Ester of Treprostinil Methyl Ester (12)

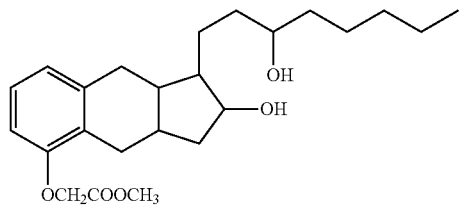 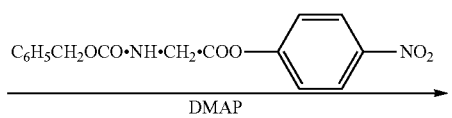

2

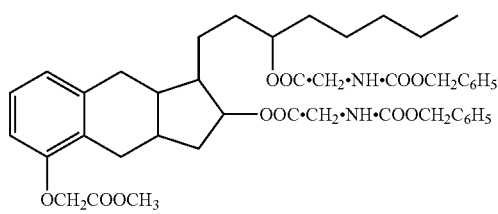 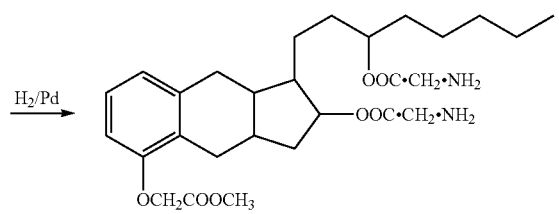

11                                          12

To a magnetically stirred solution of (2) methyl ester 2 (0.268 g; 0.66 mmol) in dichloromethane (30 ml) N-carbobenzyloxyglycine p-nitrophenyl ester (0.766 g; 2.32 mmol) and 4-(dimethyamino)pyridine (250 mg; 2.05 mmol) were successively added. The resulted yellow solution was stirred at 20° C. for 24 hrs., then treated with 5% sodium hydroxide solution (20 ml) and stirring continued for 15 mm. Dichloromethane (50 ml) was added, layers separated and the organic phase washed with a 5% sodium hydroxide solution (6×20 ml), water (30 ml), 10% hydrochloric acid (2×40 ml), 5% sodium bicarbonate solution (40 ml) and dried over anhydrous sodium sulfate. Removal of the solvent afforded crude (11) (0.61 g), pale-yellow viscous oil. Purification by flash column chromatography on silica gel eluting with gradient 9/1 to 1/2 (v/v) hexane-ethyl ether afforded 0.445 g (85.3%) of 11, white crystals, m.p. 70-72° C. 'Fl-NMR [CDCl$_3$; δ(ppm)]: 3.786 (s)(3H, COOC$\underline{H}_3$), 3.875 (d)(2H) and 3.940 (d)(2H)(NH—C$\underline{H}_2$—COO), 4.631 (s) (2H, OC$\underline{H}_2$COOCH3), 4.789 (m)(1H, adjacent to OOC—CH$_2$NHcbz) and 4.903 (m) (1H, adjacent to OOCCH$_2$NHcbz), 5.09 (s)(4H, C$_6$$\underline{H}_5$CH$_2$O), 5.378 (m)(1H) and 5.392 (m)(1H)(NH), 7.295-7.329 (m)(10H, C$_6$H$_5$). LR ESI-MS (m/z): 787.1 [M+H]⁺, 804.1 [M+NH₄]⁺, 809.3 [M+Na]⁺, 825.2 [M+K]⁺, 1590.5 [2M+NH₄]⁺, 1595.6 [2M+Na]⁺.

Methyl Ester, Diglycyl Ester (12)

A solution of ester (11) (0.4 g; 0.51 mmol) in methanol (30 ml) was introduced in the pressure bottle of a Parr hydrogenation apparatus, 10% palladium on charcoal (0.2 g; 0.197 mmol Pd) was added, apparatus closed, purged thrice with hydrogen and loaded with hydrogen at 50 μs.i. Stirring was started and hydrogenation carried out for 5 hrs. at room temperature. Hydrogen was removed from the installation by vacuum suction and replaced with argon. The catalyst was filtered off through celite deposited on a fit and the filtrate concentrated in vacuo to give 0.240 g (91%) of 4, white solid m.p. 98-100° C.

Synthesis of Benzyl Ester of Treprostinil (13)

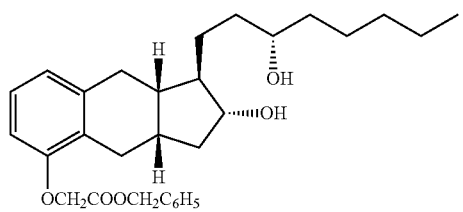

To a stirred solution of (2) (2 g; 5.12 mmol) in anhydrous tetrahydrofuran (20 ml) benzyl bromide (0.95 ml; 7.98 mmol) and freshly distilled triethylamine (1.6 ml; 11.48 mmol) were consecutively added at room temperature and the obtained solution was refluxed with stirring for 12 hrs. A white precipitate was gradually formed. Solvent was distilled off in vacuo and the residue treated with water (30 ml). Upon extraction with methylene chloride emulsion formation occurs. The organic and aqueous layers could be separated only after treatment with 5% hydrochloric acid solution (20 ml). The organic layer was washed with water, dried on anhydrous sodium sulfate, and evaporated, the residue was further dried under reduced pressure over phosphorus pentoxide to give a yellow viscous oil (2.32 g) that was purified by preparative thin layer chromatography (silica gel plate; eluent: 1:2, v/v, hexane/ethyl ether). Yield: 81.2%.

Synthesis of Bis-Glycyl Ester of Treprostinil (15)

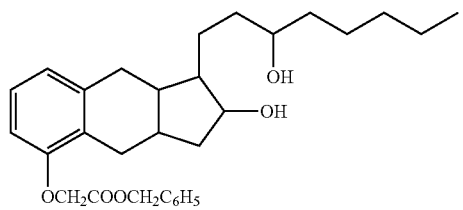

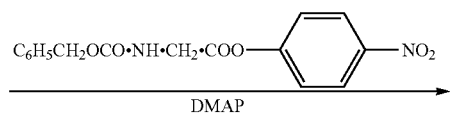

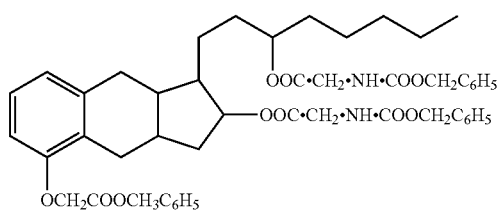

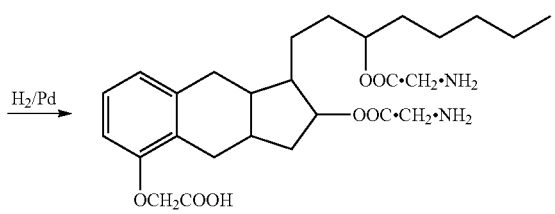

Benzy Ester, Di-cbzGly Ester (14)

To a magnetically stirred solution of benzyl ester 13 (1 g; 2.08 mmol) in dichloromethane (50 ml) N-carbobenzyloxyglycine p-nitrophenyl ester (2.41 g; 7.28 mmol) and 4-(dimethyamino) pyridine (788 mg; 6.45 mmol) were added. The resulted yellow solution was stirred at 20° C. for 21 hrs., then successively washed with a 5% sodium hydroxide solution (6×45 ml), 10% hydrochloric acid (2×40 ml), 5% sodium bicarbonate solution (40 ml) and dried over anhydrous sodium sulfate. Removal of the solvent, followed by drying over phosphorus pentoxide under reduced pressure, afforded crude 14 (2.61 g), pale-yellow oil. Purification by flash column chromatography on silica gel eluting with gradient 9:1 to 1:2 (v/v) hexane-ethyl ether gave (14 (1.51 g; 84.1%) as a colorless, very viscous oil.

Diglycyl Ester (15)

A solution of ester (14) (0.4 g; 0.46 mmol) in methanol (30 ml) was hydrogenated over 10% Pd/C as described for ester (12). Work-up and drying over phosphorus pentoxide in vacuo yielded 0.170 g (72.7%) of ester 15, white solid m.p. 155-158° C.

Synthesis of 3'-Glycyl Ester of Treprostinil 19

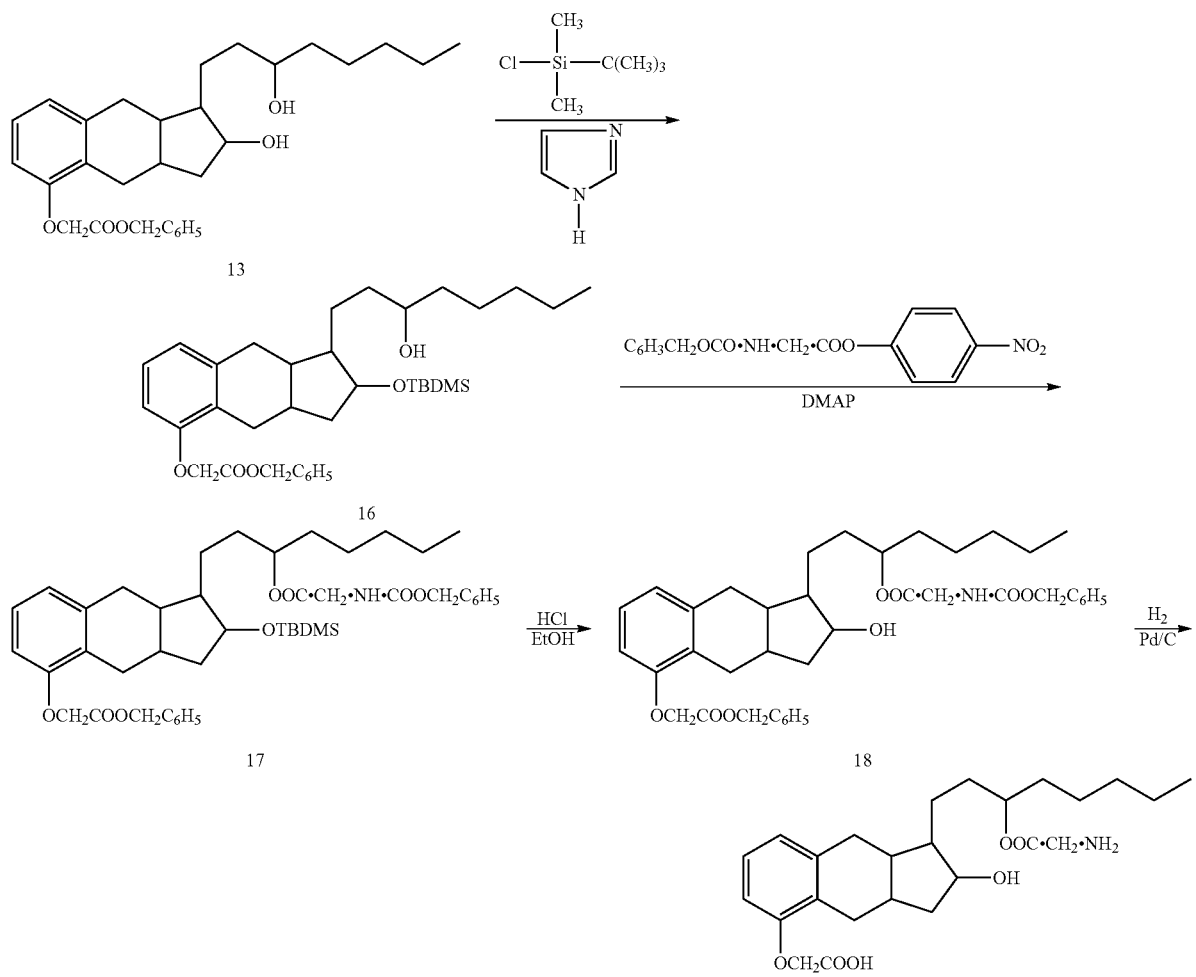

Benzyl Ester, t-Butyldimethysilyl Monoester (16)

A solution of tert-butyldimethylsilyl chloride (0.45 g; 2.98 mmol) in dichloromethane (8 ml) was added dropwise over 10 min., at room temperature, into a stirred solution of benzyl ester 13 (0.83 g; 1.73 mmol) and imidazole (0.33 g; 4.85 mmol) in dichloromethane (20 ml). Stirring was continued overnight then water (20 ml) was added, the mixture stirred for one hour, layers separated, organic layer dried over anhydrous sodium sulfate and concentrated in vacuo to give a slightly yellow oil (1.15 g). The crude product is a mixture of the mono-TBDMS (16) and di-TBDMS esters ($^1$H-NMR). Column chromatography on silica gel, eluting with a 9:1 (v/v) hexane-ethyl acetate mixture, readily afforded the di-ester (0.618 g) in a first fraction, and ester 16 (0.353 g; yield relative to 13:34.4%) in subsequent fractions. Analytical tlc on silica gel of the ester 16 showed only one spot (eluent: 3:2 (v/v) hexane-ethyl ether). Consequently, under the above reaction conditions, the other possible isomer (mono-TBDMS ester at the side-chain hydroxyl) was not observed.

Another experiment in which the molar ratio tert-butyldimethylsilyl chloride:ester 13 was lowered to 1.49 (followed by flash column chromatography of the product on silica gel, eluting with gradient 9.5/0.5 to 3/1 (v/v) hexane-ethyl ether) lead to a decreased content (36.5%, as pure isolated material) of the undesired di-OTBDMS by-product. The mono-OTBDMS ester fractions (45.1%; isolated material) consisted of ester 16 (98%) and its side-chain isomer (2%) that could be distinctly separated; the latter was evidenced (tlc, NMR) only in the last of the monoester fractions.

Benzyl Ester, Cbz-Glycyl Monoester (18)

To a magnetically stirred solution of ester 16 (0.340 g; 0.57 mmol) in dichloromethane (15 ml) N-carbobenzyloxyglycine p-nitrophenyl ester (0.445 g; 1.35 mmol) and 4-(dimethyamino) pyridine (150 mg; 1.23 mmol) were successively added. The solution was stirred at 20° C. for 40 hrs. Work-up as described for esters 11 and 14 yielded a crude product (0.63 g) containing 90% 17 and 10% 18 ($^1$H-NMR). To completely remove the protective TBDMS group, this mixture was dissolved in ethanol (30 ml) and subjected to acid hydrolysis (5% HCl, 7 ml) by stirring overnight at room temperature. Solvent was then removed under reduced pressure and the residue extracted in dichloromethane (3×50 ml); the organic layer was separated, washed once with water (50 ml), dried over sodium sulfate and concentrated in vacuo to give crude ester 18 (0.51 g). Purification by flash column chromatography as for esters 11 and 14 afforded ester 18 (0.150 g; overall yield: 39.1%) as a colorless, viscous oil.

Glycyl Monoester (19)

A solution of ester 18 (0.15 g; 0.22 mmol) in methanol (30 ml) was hydrogenated over 10% Pd/C as described for ester 12 and 15. Work-up and drying over phosphorus pentoxide in vacuo yielded ester 10 (0.98 g; 98.0%), white, shiny crystals m.p. 74-76° C. LR ESI-MS (m/z): 448.2 [M+H]$^+$, 446.4 [M−H]$^−$.

Synthesis of 3'-L-Leucyl Ester of Treprostinil 22 stirring continued at room temperature for 2 days. The solvent was removed in vacuo and the crude product (0.9 g) subjected to flash column chromatography on silica gel eluting with 9:1 hexane-ethyl acetate; the firstly collected fraction yielded an oil (0.51 g) which, based on the its NMR spectrum and tlc, was proved to be a 2:1 mixture of ester 20 and the starting ester 16. Preparative tlc on silica gel (eluent: ethyl acetate-hexane 1:4) gave pure 20, colorless oil (overall yield based on 7:62.6%).

Benzyl Ester, Cbz-L-Leucyl Monoester (21)

De-protection of the cyclopentenyl hydroxyl in the t-butyldimethysilyl monoester 20 succeeded by treatment with diluted hydrochloric acid solution as described for 18, with the exception that a 1:5 (v/v) chloroform-ethanol mixture,

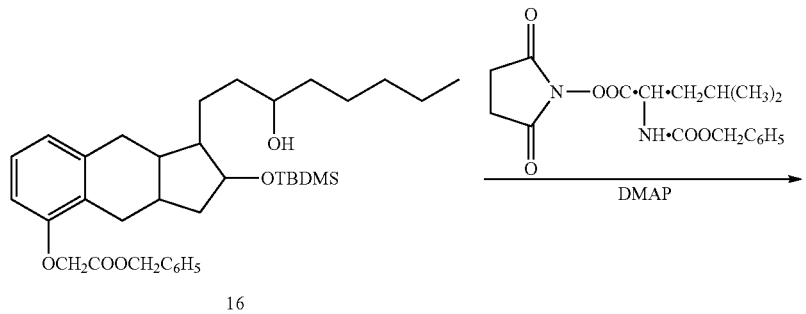

16

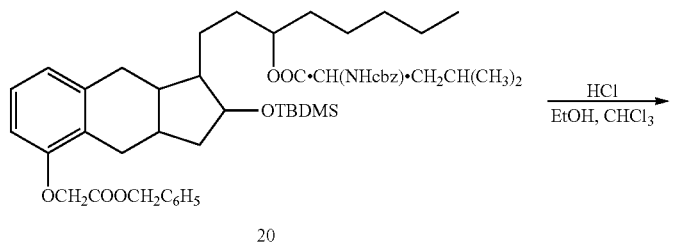

20

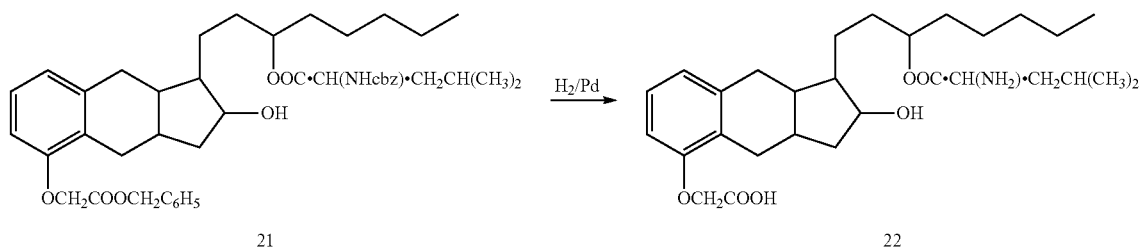

Benzyl Ester, t-Butyldimethysilyl Monoester, Cbz-L-Leucyl Monoester (20)

To a stirred solution of ester 16 (0.38 g; 0.64 mmol) and N-carbobenzyloxy-L-leucine N-hydroxysuccinimide ester (0.37 g; 1.02 mmol) in 10 ml dichloromethane 4-(dimethyamino)pyridine (0.17 g; 1.39 mmol) was added, then instead of ethanol alone, was used to ensure homogeneity. Work-up afforded 20, colorless oil, in 87.6% yield.

L-Leucyl Monoester (22)

Hydrogenolysis of the benzyl and N-carbobenzyloxy groups in 21 was carried out as for 18. Work-up afforded 22 (95.3%), white solid, m.p. 118-120° C.

Synthesis of 2-L-Leucyl Ester of Treprostinil 25

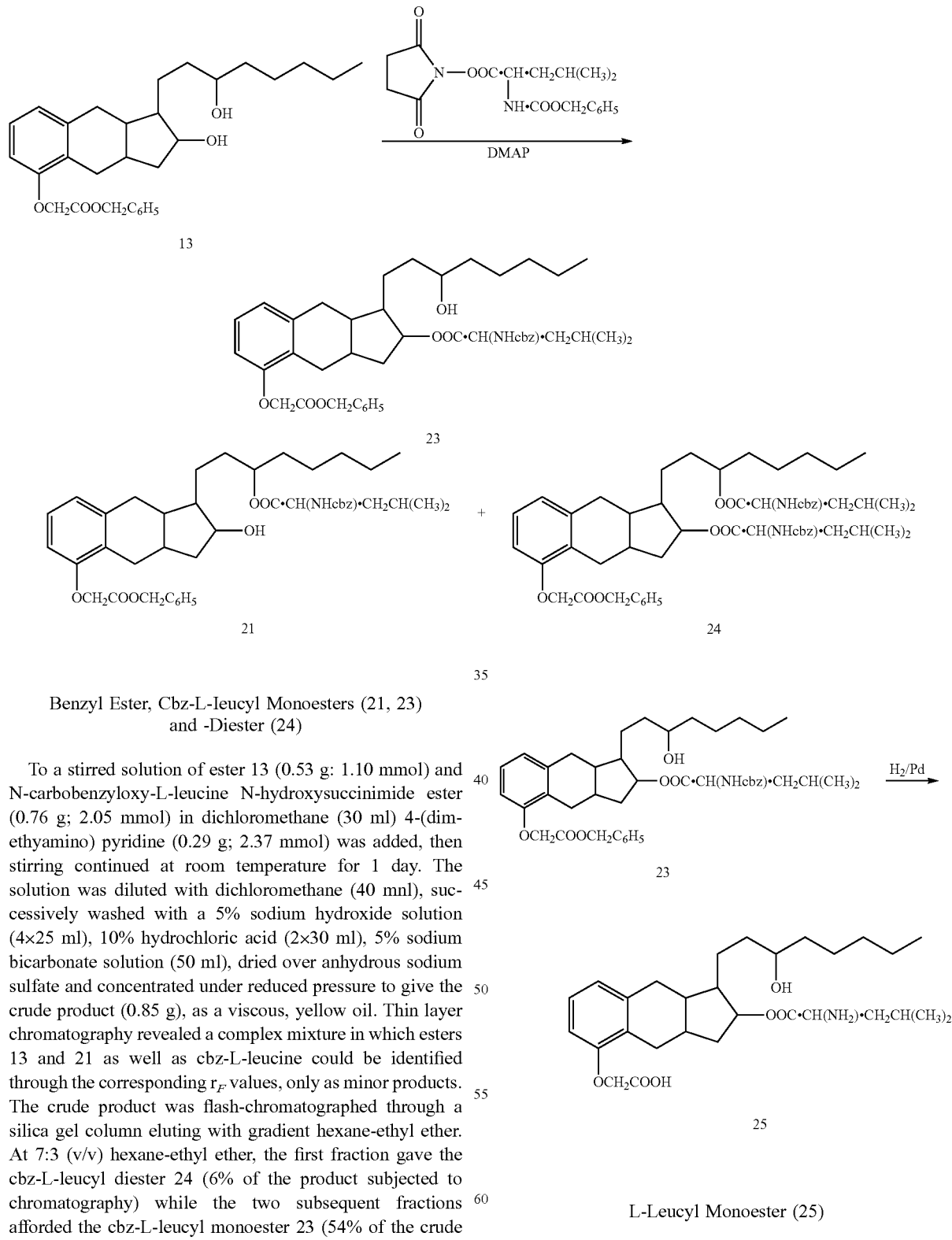

Benzyl Ester, Cbz-L-leucyl Monoesters (21, 23) and -Diester (24)

To a stirred solution of ester 13 (0.53 g: 1.10 mmol) and N-carbobenzyloxy-L-leucine N-hydroxysuccinimide ester (0.76 g; 2.05 mmol) in dichloromethane (30 ml) 4-(dimethyamino) pyridine (0.29 g; 2.37 mmol) was added, then stirring continued at room temperature for 1 day. The solution was diluted with dichloromethane (40 mnl), successively washed with a 5% sodium hydroxide solution (4×25 ml), 10% hydrochloric acid (2×30 ml), 5% sodium bicarbonate solution (50 ml), dried over anhydrous sodium sulfate and concentrated under reduced pressure to give the crude product (0.85 g), as a viscous, yellow oil. Thin layer chromatography revealed a complex mixture in which esters 13 and 21 as well as cbz-L-leucine could be identified through the corresponding $r_F$ values, only as minor products. The crude product was flash-chromatographed through a silica gel column eluting with gradient hexane-ethyl ether. At 7:3 (v/v) hexane-ethyl ether, the first fraction gave the cbz-L-leucyl diester 24 (6% of the product subjected to chromatography) while the two subsequent fractions afforded the cbz-L-leucyl monoester 23 (54% of the crude product, as pure isolated 23; 57.6% yield, relative to 2). Purity of both compounds was verified by analytical tlc and NMR. The other isomer, cbz-L-leucyl monoester 21 constituted only about 5% of the crude product and was isolated by preparative tlc of the latter only a 3:1 23/21 mixture.

L-Leucyl Monoester (25)

Hydrogenolysis of 23 to the ester 25 was performed as described for compound 12 but reaction was carried out at 35 µs.i., overnight. Work-up and drying over phosphorus pentoxide in vacuo afforded 25, white solid m. p. 153-155° C., in quantitative yield.

Synthesis of 3'-L-Alanyl Ester of Treprostinil 30

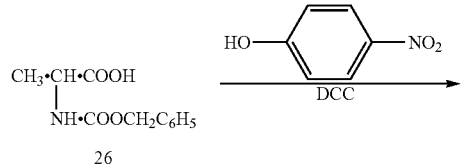

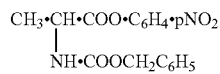

N-Cbz-L-Alanyl p-Nitro Phenyl Ester (27)

To a stirred solution containing N-carbobenzyloxy-L-alanine (1 g; 4.48 mmol) and p-nitrophenol (1 g; 7.19 mmol) in anhydrous tetrahydrofuran (7 ml) a fine suspension of 1,3-dicyclohexylcarbodiimide (1.11 g; 5.38 mmol) in tetrahydrofuran (5 ml) was added over 30 min. Stirring was continued at room temperature for 18 hrs., glacial acetic acid (0.3 ml) added, 1,3-dicyclohexylurea filtered off and solvent removed in vacuo, at 40° C., to give a viscous, yellow-reddish oil (2.5 g). The $^1$H-NMR spectrum showed a mixture consisting of N-carbobenzyloxy-L-alanine p-nitrophenyl ester (27), unreacted p-nitrophenol and a small amount of DCU, which was used as such in the next reaction step.

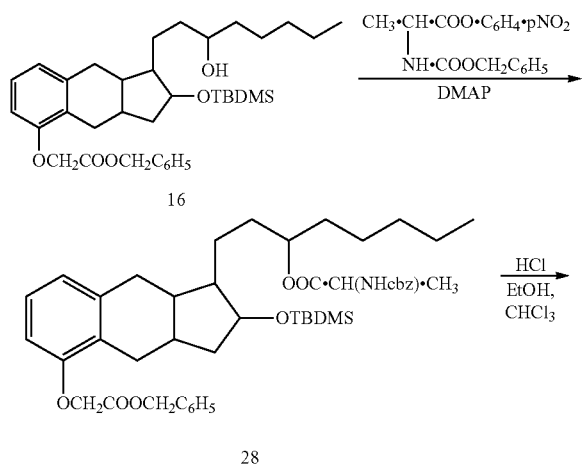

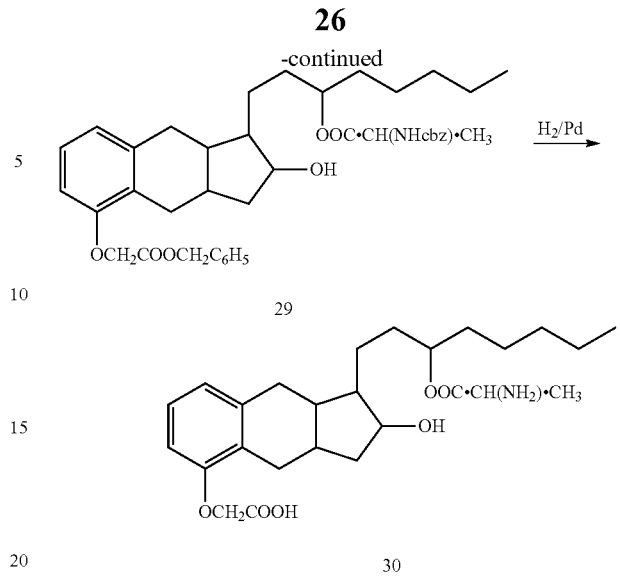

Benzyl Ester, Cbz-L-Alanyl Monoester (29)

A solution of 4-(dimethylamino)pyridine (0.30 g; 2.49 mmol) in dichloromethane (3 ml) was quickly dropped (over 5 min.) into a magnetically stirred solution of ester 16 (0.37 g; 0.62 mmol) and crude N-carbobenzyloxy-L-alanine p-nitrophenyl ester (0.98 g) in dichloromethane (12 ml). The mixture was stirred overnight at room temperature, then diluted with dichloromethane (50 ml), and thoroughly washed with a 5% sodium hydroxide solution (7×35 ml), 10% hydrochloric acid (3×35 ml), 5°/a sodium bicarbonate solution (50 ml), dried over anhydrous sodium sulfate and concentrated under reduced pressure to give the crude ester 28 (1.1 g). The latter was dissolved in ethanol (30 ml), 5% hydrochloric acid (8 ml) and chloroform (5 ml) were added and the solution stirred overnight. Solvents were removed in vacuo, the residue taken-up in dichloromethane, washed to pH 7 with a 5% sodium hydrogencarbonate solution, dried over anhydrous sodium sulfate and the solvent evaporated affording crude 29 (1.04 g). Purification by column chromatography on silica gel, eluting with gradient hexane-ethyl ether, enabled separation of a fraction (at hexane:ethyl ether=1:1 v/v) of pure 29 as a colorless very viscous oil (0.11 g; 25.8% overall yield, based on 16).

L-Alanyl Monoester (30)

Removal of the benzyl and N-carbobenzyloxy groups in 29 was achieved through catalytic hydrogenation as described for 12. Ester 30 was obtained (yield: 97.2%) as a pale-yellow, partially crystallized, oil.

Synthesis of the 3'-L-Valine Ester of Treprostinil Benzyl Ester 33

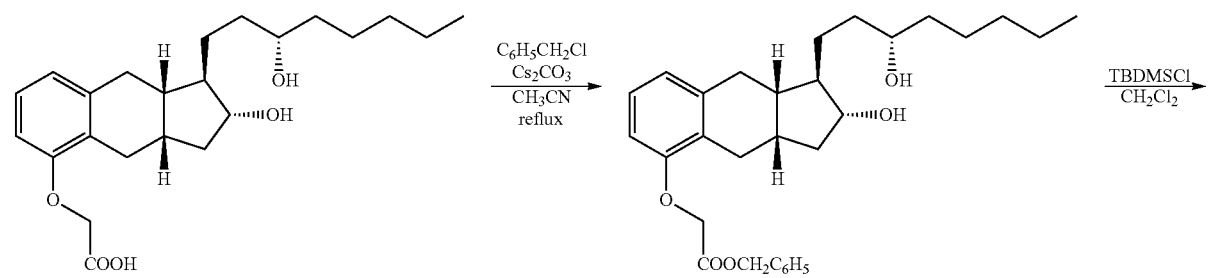

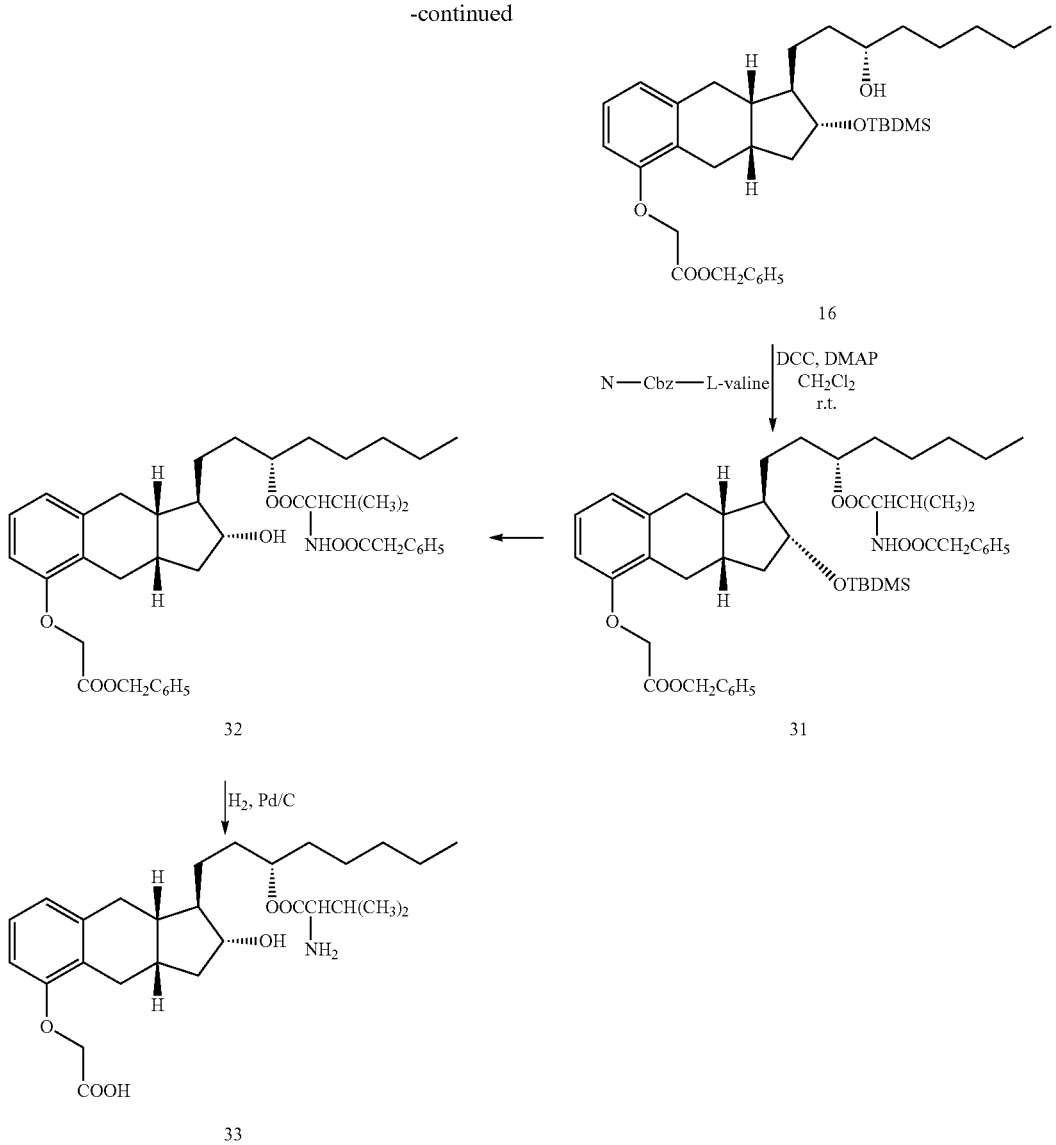

Synthesis of the Benzyl Ester of Treprostinil 13

The benzyl ester 11 was synthesized by adapting the method described by J. C. Lee et al. in Organic Prep. and Proc. Intl., 1996, 28(4), 480-483. To a solution of 1 (620 mg, 1.6 mmoles) and cesium carbonate (782.4 mg, 2.4 mmoles) in acetonitrile (30 ml) was added benzyl bromide (0.48 ml, 4 mmoles) and the mixture was stirred at reflux for 1 hour. After cooling at room temperature, the precipitate was filtered off and the filtrate was concentrated in vacuo. The residue was dissolved in chloroform (150 ml) and washed with a 2% aqueous solution of $NaHCO_3$ (3×30 ml). The organic layer was washed with brine, dried on $Na_2SO_4$, filtered and the solvent was removed in vacuo to afford 750 mg of the crude benzyl ester 13 (yield 98%) as a yellow viscous oil. The crude benzyl ester 13 can be purified by column chromatography (100-0% dichloromethane(methanol) but it can also be used crude in subsequent reactions.

Synthesis of the TBDMS Protected Treprostinil Benzyl Ester 16

The procedure for the synthesis of the TBDMS protected benzyl ester was adapted from Organic Synth., 1998, 75, 139-145. The benzyl ester 13 (679 mg, 1.4 mmoles) was dissolved in anhydrous dichloromethane (20 ml) and the solution was cooled to 0° C. on an ice bath. Imidazole (192 mg, 2.8 mmoles) and t-butyldimethylsilyl chloride (TBDM-SCl) (420 mg, 2.8 mmoles) were added and the mixture was maintained under stirring for another half hour on the ice bath and then it was left overnight at room temperature. 40 ml water was added to the reaction mixture and the organic layer was separated. The aqueous layer was extracted with 3×50 ml dichloromethane. The combined organic layers were dried over $Na_2SO_4$, filtered and the solvent was removed in vacuo. This afforded 795 mg of material which proved to be a mixture of the desired mono TBDMS protected 5 benzyl ester with the bis-TBDMS protected benzyl ester. Pure 16 (249 mg) was obtained by column chromatography on silica gel (eluent 35% ethyl acetate/hexane).

Synthesis of N-Cbz-L-Valine Ester of the TBDMS Protected Treprostinil Benzyl Ester 31

The procedure used was adapted from Tetrahedron Lett., 1978, 46, 4475-4478. A solution of NCbz-L-valine (127 mg, 0.5 mmoles), N,N-dicyclohexylcarbodiimide (DCC) (111 mg, 0.5 mmoles), compound 16 (249 mg, 0.4 mmoles) and 4-(dimethylamino)pyridine (DMAP) (6 mg, 0.05 mmoles) in anhydrous dichloromethane (15 ml) was stirred at room temperature until esterification was complete. The solution was filtered and the formed N,N-dicyclohexylurea was filtered. The filtrate was diluted with dichloromethane (80 ml) and washed with water (3×30 ml), a 5% aqueous acetic acid solution (2×30 ml) and then again with water (3×30 ml). The organic layer was dried over $Na_2SO_4$ and the solvent was evaporated in vacuo affording 369 mg crude 31. Pure 31 was obtained by chromatography (silica gel, 35% ethyl acetate/hexane).

Synthesis of the 3'-N-Cbz-L-Valine Ester of Treprostinil Benzyl Ester 32

Cleavage of the TBDMS group in compound 31 was achieved using an adaptation of the procedure described in Org. Letters, 2000, 2(26), 4177-4180. The N-Cbz-L-valine ester of the TBDMS protected benzyl ester 31 (33 mg, 0.04 mmoles) was dissolved in methanol (5 ml) and tetrabutylammonium tribromide (TBATB) (2 mg, 0.004 mmoles) was added. The reaction mixture was stirred at room temperature for 24 hrs until the TBDMS deprotection was complete. The methanol was evaporated and the residue was taken in dichloromethane. The dichloromethane solution was washed with brine and then dried over $Na_2SO_4$. After filtering the drying agent the solvent was evaporated to dryness affording 30.2 mg of crude compound 32.

Synthesis of the 3'-L-Valine Ester of Treprostinil 33

The benzyl and benzyl carboxy groups were removed by catalytic hydrogenation at atmospheric pressure in the presence of palladium 10% wt on activated carbon. The 3'-N-Cbz-L-valine ester of benzyl ester 32 (30.2 mg, 0.04 mmoles) was dissolved in methanol (10 ml) and a catalytic amount of Pd/C was added. Under magnetic stirring the air was removed from the flask and then hydrogen was admitted. The reaction mixture was maintained under hydrogen and stirring at room temperature for 24 hrs, then the hydrogen was removed with vacuum. The reaction mixture was then filtered through a layer of celite and the solvent was removed in vacuo to afford the pure 3'-L-valine ester of Treprostinil 33 (15 mg, 0.03 mmoles).

Synthesis of 2-L-Valine Ester of Treprostinil 36/Bis-L-Valine Ester of Trenrostinil 37

Synthesis of 2-L-Alanine Ester of Treprostinil 36'/Bis-L-Alanine Ester of Treprostinil 37'

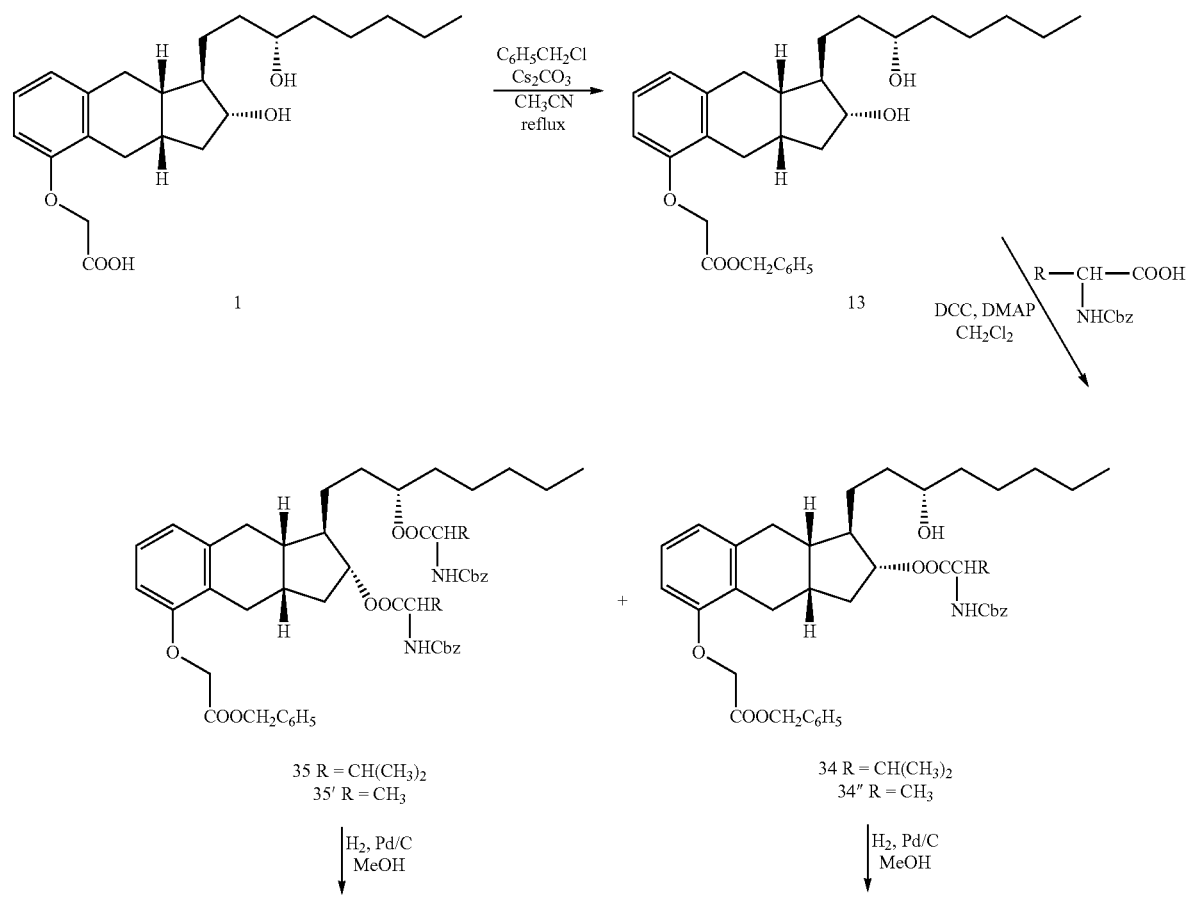

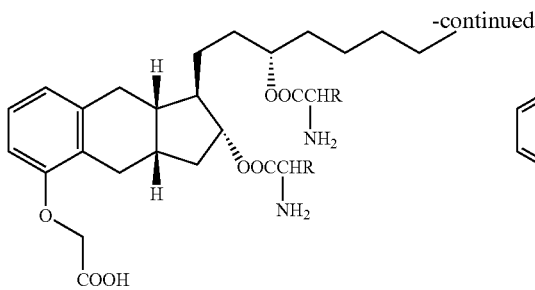
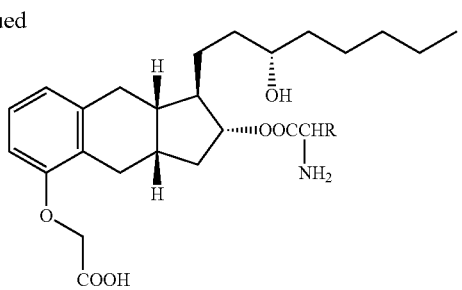

37 R = CH(CH₃)₂
37' R = CH₃

36 R = CH(CH₃)₂
36' R = CH₃

Synthesis of 2-N-Cbz-L-Valine Ester of Treprostinil Benzyl Ester 34 and Bis-N-Cbz-L-Valine Ester of Treprostinil Benzyl Ester 35

The procedure used was adapted from Tetrahedron Lett., 1978, 46, 4475-4478. A solution of NCbz-L-valine (186 mg, 0.7 mmoles), N,N-dicyclohexylcarbodiimide (DCC) (167 mg, 0.8 mmoles), compound 13 (367 mg, 0.8 mmoles) and 4-(dimethylamino)pyridine (DMAP) (12 mg, 0.09 mmoles) in anhydrous dichloromethane (15 ml) was stirred at room temperature until esterification was complete. The solution was filtered and the formed N,N-dicyclohexylurea was filtered. The filtrate was diluted with dichloromethane (100 ml) and washed with water (3×50 ml), a 5% aqueous acetic acid solution (2×50 ml) and then again with water (3×50 ml). The organic layer was dried over Na₂SO₄ and the solvent was evaporated in vacuo affording 556 mg crude product. The product was separated by chromatography (silica gel, 35% ethyl acetate/hexane) yielding 369.4 mg 2-valine ester 34 and 98 mg bis-valine ester 35.

Synthesis of 2 N-Cbz-L-Alanine Ester of Treprostinil Benzyl Ester 34' and Bis-N-Cbz-L-Alanine Ester of Treprostinil Benzyl Ester 35'

The procedure used was adapted from Tetrahedron Lett., 1978, 46, 4475-4478. A solution of NCbz-L-alanine (187 mg, 0.84 mmoles), N,N-dicyclohexylcarbodiimide (DCC) (175 mg, 0.85 mmoles), compound 13 (401 mg, 0.84 mmoles) and 4-(dimethylamino)pyridine (UMAP) (11.8 mg, 0.1 mmoles) in anhydrous dichloromethane (15 ml) was stirred at room temperature until esterification was complete. The solution was filtered and the formed N,N-dicyclohexylurea was filtered. The filtrate was diluted with dichloromethane (100 ml) and washed with water (3×50 ml), a 5% aqueous acetic acid solution (2×50 ml) and then again with water (3×50 ml). The organic layer was dried over Na₂SO₄ and the solvent was evaporated in vacuo affording 516 mg crude product. The product was separated by chromatography (silica gel, 35% ethyl acetate/hexane) yielding 93.4 mg 2-alanine ester 34' and 227 mg bis-alanine ester 35'.

Synthesis of 2-L-Valine Ester of Treprostinil 36/Bis-L-Valine Ester of Treprostinil 37

The benzyl and benzyl carboxy groups were removed by catalytic hydrogenation at atmospheric pressure in the presence of palladium 10% wt on activated carbon. The 2-N-Cbz-L-valine ester of Treprostinil benzyl ester 34 (58.2 mg, 0.08 mmoles)/bis-N-Cbz-L-valine ester of Treprostinil benzyl ester 35 (55.1 mg, 0.06 mmoles) was dissolved in methanol (10 ml) and a catalytic amount of Pd/C was added. Under magnetic stirring the air was removed from the flask and hydrogen was admitted. The reaction mixture was maintained under hydrogen and stirring at room temperature for 20 hrs, then hydrogen was removed with vacuum. The reaction mixture was then filtered through a layer of celite and the solvent was removed in vacuo to afford the pure 2-L-valine ester of Treprostinil 36 (40 mg, 0.078 mmoles)/bis-L-valine ester of Treprostinil 37 (23 mg, 0.04 mmoles).

Synthesis of 2-L-Alanine Ester of Treprostinil 36'/Bis-L-Alanine Ester of Treprostinil 37'

The benzyl and benzyl carboxy groups were removed by catalytic hydrogenation at atmospheric pressure in the presence of palladium 10% wt on activated carbon. The 2-N-Cbz-L-alanine ester of Treprostinil benzyl ester 34' (87.4 mg, 0.13 mmoles)/bis-N-Cbz-L-alanine ester of Treprostinil benzyl ester 35' (135 mg, 0.15 mmoles) was dissolved in methanol (15 ml) and a catalytic amount of Pd/C was added. Under magnetic stirring the air was removed from the flask and hydrogen was admitted. The reaction mixture was maintained under hydrogen and stirring at room temperature for 20 hrs, then hydrogen was removed with vacuum. The reaction mixture was then filtered through a layer of celite and the solvent was removed in vacuo to afford the pure 2-L-valine ester of Treprostinil 36' (57 mg, 0.12 mmoles)/bis-L-alanine ester of Treprostinil 37' (82 mg, 0.15 mmoles).

Synthesis of Benzyl Esters of Treprostinil 38 a-e

1 

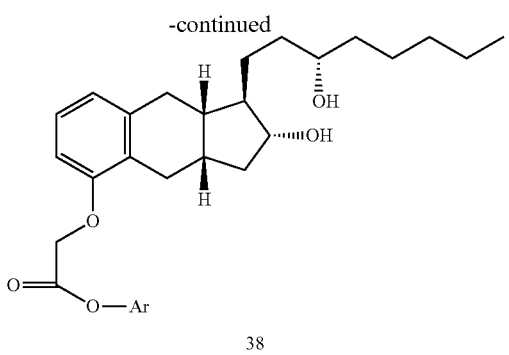

38 a 4-NO$_2$C$_6$H$_4$CH$_2$; b 4-(CH$_3$O)C$_6$H$_4$CH$_2$; c 2-ClC$_6$H$_4$CH$_2$; d 2,4-(NO$_2$)$_2$C$_6$H$_3$CH$_2$; e 4-FC$_6$H$_4$CH$_2$ Synthesis of the benzyl esters of treprostinil 38 a-e was performed using the procedure for the benzyl ester 13.

Enantiomers of these compounds, shown below, can be synthesized using reagents and synthons of enantiomeric chirality of the above reagents.

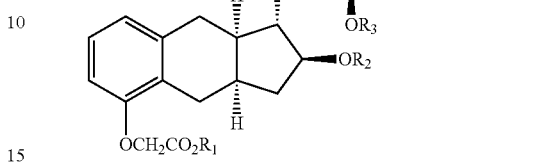

(−)-treprostinil can be synthesized as follows:

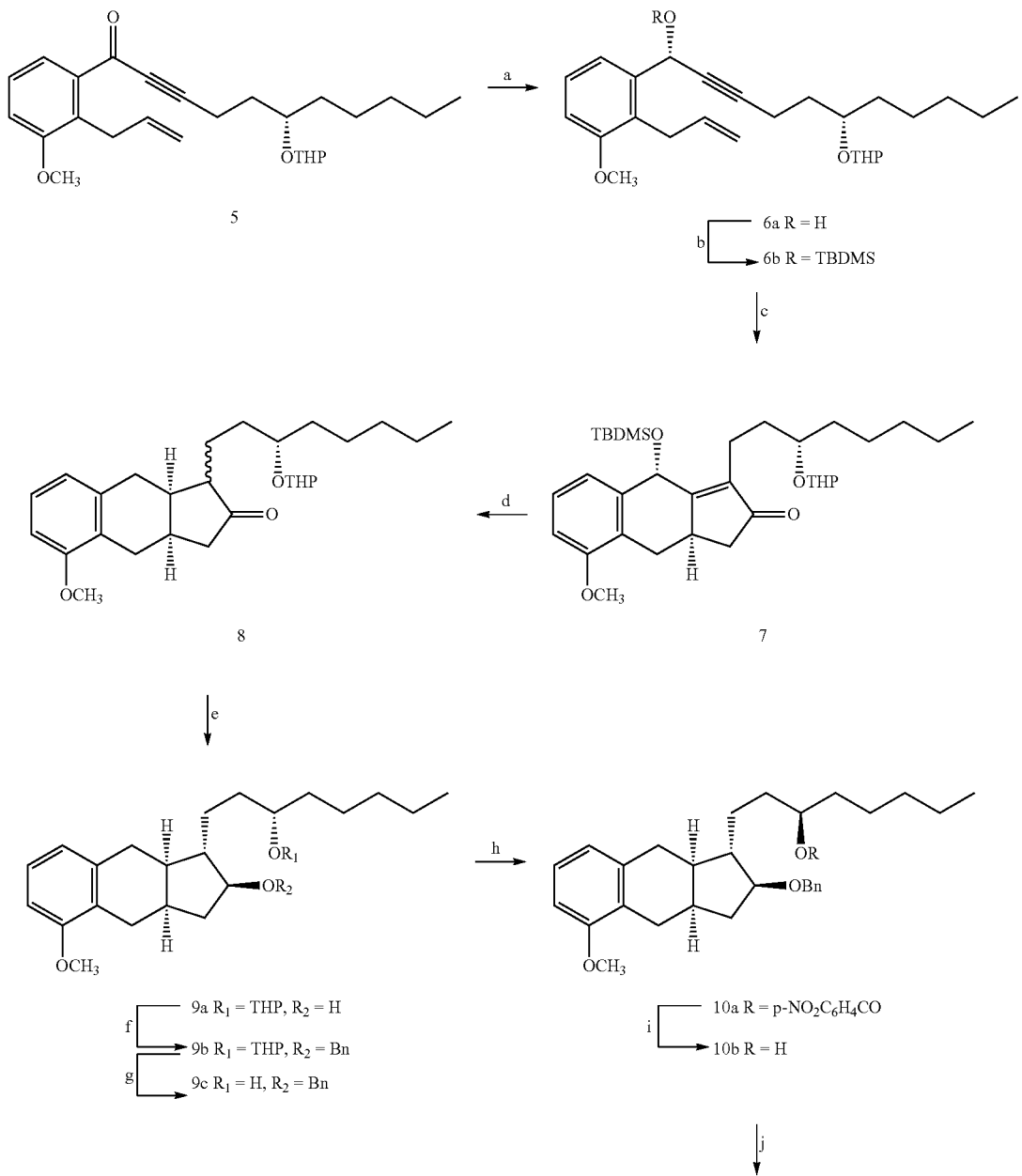

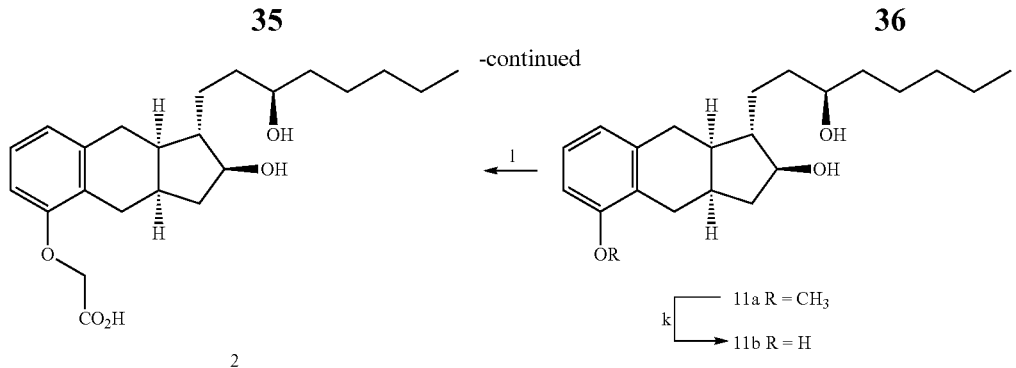

(a) (S)-2-methyl-CBS-oxazaborolidine, $BH_3.SMe_2$, THF, −30° C., 85%. (b) TBDMSCl, imidazole, $CH_2Cl_2$, 95%. (c) $Co_2(CO)_8$, $CH_2Cl_2$, 2 hr. r.t., then $CH_3CN$, 2 hr. reflux. 98%. (d) $K_2CO_3$, Pd/C (10%), EtOH, 50 psi/24 hr. 78% (e) NaOH, EtOH, $NaBH_4$. 95%. (f) BnBr, NaH, THF, 98%. (g) $CH_3OH$, TsOH. 96%. (h) i. p-nitrobenzoic acid, DEAD, TPP, benzene. (i) $CH_3OH$, KOH. 94%. (j) Pd/C (10%), EtOH, 50 psi/2 hr. quant. (k). $Ph_2PLi$, THF. (l) i. $ClCH_2CN$, $K_2CO_3$. ii, KOH, $CH_3OH$, reflux. 83% (2 steps).

Briefly, the enantiomer of the commercial drug (+)-Treprostinil was synthesized using the stereoselective intramolecular Pauson Khand reaction as a key step and Mitsunobu inversion of the side-chain hydroxyl group. The absolute configuration of (−)-Treprostinil was confirmed by an X-ray structure of the L-valine amide derivative.

The following procedure was used to make (−)-treprostinil-methyl-L-valine amide: To a stirred solution of (−)-Treprostinil (391 mg, 1 mmol) and L-valine methyl ester hydrochloride (184 mg, 1.1 mmol) in DMF (10 ml) under Ar was sequentially added pyBOP reagent (1.04 g, 2 mmol), diisopropylethyl amine (0.52 ml, 3 mmol). The reaction mixture was stirred at room temperature overnight (15 hrs). Removal of the solvent in vacuo and purification by chromatography yielded white solid 12 (481 mg, 86%), which was recrystallized (10% ethyl acetate in hexane) to give suitable crystals for X-ray.

Various modifications of these synthetic schemes capable of producing additional compounds discussed herein will be readily apparent to one skilled in the art.

There are two major barriers to deliver treprostinil in the circulatory system. One of these barriers is that treprostinil undergoes a large first pass effect. Upon first circulating through the liver, about 60% of treprostinil plasma levels are metabolized, which leaves only about 40% of the absorbed dose. Also, a major barrier to oral delivery for treprostinil is that the compound is susceptible to an efflux mechanism in the gastrointestinal tract. The permeability of treprostinil has been measured across Caco-2 cell monolayers. The apical to basal transport rate was measured to be $1.39 \times 10^6$ cm/sec, which is indicative of a highly permeable compound. However, the basal to apical transport rate was $12.3 \times 10^6$ cm/sec, which suggests that treprostinil is efficiently effluxed from the serosal to lumenal side of the epithelial cell. These data suggest that treprostinil is susceptible to p-glycoprotein, a membrane bound multidrug transporter. It is believed that the p-glycoprotein efflux pump prevents certain pharmaceutical compounds from traversing the mucosal cells of the small intestine and, therefore, from being absorbed into systemic circulation.

Accordingly, the present invention provides pharmaceutical compositions comprising treprostinil, the compound of structure I or the compound of structure II, or their pharmaceutically acceptable salts and combinations thereof in combination with one or more inhibitors of p-glycoprotein. A number of known non-cytotoxic pharmacological agents have been shown to inhibit p-glycoprotein are disclosed in U.S. Pat. Nos. 6,451,815, 6,469,022, and 6,171,786.

P-glycoprotein inhibitors include water soluble forms of vitamin E, polyethylene glycol, poloxamers including Pluronic F-68, polyethylene oxide, polyoxyethylene castor oil derivatives including Cremophor EL and Cremophor RH 40, Chrysin, (+)-Taxifolin, Naringenin, Diosmin, Quercetin, cyclosporin A (also known as cyclosporine), verapamil, tamoxifen, quinidine, phenothiazines, and 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide or a salt thereof.

Polyethylene glycols (PEGs) are liquid and solid polymers of the general formula $H(OCH_2CH_2)_nOH$, where n is greater than or equal to 4, having various average molecular weights ranging from about 200 to about 20,000. PEGs are also known as alpha-hydro-omega-hydroxypoly-(oxy-1,2-ethanediyl)polyethylene glycols. For example, PEG 200 is a polyethylene glycol wherein the average value of n is 4 and the average molecular weight is from about 190 to about 210. PEG 400 is a polyethylene glycol wherein the average value of n is between 8.2 and 9.1 and the average molecular weight is from about 380 to about 420. Likewise, PEG 600, PEG 1500 and PEG 4000 have average values of n of 12.5-13.9, 29-36 and 68-84, respectively, and average molecular weights of 570-630, 1300-1600 and 3000-3700, respectively, and PEG 1000, PEG 6000 and PEG 8000 have average molecular weights of 950-1050, 5400-6600, and 7000-9000, respectively. Polyethylene glycols of varying average molecular weight of from 200 to 20000 are well known and appreciated in the art of pharmaceutical science and are readily available.

The preferred polyethylene glycols for use in the instant invention are polyethylene glycols having an average molecular weight of from about 200 to about 20,000. The more preferred polyethylene glycols have an average molecular weight of from about 200 to about 8000. More specifically, the more preferred polyethylene glycols for use in the present invention are PEG 200, PEG 400, PEG 600, PEG 1000, PEG 1450, PEG 1500, PEG 4000, PEG 4600, and PEG 8000. The most preferred polyethylene glycols for use in the instant invention is PEG 400, PEG 1000, PEG 1450, PEG 4600 and PEG 8000.

Polysorbate 80 is an oleate ester of sorbitol and its anhydrides copolymerized with approximately 20 moles of ethylene oxide for each mole of sorbitol and sorbitol anhydrides. Polysorbate 80 is made up of sorbitan mono-9- octadecanoate poly(oxy-1,2-ethanediyl) derivatives. Polysorbate 80, also known as Tween 80, is well known and appreciated in the pharmaceutical arts and is readily available.

Water-soluble vitamin E, also known as d-alpha-tocopheryl polyethylene glycol 1000 succinate [TPGS], is a water-soluble derivative of natural-source vitamin E. TPGS may be prepared by the esterification of the acid group of crystalline d-alpha-tocopheryl acid succinate by polyethylene glycol 1000. This product is well known and appreciated in the pharmaceutical arts and is readily available. For example, a water-soluble vitamin E product is available commercially from Eastman Corporation as Vitamin E TPGS.

Naringenin is the bioflavonoid compound 2,3-dihydro-5,7-dihydroxy-2-(4-hydroxyphenyl)-4H-1-benzopyran-4-one and is also known as 4',5,7-trihydroxyflavanone. Naringenin is the aglucon of naringen which is a natural product found in the fruit and rind of grapefruit. Naringenin is readily available to the public from commercial sources.

Quercetin is the bioflavonoid compound 2-(3,4-dihydroxyphenyl)-3,5,7-trihydroxy-4H-1-benzopyran-4-one and is also known as 3,3',4',5,7-pentahydroxyflavone. Quercetin is the aglucon of quercitrin, of rutin and of other glycosides. Quercetin is readily available to the public from commercial sources.

Diosmin is the naturally occurring flavonic glycoside compound 7-[[6-O-6-deoxy-alpha-L-mannopyranosyl)-beta-D-glucopyranosyl]oxy]-5-hydroxy-2-(3-hydroxy-4-methoxyphenyl)-4H-1-benzopyran-4-one. Diosmin can be isolated from various plant sources including citrus fruits. Diosmin is readily available to the public from commercial sources.

Chrysin is the naturally occurring compound 5,7-dihydroxy-2-phenyl-4H-1-benzopyran-4-one which can be isolated from various plant sources. Chrysin is readily available to the public from commercial sources.

Poloxamers are alpha-hydro-omega-hydroxypoly(oxyethylene)poly (oxypropylene)poly(oxyethylene) block copolymers. Poloxamers are a series of closely related block copolymers of ethylene oxide and propylene oxide conforming to the general formula $HO(C_2H_4O)_a(C_3H_6O)_b(C_2H_4O)_a H$. For example, poloxamer 124 is a liquid with "a" being 12, "b" being 20, and having an average molecular weight of from about 2090 to about 2360; poloxamer 188 is a solid with "a" being 80, "b" being 27, and having an average molecular weight of from about 7680 to about 9510; poloxamer 237 is a solid with "a" being 64, "b" being 37, and having an average molecular weight of from about 6840 to about 8830; poloxamer 338 is a solid with "a" being 141, "b" being 44, and having an average molecular weight of from about 12700 to about 17400; and poloxamer 407 is a solid with "a" being 101, "b" being 56, and having an average molecular weight of from about 9840 to about 14600. Poloxamers are well known and appreciated in the pharmaceutical arts and are readily available commercially. For example, Pluronic F-68 is a commercially available poloxamer from BASF Corp. The preferred poloxamers for use in the present invention are those such as poloxamer 188, Pluronic F-68, and the like.

Polyoxyethylene castor oil derivatives are a series of materials obtained by reacting varying amounts of ethylene oxide with either castor oil or hydrogenated castor oil. These polyoxyethylene castor oil derivatives are well known and appreciated in the pharmaceutical arts and several different types of material are commercially available, including the Cremophors available from BASF Corporation. Polyoxyethylene castor oil derivatives are complex mixtures of various hydrophobic and hydrophilic components. For example, in polyoxyl 35 castor oil (also known as Cremophor EL), the hydrophobic constituents comprise about 83% of the total mixture, the main component being glycerol polyethylene glycol ricinoleate. Other hydrophobic constituents include fatty acid esters of polyethylene glycol along with some unchanged castor oil. The hydrophilic part of polyoxyl 35 castor oil (17%) consists of polyethylene glycols and glyceryl ethoxylates.

In polyoxyl 40 hydrogenated castor oil (Cremophor RH 40) approximately 75% of the components of the mixture are hydrophobic. These comprise mainly fatty acid esters of glycerol polyethylene glycol and fatty acid esters of polyethylene glycol. The hydrophilic portion consists of polyethylene glycols and glycerol ethoxylates. The preferred polyoxyethylene castor oil derivatives for use in the present invention are polyoxyl 35 castor oil, such as Cremophor EL, and polyoxyl 40 hydrogenated castor oil, such as Cremophor RH 40. Cremophor EL and Cremophor RH 40 are commercially available from BASF Corporation.

Polyethylene oxide is a nonionic homopolymer of ethylene oxide conforming to the general formula $(OCH_2CH_2)_n$ in which n represents the average number of oxyethylene groups. Polyethylene oxides are available in various grades which are well known and appreciated by those in the pharmaceutical arts and several different types of material are commercially available. The preferred grade of polyethylene oxide is NF and the like which are commercially available.

(+)-Taxifolin is (2R-trans)-2-(3,4-dihydroxyphenyl)-2,3-dihydro-3,5,7-trihydroxy-4H-1-benzo pyran-4-one. Other common names for (+)-taxifolin are (+)-dihydroquercetin; 3,3',4',5,7-pentahydroxy-flavanone; diquertin; taxifoliol; and distylin. (+)-Taxifolin is well know and appreciated in the art of pharmaceutical arts and is readily available commercially.

The preferred p-glycoprotein inhibitor for use in the present invention are water soluble vitamin E, such as vitamin E TPGS, and the polyethylene glycols. Of the polyethylene glycols, the most preferred p-glycoprotein inhibitors are PEG 400, PEG 1000, PEG 1450, PEG 4600 and PEG 8000.

Administration of a p-glycoprotein inhibitor may be by any route by which the p-glycoprotein inhibitor will be bioavailable in effective amounts including oral and parenteral routes. Although oral administration is preferred, the p-glycoprotein inhibitors may also be administered intravenously, topically, subcutaneously, intranasally, rectally, intramuscularly, or by other parenteral routes. When administered orally, the p-glycoprotein inhibitor may be administered in any convenient dosage form including, for example, capsule, tablet, liquid, suspension, and the like.

Generally, an effective p-glycoprotein inhibiting amount of a p-glycoprotein inhibitor is that amount which is effective in providing inhibition of the activity of the p-glycoprotein mediated active transport system present in the gut. An effective p-glycoprotein inhibiting amount can vary between about 5 mg to about 1000 mg of p-glycoprotein inhibitor as a daily dose depending upon the particular p-glycoprotein inhibitor selected, the species of patient to be treated, the dosage regimen, and other factors which are all well within the abilities of one of ordinary skill in the medical arts to evaluate and assess. A preferred amount however will typically be from about 50 mg to about 500 mg, and a more preferred amount will typically be from about 100 mg to about 500 mg. The above amounts of a p-glycoprotein inhibitor can be administered from once to multiple times per day. Typically for oral dosing, doses will be administered on a regimen requiring one, two or three doses per day.

Where water soluble vitamin E or a polyethylene glycol is selected as the p-glycoprotein inhibitor, a preferred amount will typically be from about 5 mg to about 1000 mg, a more preferred amount will typically be from about 50 mg to about 500 mg, and a further preferred amount will typically be from about 100 mg to about 500 mg. The most preferred amount of water soluble vitamin E or a polyethylene glycol will be from about 200 mg to about 500 mg. The above amounts of water soluble vitamin E or polyethylene glycol can be administered from once to multiple times per day. Typically, doses will be administered on a regimen requiring one, two or three doses per day with one and two being preferred.

As used herein, the term "co-administration" refers to administration to a patient of both a compound that has vasodilating and/or platelet aggregation inhibiting properties, including the compounds described in U.S. Pat. Nos. 4,306,075 and 5,153,222 which include treprostinil and structures I and II described herein, and a p-glycoprotein inhibitor so that the pharmacologic effect of the p-glycoprotein inhibitor in inhibiting p-glycoprotein mediated transport in the gut is manifest at the time at which the compound is being absorbed from the gut. Of course, the compound and the p-glycoprotein inhibitor may be administered at different times or concurrently. For example, the p-glycoprotein inhibitor may be administered to the patient at a time prior to administration of the therapeutic compound so as to pre-treat the patient in preparation for dosing with the vasodilating compound. Furthermore, it may be convenient for a patient to be pre-treated with the p-glycoprotein inhibitor so as to achieve steady state levels of p-glycoprotein inhibitor prior to administration of the first dose of the therapeutic compound. It is also contemplated that the vasodilating and/or platelet aggregation inhibiting compounds and the p-glycoprotein inhibitor may be administered essentially concurrently either in separate dosage forms or in the same oral dosage form.

The present invention further provides that the vasodilating and/or platelet aggregation inhibiting compound and the p-glycoprotein inhibitor may be administered in separate dosage forms or in the same combination oral dosage form. Co-administration of the compound and the p-glycoprotein inhibitor may conveniently be accomplished by oral administration of a combination dosage form containing both the compound and the p-glycoprotein inhibitor.

Thus, an additional embodiment of the present invention is a combination pharmaceutical composition for oral administration comprising an effective vasodilating and/or platelet aggregation inhibiting amount of a compound described herein and an effective p-glycoprotein inhibiting amount of a p-glycoprotein inhibitor. This combination oral dosage form may provide for immediate release of both the vasodilating and/or platelet aggregation inhibiting compound and the p-glycoprotein inhibitor or may provide for sustained release of one or both of the vasodilating and/or platelet aggregation inhibiting compound and the p-glycoprotein inhibitor. One skilled in the art would readily be able to determine the appropriate properties of the combination dosage form so as to achieve the desired effect of co-administration of the vasodilating and/or platelet aggregation inhibiting compound and the p-glycoprotein inhibitor.

Accordingly, the present invention provides for an enhancement of the bioavailability of treprostinil, a drug of structure I or II, and pharmaceutically acceptable salts thereof by co-administration of a p-glycoprotein inhibitor. By co-administration of these compounds and a p-glycoprotein inhibitor, the total amount of the compound can be increased over that which would otherwise circulate in the blood in the absence of the p-glycoprotein inhibitor. Thus, co-administration in accordance with the present invention can cause an increase in the AUC of the present compounds over that seen with administration of the compounds alone.

Typically, bioavailability is assessed by measuring the drug concentration in the blood at various points of time after administration of the drug and then integrating the values obtained over time to yield the total amount of drug circulating in the blood. This measurement, called the Area Under the Curve (AUC), is a direct measurement of the bioavailability of the drug.

Without limiting the scope of the invention, it is believed that in some embodiments derivatizing treprostinil at the $R^2$ and $R^3$ hydroxyl groups can help overcome the barriers to oral treprostinil delivery by blocking these sites, and thus the metabolism rate may be reduced to permit the compound to bypass some of the first pass effect. Also, with an exposed amino acid, the prodrug may be actively absorbed from the dipeptide transporter system that exists in the gastrointestinal tract. Accordingly, the present invention provides compounds, such as those found in structures I and II, that reduce the first pass effect of treprostinil and/or reduce the efflux mechanism of the gastrointestinal tract.

In some embodiments of the method of treating hypertension in a subject, the subject is a mammal, and in some embodiments is a human.

Pharmaceutical formulations may include any of the compounds of any of the embodiments described above, either alone or in combination, in combination with a pharmaceutically acceptable carrier such as those described herein.

The instant invention also provides for compositions which may be prepared by mixing one or more compounds of the instant invention, or pharmaceutically acceptable salts thereof, with pharmaceutically acceptable carriers, excipients, binders, diluents or the like, to treat or ameliorate a variety of disorders related vasoconstriction and/or platelet aggregation. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, transdermal or subcutaneous administration as well as intrathecal, intravenous, intramuscular, intraperitoneal, intranasal, intraocular or intraventricular injection. The compound or compounds of the instant invention can also be administered by any of the above routes, for example in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Additionally, tests have shown that the present compounds, including treprostinil, and in particular the compounds of structure I and II have increased bioavailability when delivered to the duodenum. Accordingly, one embodiment of the present invention involves preferential delivery of the desired compound to the duodenum as well as pharmaceutical formulations that achieve duodenal delivery. Duodenal administration can be achieved by any means known in the art. In one of these embodiments, the present compounds can be formulated in an enteric-coated dosage form. Generally, enteric-coated dosage forms are usually coated with a polymer that is not soluble at low pH, but dissolves quickly when exposed to pH conditions of 3 or above. This delivery form takes advantage of the difference in pH between the stomach, which is about 1 to 2, and the duodenum, where the pH tends to be greater than 4.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

A method of preparing pharmaceutical formulations includes mixing any of the above-described compounds with a pharmaceutically acceptable carrier and water or an aqueous solution.

Pharmaceutical formulations and medicaments according to the invention include any of the compounds of any of the embodiments of compound of structure I, II or pharmaceutically acceptable salts thereof described above in combination with a pharmaceutically acceptable carrier. Thus, the compounds of the invention may be used to prepare medicaments and pharmaceutical formulations. In some such embodiments, the medicaments and pharmaceutical formulations comprise any of the compounds of any of the embodiments of the compounds of structure I or pharmaceutically acceptable salts thereof. The invention also provides for the use of any of the compounds of any of the embodiments of the compounds of structure I, II or pharmaceutically acceptable salts thereof for prostacyclin-like effects. The invention also provides for the use of any of the compounds of any of the embodiments of the compounds of structure I, II or pharmaceutically acceptable salts thereof or for the treatment of pulmonary hypertension.

The invention also pertains to kits comprising one or more of the compounds of structure I or II along with instructions for use of the compounds. In another embodiment, kits having compounds with prostacyclin-like effects described herein in combination with one or more p-glycoprotein inhibitors is provided along with instructions for using the kit.

By way of illustration, a kit of the invention may include one or more tablets, capsules, caplets, gelcaps or liquid formulations containing the bioenhancer of the present invention, and one or more tablets, capsules, caplets, gelcaps or liquid formulations containing a prostacyclin-like effect compound described herein in dosage amounts within the ranges described above. Such kits may be used in hospitals, clinics, physician's offices or in patients' homes to facilitate the co-administration of the enhancing and target agents. The kits should also include as an insert printed dosing information for the co-administration of the enhancing and target agents.

The following abbreviations and definitions are used throughout this application:

Generally, reference to a certain element such as hydrogen or H is meant to include all isotopes of that element. For example, if an R group is defined to include hydrogen or H, it also includes deuterium and tritium.

As used herein, the term "p-glycoprotein inhibitor" refers to organic compounds which inhibit the activity of the p-glycoprotein mediated active transport system present in the gut. This transport system actively transports drugs which have been absorbed from the intestinal lumen and into the gut epithelium back out into the lumen. Inhibition of this p-glycoprotein mediated active transport system will cause less drug to be transported back into the lumen and will thus increase the net drug transport across the gut epithelium and will increase the amount of drug ultimately available in the blood.

The phrases "oral bioavailability" and "bioavailability upon oral administration" as used herein refer to the systemic availability (i.e., blood/plasma levels) of a given amount of drug administered orally to a patient.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; and oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted arylalkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted arylalkyl group (i.e., a benzyl group). Thus the phrase includes, but is not limited to, groups such as benzyl, diphenylmethyl, and 1-phenylethyl (—CH(C$_6$H$_5$)(CH$_3$)) among others.

The phrase "substituted arylalkyl" has the same meaning with respect to unsubstituted arylalkyl groups that substituted aryl groups had with respect to unsubstituted aryl groups. However, a substituted arylalkyl group also includes groups in which a carbon or hydrogen bond of the alkyl part of the group is replaced by a bond to a non-carbon or a non-hydrogen atom. Examples of substituted arylalkyl groups include, but are not limited to, —CH$_2$C(=O)(C$_6$H$_5$), and —CH$_2$(2-methylphenyl) among others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

"Treating" within the context of the instant invention, means an alleviation of symptoms associated with a biological condition, disorder, or disease, or halt of further progression or worsening of those symptoms, or prevention or prophylaxis of the disease or disorder. For example, within the context of treating patients having pulmonary hypertension, successful treatment may include a reduction direct vasodilation of pulmonary and/or systemic arterial vascular beds and inhibition of platelet aggregation. The result of this vasodilation will generally reduce right and left ventricular afterload and increased cardiac output and stroke volume. Dose-related negative inotropic and lusitropic effects can also result. The outward manifestation of these physical effects can include a decrease in the symptoms of hypertension, such as shortness of breath, and an increase in exercise capacity.

The present invention, thus generally described, will be understood more readily by reference to the following examples, which are provided by way of illustration and are not intended to be limiting of the present invention.

EXAMPLES

Example 1

In this Example, the bioavailability of treprostinil in rats after dosing orally, intraduodenally, intracolonically and via the portal vein was compared to determine possible barriers to bioavailability. In addition to bioavailability, a number of pharmacokinetic parameters were determined.

Animal Dosing

The bioavailability of treprostinil was evaluated in Sprague-Dawley, male rats. Fifteen surgically modified rats were purchased from Hilltop Lab Animals (Scottdale, Pa.). The animals were shipped from Hilltop to Absorption Systems' West Chester University facility (West Chester, Pa.), where they were housed for at least twenty-four hours prior to being used in the study. The animals were fasted for approximately 16 hours prior to dosing. The fifteen rats used in this study were divided into five groups (I, II, III, IV and V).

The weight of the animals and the dosing regimen are presented in Table 1.

TABLE 1

| Group | Rat # | Weight (g) | Route of Administration | Study Day | Dose Volume (mL/kg) | Dose (mg/kg) |
|---|---|---|---|---|---|---|
| I | 118 | 327 | Intravenous | 0 | 2 | 1 |
|  | 119 | 329 | Intravenous | 0 | 2 | 1 |
|  | 120 | 320 | Intravenous | 0 | 2 | 1 |
| II | 121 | 337 | Intraportal Vein | 0 | 2 | 1 |
|  | 122 | 319 | Intraportal Vein | 0 | 2 | 1 |
|  | 123 | 330 | Intraportal Vein | 0 | 2 | 1 |
| III | 124 | 329 | Intraduodenal | 0 | 2 | 1 |
|  | 125 | 331 | Intraduodenal | 0 | 2 | 1 |
|  | 126 | 324 | Intraduodenal | 0 | 2 | 1 |
| IV | 127 | 339 | Intracolonic | 0 | 2 | 1 |
|  | 128 | 333 | Intracolonic | 0 | 2 | 1 |
|  | 129 | 320 | Intracolonic | 0 | 2 | 1 |
| V | 130 | 293 | Oral | 0 | 2 | 1 |
|  | 131 | 323 | Oral | 0 | 2 | 1 |
|  | 132 | 332 | Oral | 0 | 2 | 1 |

Samples were withdrawn at the following time points.
IV and IPV: 0 (pre-dose) 2, 5, 15, 30, 60, 120, 240, 360, 480 minutes
ID, IC and Oral: 0 (pre-dose), 5, 15, 30, 60, 120, 240, 360, 480 minutes Approximately 0.50 to 0.75 mL of whole blood was collected from the jugular vein of a cannulated rat. The blood was transferred to heparinized tubes and placed on ice until centrifuged. Following centrifugation the plasma was placed on ice until frozen at −70°C prior to shipment to Absorption Systems Analysis of Plasma Samples Samples were analyzed using the following methodology:
Dosing Solution Preparation The dosing solution was prepared by combining 15.2 mg of treprostinil diethanolamine (12.0 mg of the free acid form) with 24 mL of 5% dextrose. The solution was then sonicated until dissolved for a final concentration of 0.5 mg/mL. The final pH of the dosing solution was 4.6. At the time of dosing, the dosing solution was clear and homogenous.

Standards and Sample Preparation

To determine the concentration of treprostinil in rat plasma samples, standards were prepared with rat plasma collected in heparin obtained from Lampire Biological Laboratories (Lot #021335263) to contain 1000, 300, 100, 30, 10, 3, 1 and 0.3 ng/mL of treprostinil. Plasma standards were treated identically to the plasma samples.

Plasma samples were prepared by solid phase extraction. After an extraction plate was equilibrated, 150 μL of a plasma sample was placed into the well and vacuumed through. The extraction bed was then washed with 600 μL of acetonitrile:deionized water (25:75) with 0.2% formic acid. The compound was eluted with 600 μL of 90% acetonitrile and 10% ammonium acetate. The eluates were collected and evaporated to dryness. The residue was reconstituted with 150 μL of acetonitrile:deionized water (50:50) with 0.5 μg/mL of tolbutamide (used as an internal standard).

HPLC Conditions

Column: Keystone Hypersil BDS C18 30×2 mm i.d., 3 μm.

Mobile Phase Buffer: 25 mM $NH_4OH$ to pH 3.5 w/85% formic acid.

Reservoir A: 10% buffer and 90% water.
Reservoir B: 10% buffer and 90% acetonitrile.
Mobile Phase Composition:
Gradient Program:

| Time | Duration | Grad. Curve | % A | % B |
|---|---|---|---|---|
| −0.1 | 0.10 | 0 | 80 | 20 |
| 0 | 3.00 | 1.0 | 10 | 90 |
| 3.00 | 1.00 | 1.0 | 0 | 100 |
| 4.00 | 2.00 | 0 | 80 | 20 |

Flow Rate: 300 μL/min.
Inj. Vol.: 10 μL
Run Time: 6.0 min.
Retention Time: 2.6 min.
Mass Spectrometer
Instrument: PE SCIEX API 2000
Interface: Electrospray ("Turbo Ion Spray")
Mode: Multiple Reaction Monitoring (MRM)

|  | Precursor Ion | Product Ion |
|---|---|---|
| Treprostinil | 389.2 | 331.2 |
| IS | 269.0 | 170.0 |

| Nebulizing Gas: 25 | Drying Gas: 60, 350° C. | Curtain Gas: 25 | Ion Spray: −5000 V | |
|---|---|---|---|---|
| Orifice: −80 V | Ring: −350 V | Q0: 10 V | IQ1: 11 V | ST: 15 V |
| R01: 11 V | IQ2: 35 V | R02: 40 V | IQ3: 55 V | R03: 45 V |
| CAD Gas: 4 | | | | |

Method Validation

Table 2 lists the average recoveries (n=6) and coefficient of variation (c.v.) for rat plasma spiked with treprostinil. All samples were compared to a standard curve prepared in 50:50 dH$_2$O:acetonitrile with 0.5 μg/mL of tolbutamide to determine the percent of treprostinil recovered from the plasma.

TABLE 2

Accuracy and Precision of Method

| Spiked Concentration | Percent Recovered | Coefficient of Variation |
|---|---|---|
| 1000 ng/mL | 85.6 | 5.2 |
| 100 ng/mL | 89.6 | 11.6 |
| 10 ng/mL | 98.8 | 7.0 |

Pharmacokinetic Analysis

Pharmacokinetic analysis was performed on the average plasma concentration for each time point.

The data were subjected to non-compartmental analysis using the pharmacokinetic program WinNonlin v. 3.1 (2).

Results

Clinical Observations

Prior to beginning the experiments it was noted that supra-pharmacological doses of treprostinil would be needed to achieve plasma concentrations that could be analyzed with adequate sensitivity. Using the dose of 1 mg/kg some adverse effects were noted in animals dosed intravenously and via the intraportal vein.

All rats dosed intravenously displayed signs of extreme lethargy five minutes after dosing but fully recovered to normal activity thirty minutes post-dosing. In addition, fifteen minutes after dosing all three animals dosed via the portal vein exhibited signs of lethargy. One rat (#123) expired before the thirty-minute sample was drawn. The other rats fully recovered. The remaining animals did not display any adverse reactions after administration of the compound.

Sample Analysis

Average plasma concentrations for each route of administration are shown in Table 3.

TABLE 3

| | Average (n = 3) plasma concentrations (ng/mL) | | | | | | | | |
|---|---|---|---|---|---|---|---|---|---|
| | | | | | Time (mm) | | | | |
| | Pre-dose | 2 | 5 | 15 | 30 | 60 | 120 | 240 | 360 | 480 |
| Intravenous | 0 | 1047.96 | 364.28 | 130.91 | 55.56 | 14.45 | 4.45 | 1.09 | 0.50 | 0.30 |
| Intraportal Vein* | 0 | 302.28 | 97.39 | 47.98 | 21.94 | 11.06 | 3.87 | 2.51 | 4.95 | 5.14 |
| Intraduodenal | 0 | — | 61.76 | 31.67 | 18.57 | 13.55 | 5.91 | 1.11 | 0.89 | 0.90 |
| Intracolonic | 0 | — | 7.46 | 3.43 | 3.52 | 1.48 | 0.64 | 0.36 | 0.06$^\lambda$ | 0.20$^\lambda$ |
| Oral | 0 | — | 4.52 | 2.90 | 3.67 | 2.06 | 4.52 | 1.82 | 0.90 | 0.96 |

Figure 1B:
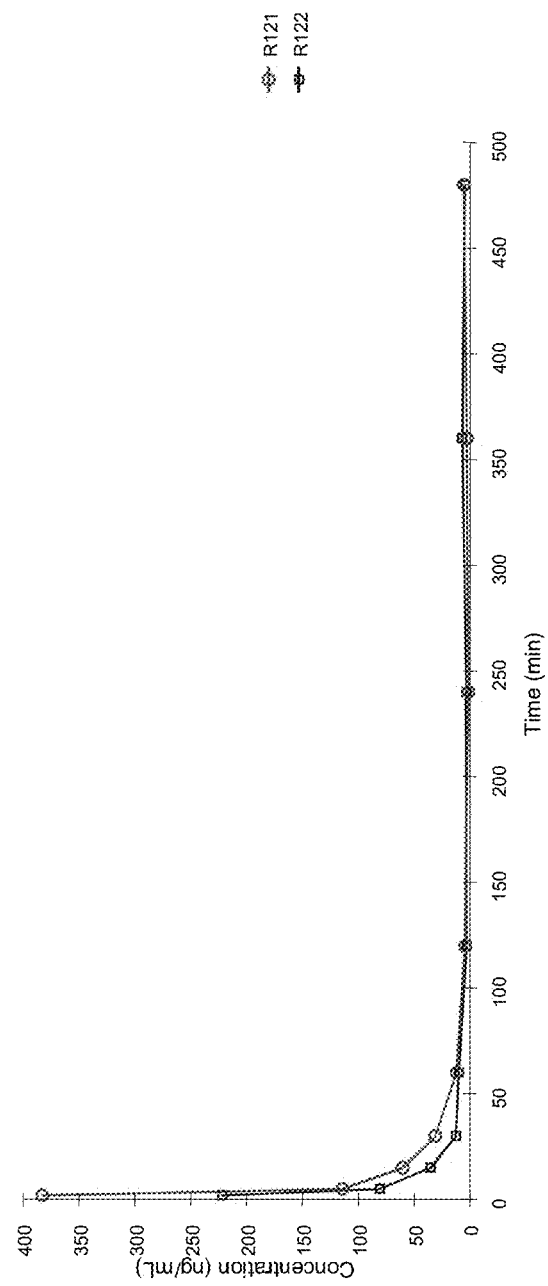
Figure 2A:
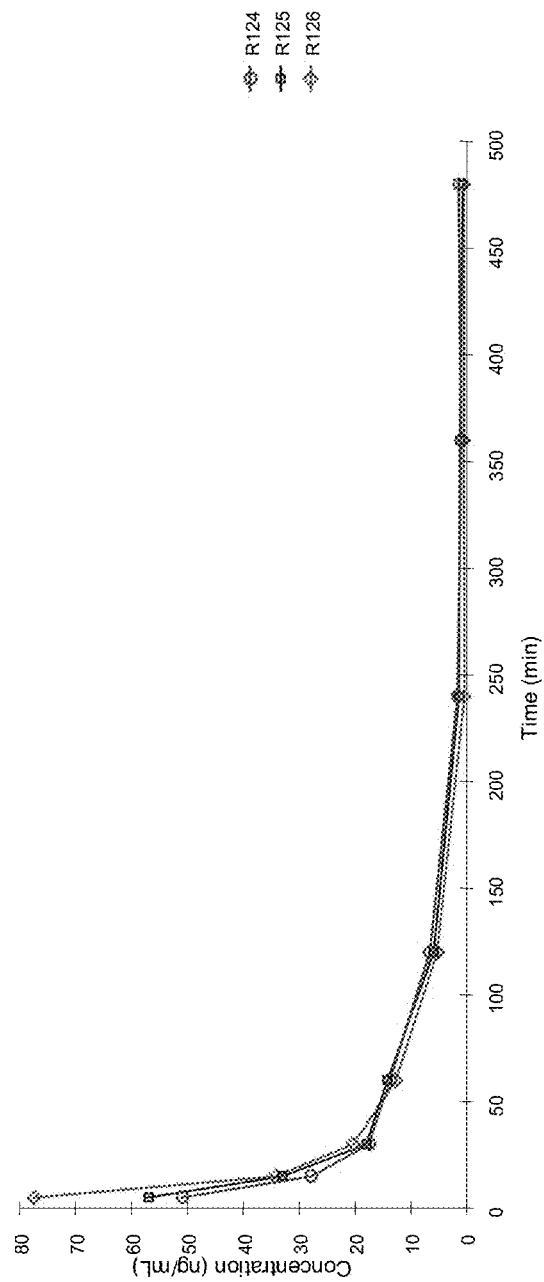
FIGS. 2A, 2B and 2C respectively show plasma concentration versus time curves for intraduodenal, intracolonic and oral dosing of treprostinil diethanol amine salt in rats as described in Example 1.
Figure 2B:
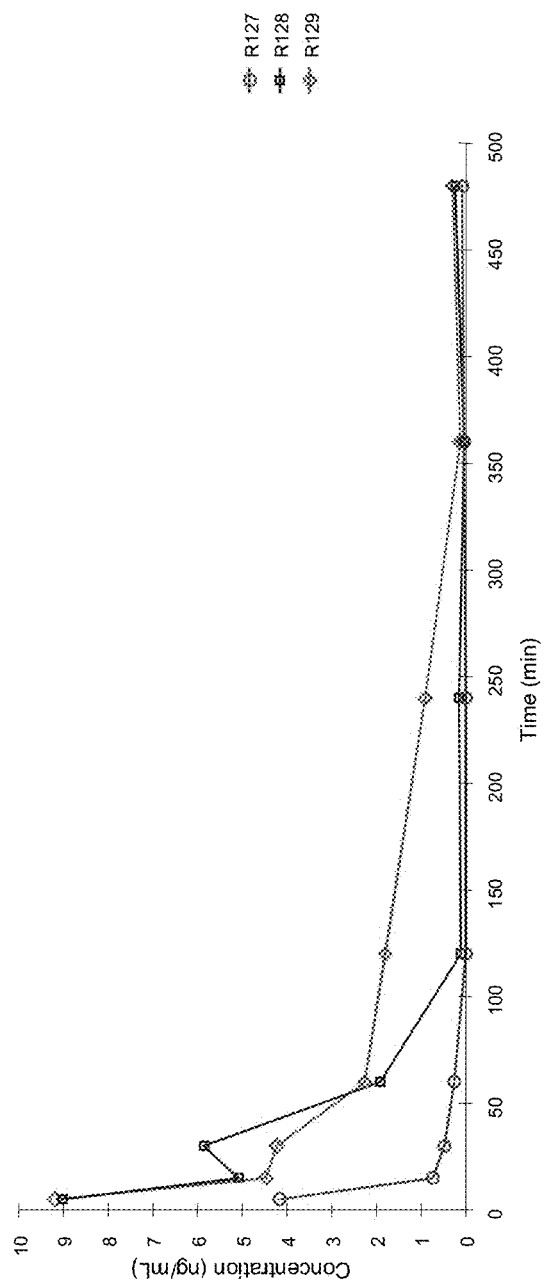
Figure 2C:
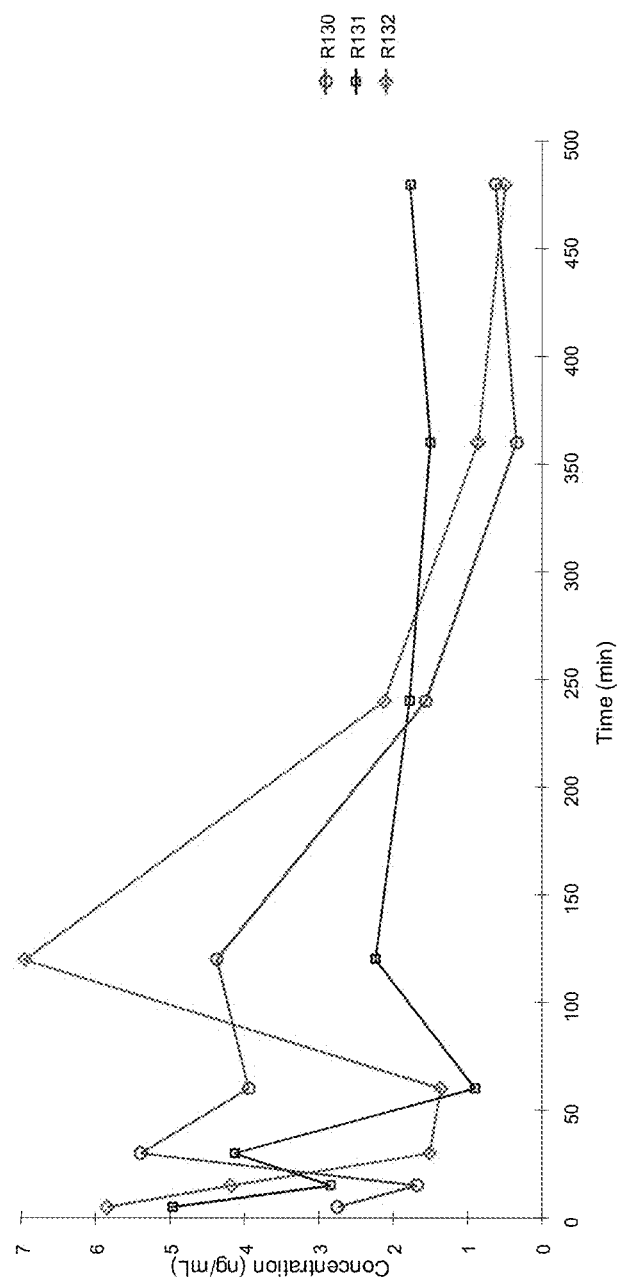
Figure 3:
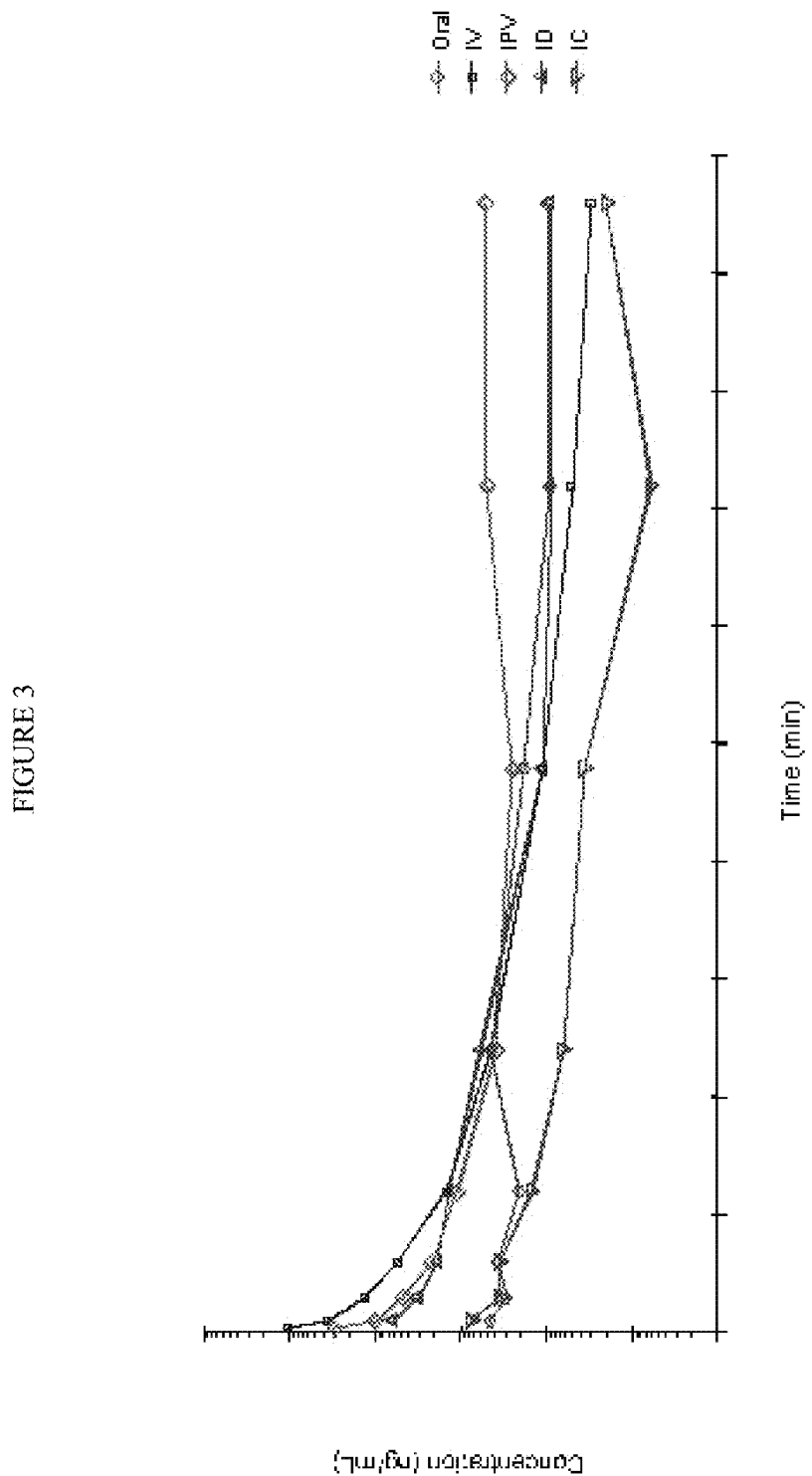
FIG. 3 shows on a logarithmic scale the average plasma concentration versus time curves for the routes of administration described in Example 1.
Figure 4:
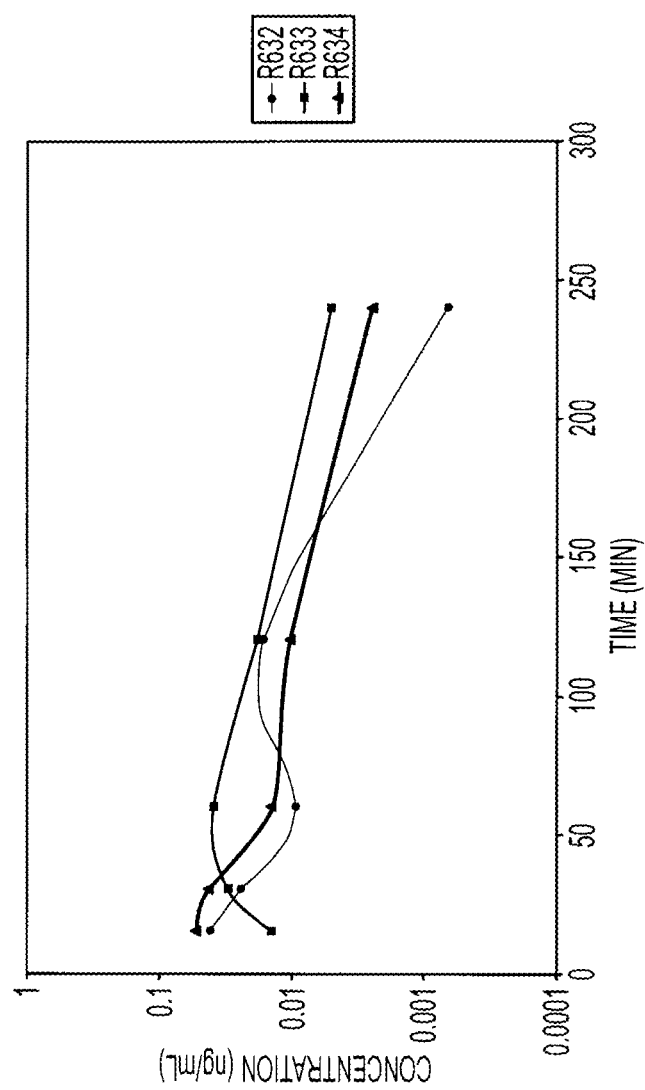
FIG. 4 is a graphical representation of the plasma concentration versus time curve for treprostinil in rat following oral administration in rats of treprostinil methyl ester as described in Example 2.
Figure 5:
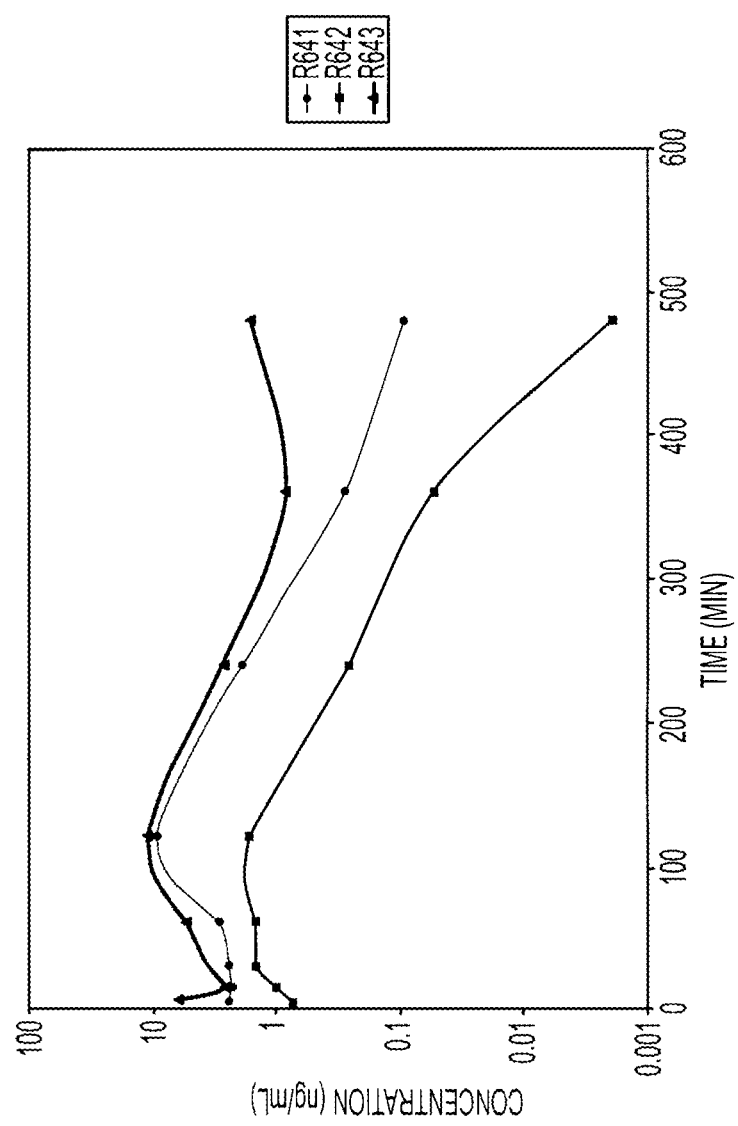
FIG. 5 is a graphical representation of the plasma concentration versus time curve for treprostinil in rat following oral administration in rats of treprostinil benzyl ester as described in Example 2.
Figure 6:
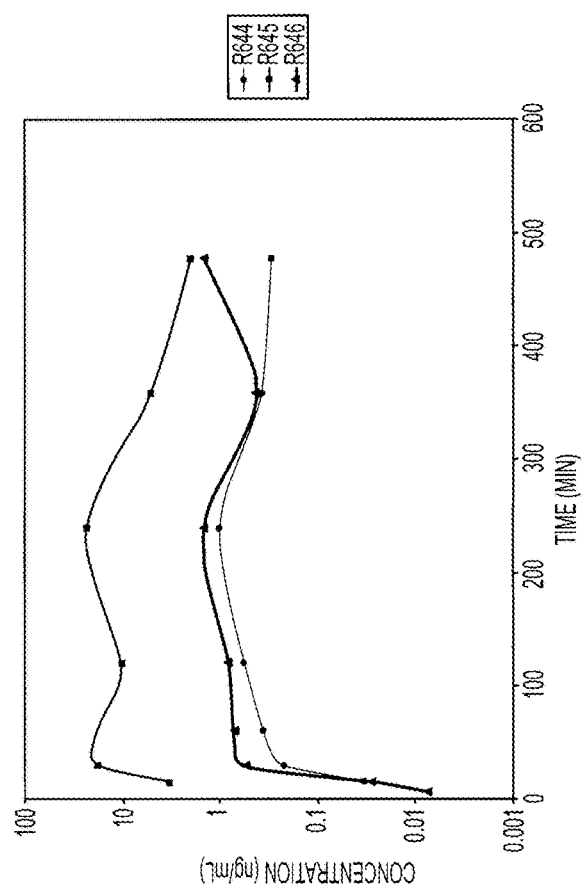
FIG. 6 is a graphical representation of the plasma concentration versus time curve for treprostinil in rat following oral administration in rats of treprostinil diglycine as described in Example 2.
Figure 7:
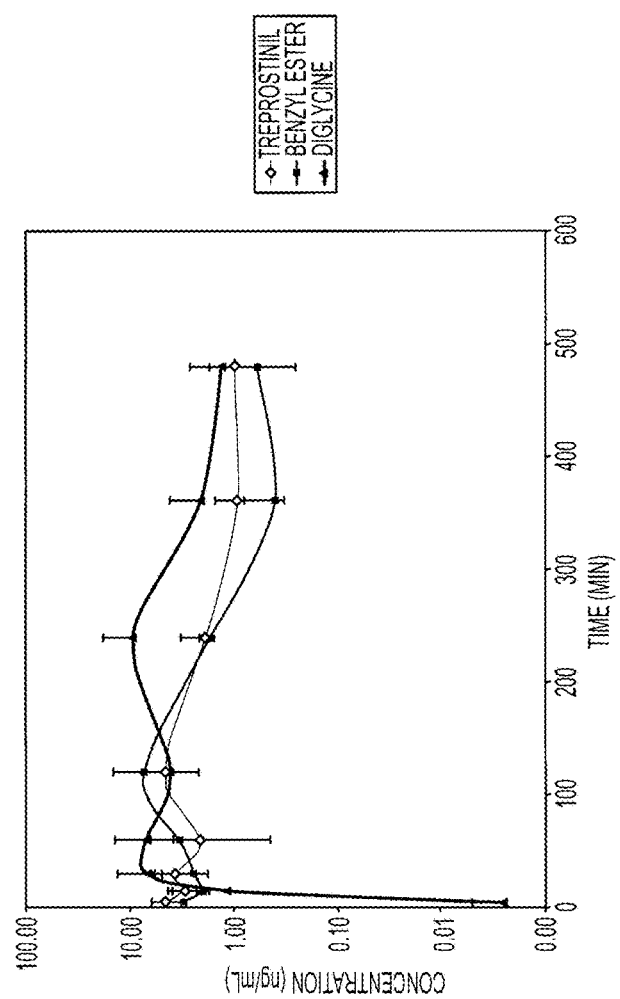
FIG. 7 is a graphical representation of the plasma concentration versus time curve for treprostinil in rat following oral administration in rates of treprostinil benzyl ester (0.5 mg/kg) and treprostinil diglycine (0.5 mg/kg) as described in Example 2 compared to treprostinil (1 mg/per kg).
Figure 8:
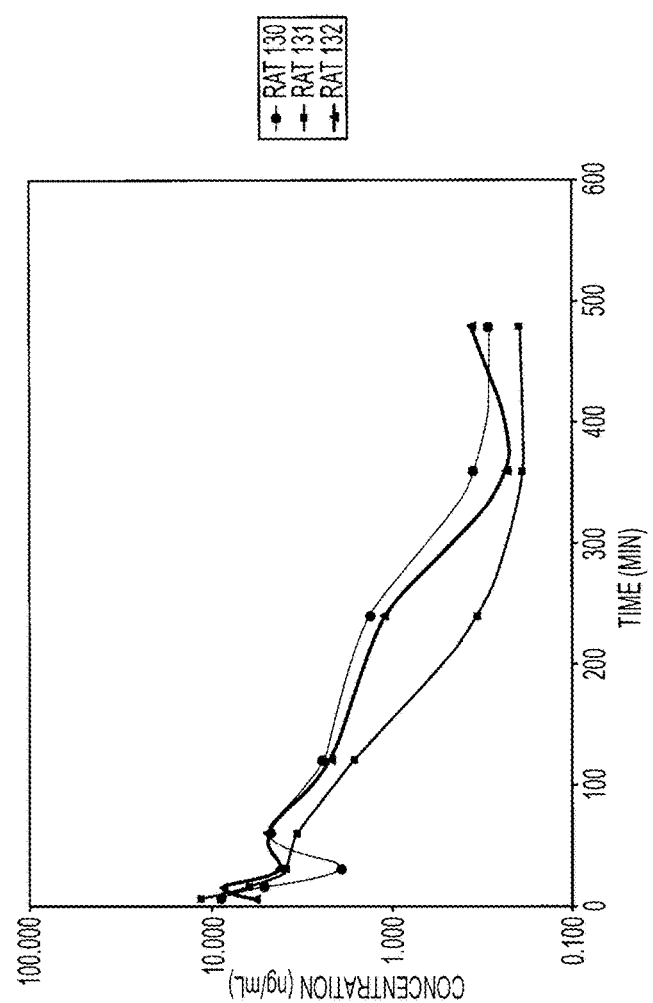
FIG. 8 is a graphical representation of the plasma concentration versus time curve for treprostinil in rat following intraduodenal administration of treprostinil monophosphate (ring) as described in Example 3.
Figure 9:
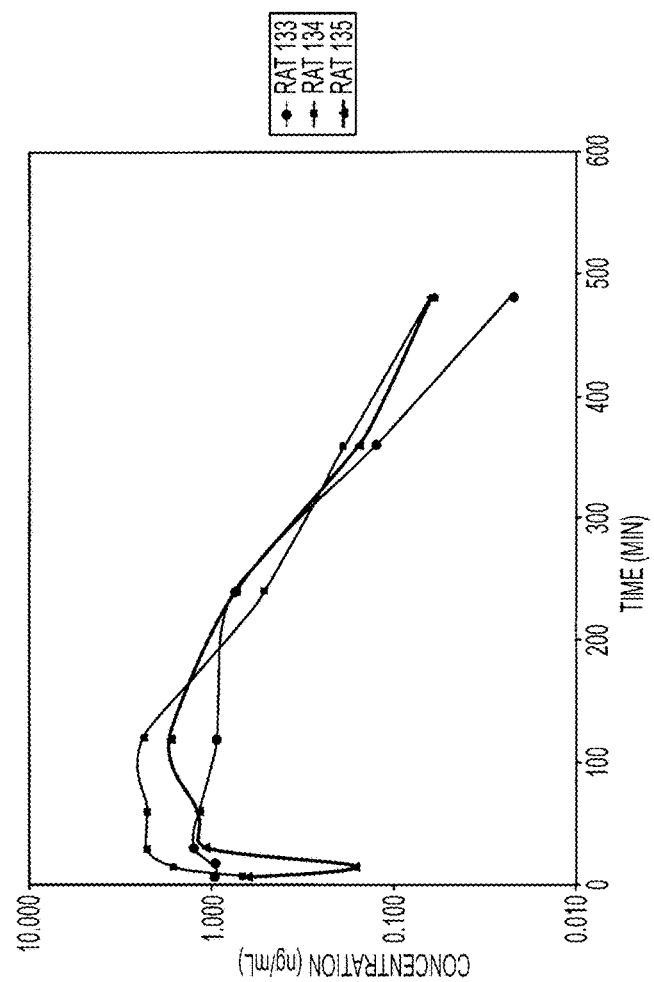
FIG. 9 is a graphical representation of the plasma concentration versus time curve for treprostinil in rat following intraduodenal administration of treprostinil monovaline (ring) as described in Example 3.
Figure 10:
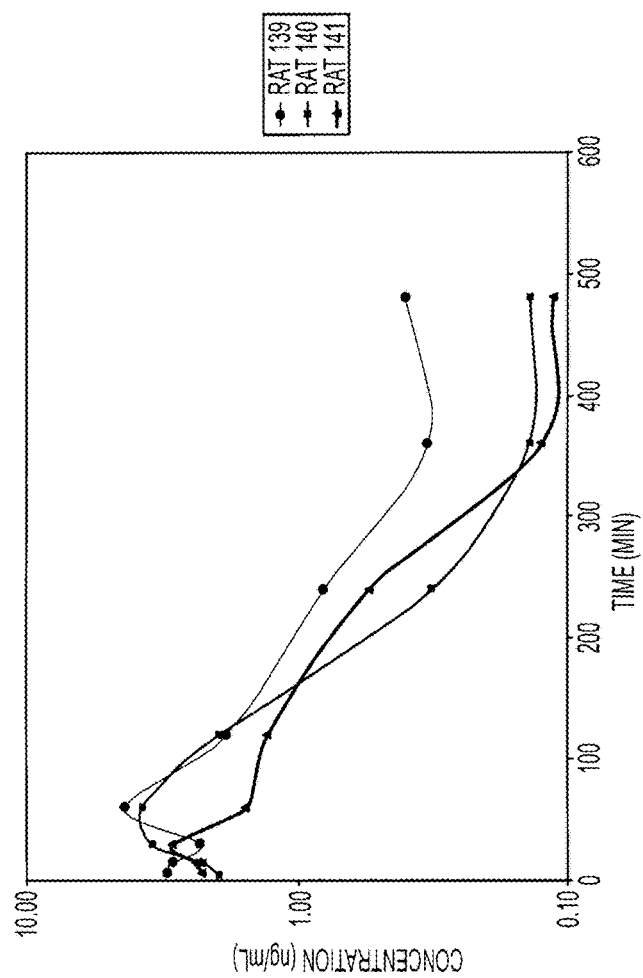
FIG. 10 is a graphical representation of the plasma concentration versus time curve for treprostinil in rat following intraduodenal administration of treprostinil monoalanine (ring) as described in Example 3.
Figure 11:
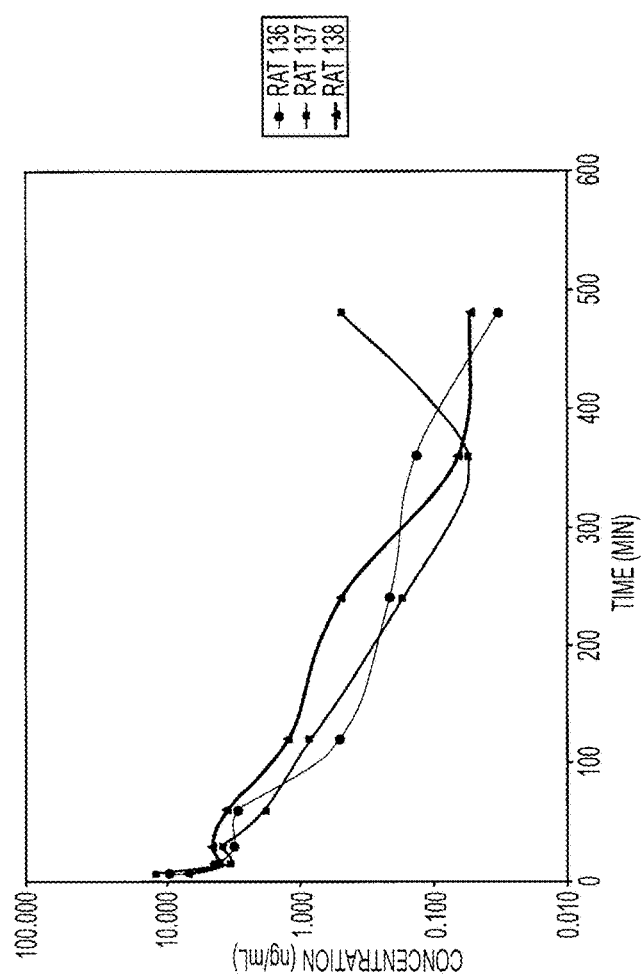
FIG. 11 is a graphical representation of the plasma concentration versus time curve for treprostinil in rat following intraduodenal administration of treprostinil monoalanine (chain) as described in Example 3.
Figure 12:
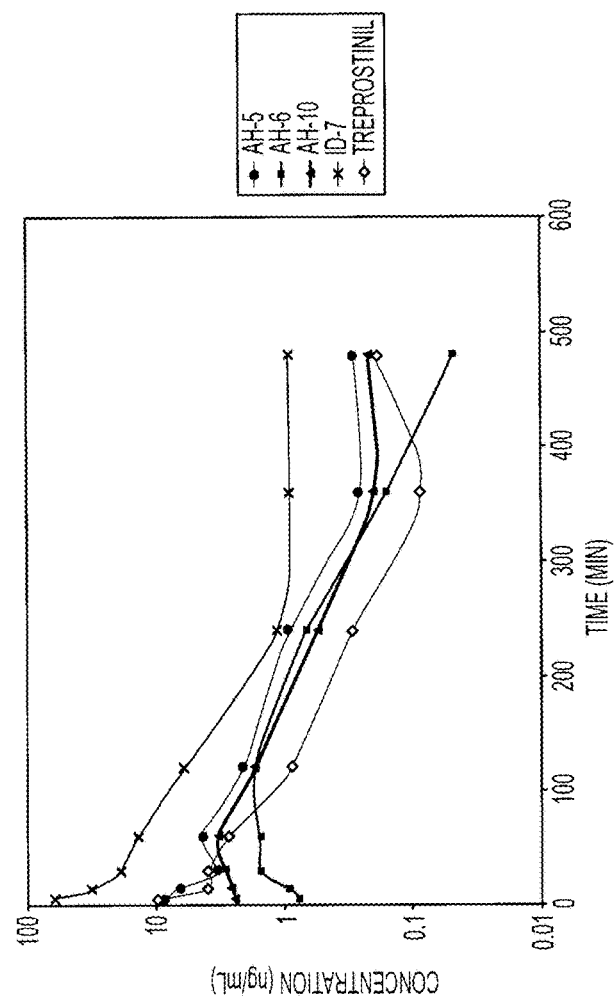
FIG. 12 is a graphical representation of the average plasma concentration versus time curve for each prodrug compared to treprostinil alone from Example 1, as described in Example 3. Treprostinil was dosed at 1 mg/kg whereas the prodrugs were dosed at 0.5 mg/kg.
Figure 13:
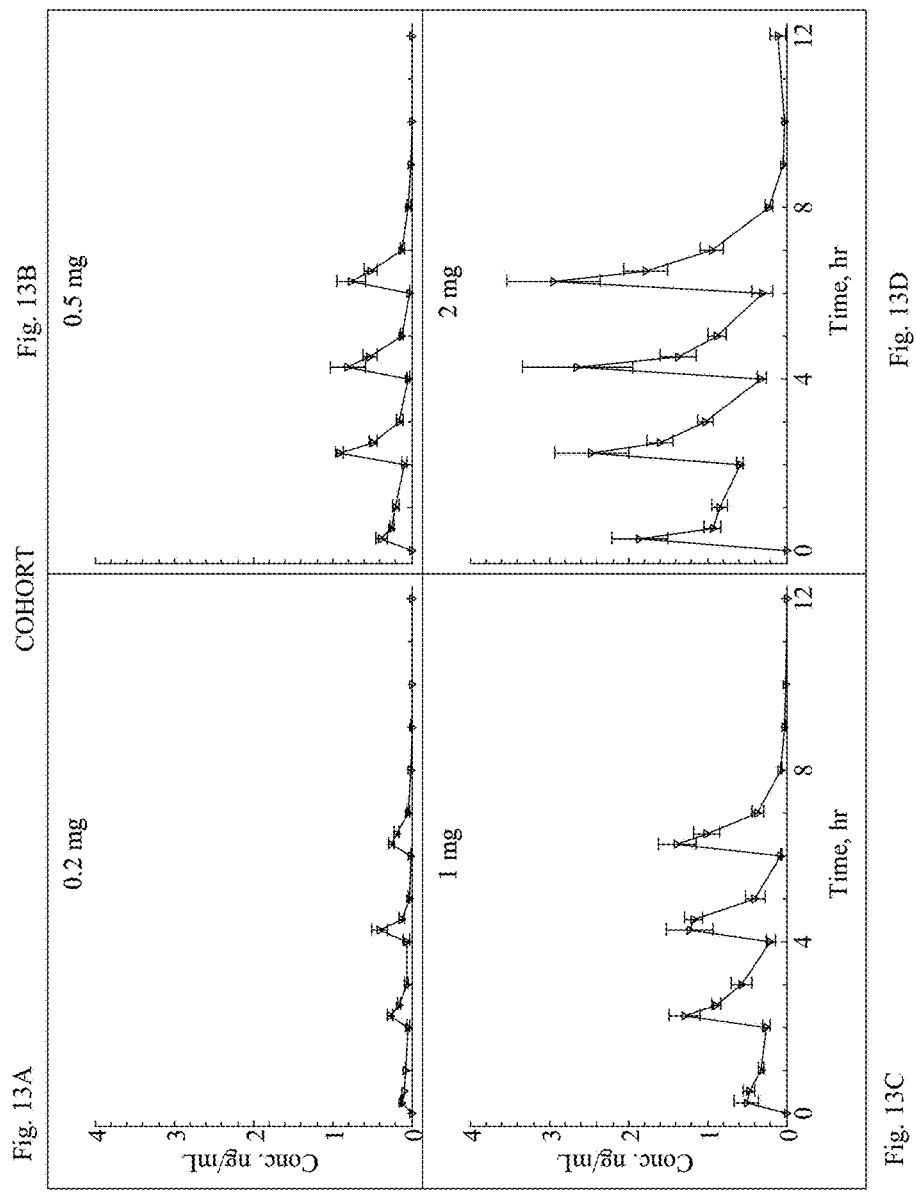
FIGS. 13A-13D respectively show doses, administered every two hours for four doses, for either 0.05 mg per dose (total=0.2 mg), 0.125 mg per dose (total=0.5 mg), 0.25 mg per dose (total=1.0 mg), or 0.5 mg per dose (total=2.0 mg).

*n = 2,
$^\lambda$concentration falls below the limit of quantitation (LOQ) of the analytical method The plasma concentration versus time curves for intravenous, intraportal, intraduodenal, intracolonic and oral dosing are shown in FIGS. 1 and 2. FIG. 3 shows the average plasma concentration versus time curves for all five routes of administration. In the experiments shown in these figures, the diethanolamine salt was used. Table 4 shows the pharmacokinetic parameters determined for treprostinil. The individual bioavailabilities of each rat are found in Table 5.

TABLE 4

Average Bioavailability and Pharmacokinetic Parameters of Treprostinil in Rats

| Route of Administration | Average AUC$_{480\ min}$ (min · ng/mL) | C$_{max}$ (ng/mL) | T$_{max}$ (min) | T$_{1/2}$ (min) | Average Bioavailability (%) ± SD | Volume of Distribution* (L · kg$^{-1}$) | CLs (mL · min$^{-1}$ · kg$^{-1}$)* |
|---|---|---|---|---|---|---|---|
| Intravenous | 11253.49 | 2120$^\Psi$ | 0 | 94 | NA | 1.98 | 88.54 |
| Intraportal Vein | 4531.74 | 302 | 2 | ND | 40.3 ± 5.5 | ND | ND |
| Intraduodenal | 2712.55 | 62 | 5 | ND | 24.1 ± 0.5 | ND | ND |

TABLE 4-continued

Average Bioavailability and Pharmacokinetic Parameters of Treprostinil in Rats

| Route of Administration | Average $AUC_{480\ min}$ (min · ng/mL) | $C_{max}$ (ng/mL) | $T_{max}$ (min) | $T_{1/2}$ (min) | Average Bioavailability (%) ± SD | Volume of Distribution* (L · kg$^{-1}$) | CLs (mL · min$^{-1}$ · kg$^{-1}$)* |
|---|---|---|---|---|---|---|---|
| Intracolonic | 364.63 | 8 | 5 | ND | 3.2 ± 2.5 | ND | ND |
| Oral | 1036.23 | 5 | 5 | ND | 9.2 ± 1.4 | ND | ND |

*Normalized to the average weight of the rats
ND: Not determined
$^{\Psi}$Extrapolated Value

TABLE 5

Individual Bioavailabilities of Treprostinil in Rats

| Route of Administration | Rat # | Individual $AUC_{480\ min}$ (min · ng/mL) | Individual Bioavailability (%) |
|---|---|---|---|
| Intravenous | 118 | 10302.85 | NA |
|  | 119 | 9981.52 | NA |
|  | 120 | 13510.65 | NA |
| Intraportal Vein | 121 | 4970.67 | 44.2 |
|  | 122 | 4093.21 | 36.4 |
|  | 123 | ND | ND |
| Intraduodenal | 124 | 2725.68 | 24.2 |
|  | 125 | 2763.60 | 24.6 |
|  | 126 | 2646.05 | 23.5 |
| Intracolonic | 127 | 72.63 | 0.7 |
|  | 128 | 395.08 | 3.5 |
|  | 129 | 625.20 | 5.6 |
| Oral | 130 | 998.70 | 8.9 |
|  | 131 | 907.60 | 8.1 |
|  | 132 | 1203.73 | 10.7 |

NA: Not applicable
ND: Not determined

Conclusions

Treprostinil has a terminal plasma half-life of 94 minutes. The distribution phase of treprostinil has a half-life of 10.3 minutes and over 90% of the distribution and elimination of the compound occurs by 60 minutes post-dosing. The volume of distribution (Vd=1.98 L/kg) is greater than the total body water of the rat (0.67 L/kg) indicating extensive partitioning into tissues. The systemic clearance of treprostinil (88.54 mL/min/kg) is greater than the hepatic blood flow signifying that extra-hepatic clearance mechanisms are involved in the elimination of the compound.

First pass hepatic elimination of treprostinil results in an average intraportal vein bioavailability of 40.3%. Fast but incomplete absorption is observed after intraduodenal, intracolonic and oral dosing ($T_{max}$ 5 min). By comparing the intraportal vein (40.3%) and intraduodenal bioavailability (24.1%) it appears that approximately 60% of the compound is absorbed in the intestine. The average intraduodenal bioavailability is almost three times greater than the oral bioavailability suggesting that degradation of treprostinil in the stomach or gastric emptying may influence the extent of systemic absorption.

Example 2

In this Example, Treprostinil concentrations were determined in male Sprague-Dawley rats following a single oral dose of the following compounds:

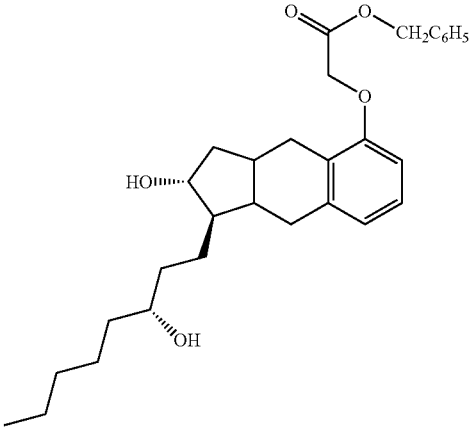

treprostinil benzyl ester

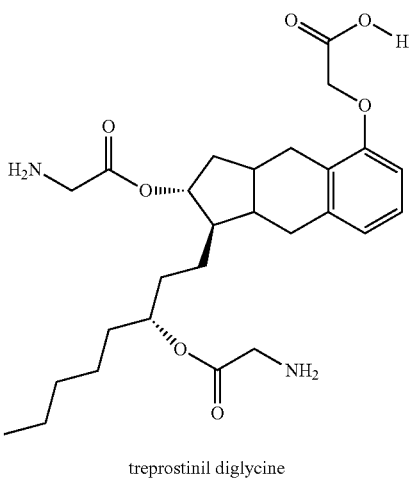

treprostinil diglycine

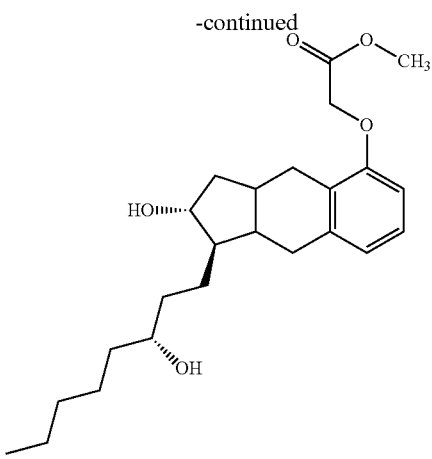

treprostinil methyl ester

Experimental

Dosing Solution Preparation

All dosing vehicles were prepared less than 2 hours prior to dosing.

1. Treprostinil Methyl Ester

A solution of treprostinil methyl ester was prepared by dissolving 2.21 mg of treprostinil methyl ester with 0.85 mL of dimethylacetamide (DMA). This solution was then diluted with 7.65 mL of PEG 400:Polysorbate 80:Water, 40:1:49. The final concentration of the dosing vehicle was 0.26 mg/mL of treprostinil methyl ester equivalent to 0.25 mg/mL of Treprostinil. The dosing vehicle was a clear solution at the time of dosing.

2. Treprostinil Benzyl Ester

A solution of treprostinil benzyl ester was prepared by dissolving 2.58 mg of treprostinil benzyl ester with 0.84 mL of dimethylacetamide (DMA). This solution was then diluted with 7.54 mL of PEG 400:Polysorbate 80:Water, 40:1:49. The final concentration of the dosing vehicle was 0.268 mg/mL of treprostinil benzyl ester equivalent to 0.25 mg/mL of Treprostinil. The dosing vehicle was a clear solution at the time of dosing.

3. Treprostinil Diglycine

A solution of treprostinil diglycine was prepared by dissolving 1.86 mg of compound with 0.58 mL of dimethylacetamide (DMA). This solution was then diluted with 5.18 mL of PEG 400:Polysorbate 80:Water, 40:1:49. The final concentration of the dosing vehicle was 0.323 mg/mL of treprostinil diglycine equivalent to 0.25 mg/mL of Treprostinil. The dosing vehicle was a clear solution at the time of dosing.

Animal Dosing

The plasma concentrations of Treprostinil following administration of each prodrug were evaluated in male Sprague-Dawley rats. Rats were purchased from Hilltop Lab Animals (Scottdale, Pa.). The animals were shipped from Hilltop to Absorption Systems' West Chester University facility (West Chester, Pa.). They were housed for at least twenty-four hours prior to being used in the study. The animals were fasted for approximately 16 hours prior to dosing. The rats used in this study were divided into three groups (I, II and III). Groups I-III were dosed on the same day.

The weight of the animals and the dosing regimen are presented in Table 6.

TABLE 6

Study Design

| Group | Rat # | Weight (kg) | Route of Administration | Compound Dosed | Dose Volume (mL/kg) | Dose* (mg/kg) |
|---|---|---|---|---|---|---|
| I | 638 | 306 | Oral | Treprostinil methyl ester | 2 | 0.520 |
|   | 639 | 310 | Oral |  |   |   |
|   | 640 | 319 | Oral |  |   |   |
| II | 641 | 319 | Oral | Treprostinil benzyl ester | 2 | 0.616 |
|   | 642 | 309 | Oral |  |   |   |
|   | 643 | 320 | Oral |  |   |   |
| III | 644 | 318 | Oral | Treprostinil diglycine | 2 | 0.646 |
|   | 645 | 313 | Oral |  |   |   |
|   | 646 | 322 | Oral |  |   |   |

*This dose of prodrug = 0.500 mg/kg of the active, Treprostinil

Animals were dosed via oral gavage. Blood samples were taken from a jugular vein cannula at the following time points:

0 (pre-dose) 5, 15, 30, 60, 120, 240, 360 and 480 minutes

The blood samples were withdrawn and placed into tubes containing 30 μL of a solution of 500 units per mL of heparin in saline, and centrifuged at 13,000 rpm for 10 minutes. Approximately 200 μl of plasma was then removed and dispensed into appropriately labeled polypropylene tubes containing 4 μL of acetic acid in order to stabilize any prodrug remaining in the samples. The plasma samples were frozen at −20° C. and were transported on ice to Absorption Systems Exton Facility. There they were stored in a −80° C. freezer pending analysis.

Analysis of Plasma Samples

Plasma samples were analyzed as described in Example 1. In brief, Treprostinil was extracted from the plasma via liquid-liquid extraction then analyzed by LC/MS/MS. The analytical validation results were reported previously in Example 1. The lower limit of quantification (LLOQ) of the analytical method was 0.01 ng/mL. Samples were not assayed for unchanged prodrug.

Acceptance Criteria for Analytical Runs

Two standard curves, with a minimum of five points per curve, and a minimum of two quality control samples (QCs) were dispersed throughout each run. Each route of administration was bracketed by a standard curve used for back-calculation. The standards and QCs must be within ±15% (20% for the LLOQ) accuracy and precision for the run to be accepted. At least 75% of all standards and QCs must pass the acceptance criteria.

Pharmacokinetic Analysis

Pharmacokinetic analysis was performed on the plasma concentration of Treprostinil for each individual rat at each time point and on the average plasma concentration for all three rats in the group for each time point. The data were subjected to non-compartmental analysis using the pharmacokinetic program WinNonLin v. 3.1 (2).

Results

Study Observations

No adverse reactions were observed following oral administration of treprostinil methyl ester, treprostinil benzyl ester or treprostinil diglycine.

Plasma Stability of Prodrugs in Acidified Rat Plasma

In order to terminate any conversion of prodrug to active after samples were withdrawn the plasma was acidified. Acetic acid (v/v) was added to each plasma sample immediately after centrifugation of the red blood cells to a concentration of 2%. In-vitro plasma stability of each prodrug was performed to insure that the compound was stable in acidified plasma. To perform this assay 2% acetic acid was added to blank rat plasma obtained from Lampire Biological. The acidified rat plasma was equilibrated at 37° C. for three minutes prior to addition of prodrug. The initial concentration of each prodrug was 1000 ng/mL. A 100 μL aliquot of plasma (n=3 per time point) was taken at 0, 60 and 120 minutes. Each aliquot was combined with 20 μL of HCl and vortexed. Liquid-liquid extraction was then performed and the concentration of Treprostinil in each sample determined. The concentration of Treprostinil at each time point in acidified rat plasma is given in Table 7. Small amounts of Treprostinil appear to be present in the neat compound sample of treprostinil methyl ester and treprostinil diglycine. The concentration of Treprostinil remained constant throughout the course of the experiment, indicating that there was no conversion of prodrug into active compound occurring in acidified plasma.

TABLE 7

Plasma Stability of Prodrugs in Acidified Dog Plasma

| | Treprostinil Concentration (ng/mL) ± SD (n = 3) | | |
|---|---|---|---|
| Time (min) | Treprostinil methyl ester | Treprostinil benzyl ester | Treprostinil diglycine |
| 0 | 56.8 ± 9.3 | <0.01 | 54.9 ± 4.3 |
| 60 | 55.1 ± 5.0 | <0.01 | 51.8 ± 5.9 |

TABLE 7-continued

Plasma Stability of Prodrugs in Acidified Dog Plasma

| | Treprostinil Concentration (ng/mL) ± SD (n = 3) | | |
|---|---|---|---|
| Time (min) | Treprostinil methyl ester | Treprostinil benzyl ester | Treprostinil diglycine |
| 120 | 53.8 ± 1.3 | <0.01 | 54.5 ± 0.8 |
| Total % Treprostinil | 5.7 | <0.01 | 5.5 |

Average Treprostinil plasma concentrations following administration of treprostinil methyl ester, treprostinil benzyl ester or treprostinil diglycine are shown in Table 8.

TABLE 8

Treprostinil Concentrations (Average ± SD (n = 3) Plasma Concentrations (ng/mL)

| Oral Dosing Solution | Pre-Dose | 5 (min) | 15 (min) | 30 (min) | 60 (min) | 120 (min) | 240 (min) | 360 (min) | 480 (min) |
|---|---|---|---|---|---|---|---|---|---|
| Treprostinil methyl ester | 0 | <0.01 | 0.2 ± 0.0 | 0.3 ± 0.1 | 0.5 ± 0.1 | 1.5 ± 0.8 | 0.2 ± 0.7 | <0.01 | 0.1 ± 0.1 |
| Treprostinil benzyl ester | 0 | 3.1 ± 2.8 | 1.9 ± 0.8 | 2.5 ± 1.5 | 3.2 ± 1.9 | 7.3 ± 4.9 | 1.6 ± 1.2 | 0.4 ± 0.40 | 0.6 ± 0.9 |
| Treprostinil diglycine | 0 | <0.01 | 1.1 ± 1.9 | 6.6 ± 10.7 | 0.5 ± 0.3* | 40. ± 5.8 | 9.0 ± 13.5 | 2.1 ± 2.9 | 1.3 ± 0.8 |

*Due to insufficient amount of sample collected this time point is the average of n = 2 rats.

FIGS. 4-7 contain graphical representations of the plasma concentration versus time curves for Treprostinil in rat following administration of each prodrug. Table 9 lists each figure and the information displayed.

TABLE 9

List of Figures

| FIG. | Description |
|---|---|
| 4 | Oral Dose of Treprostinil methyl ester |
| 5 | Oral Dose of Treprostinil benzyl ester |
| 6 | Oral Dose of Treprostinil diglycine |
| 7 | Oral Dose of Treprostinil benzyl ester and Treprostinil diglycine Compared to Treprostinil Alone from Example 1 |

Pharmacokinetic Analysis

Bioavailability of the prodrug was determined relative to that of the active compound based on Example 1 in which Treprostinil was dosed to rats. The following formula was used to determine relative bioavailability (F):

$$\text{Relative } F = (AUC_{(Prodrug\ Dose)}/\text{Dose})/(AUC_{(Treprostinil\ Dose)}/\text{Dose}) * 100$$

Bioavailability was also determined relative to an intravenous dose of Treprostinil in rats determined in Example 1. Results are listed in Table 10.

TABLE 10

Average Relative Bioavailability and Pharmacokinetic Parameters of Treprostinil in Rats

| Test Compound Administered | Dose (mg/kg) | Average AUC$_{0-t}$ (min · ng/mL) | $C_{max}$ (ng/mL) | $T_{max}$ (min) | Relative Bioavailability (%) ± SD (n = 3) | Bioavailability (%) ± SD (n = 3) |
|---|---|---|---|---|---|---|
| Treprostinil methyl ester | 0.5 | 212 | 1.50 | 120 | 41.0 ± 16 | 3.8 ± 2 |
| Treprostinil benzyl ester | 0.5 | 1171 | 7.20 | 120 | 226 ± 155 | 20.8 ± 14 |
| Treprostinil diglycine | 0.5 | 2242 | 9.04 | 240 | 433 ± 631 | 39.9 ± 58 |

Conclusions

In this study the relative oral bioavailabilities of prodrugs of Treprostinil were determined in rats. Treprostinil methyl ester resulted in Treprostinil area under the plasma concentration versus time curves (AUCs) less than that after dosing the active compound. Prodrugs treprostinil benzyl ester and treprostinil diglycine both had Treprostinil average AUCs greater than that after dosing of the active compound. Treprostinil diglycine had the highest relative bioavailability of 433% with over 4 times more Treprostinil reaching the systemic circulation. The Cmax of 9 ng/mL of Treprostinil following administration of treprostinil diglycine occurred at 240 minutes post-dosing. The Cmax following dosing of Treprostinil is 5 ng/mL and occurs only 5 minutes post-dosing. Treprostinil benzyl ester had a relative bioavailability of 226±155% with a Cmax of 7.2 ng/mL occurring 120 minutes post-dosing. It should also be noted that the AUCs are not extrapolated to infinity.

REFERENCES

1. WinNonlin User's Guide, version 3.1, 1998-1999, Pharsight Co., Mountain View, Calif. 94040.

Example 3

This example illustrates a pharmacokinetic study of treprostinil following administration of a single duodenal dose of treprostinil and various prodrugs of the present invention.

In this study, the area under the curve of Treprostinil in male Sprague-Dawley rats following a single intraduodenal dose of treprostinil monophosphate (ring), treprostinil monovaline (ring), treprostinil monoalanine (ring) or treprostinil monoalanine (chain), prodrugs of treprostinil was compared. The compounds were as follows:

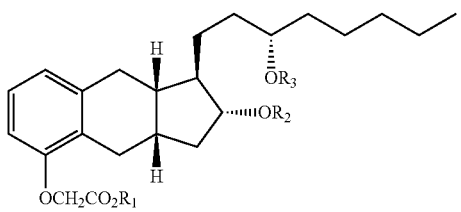

having the following substituents:

| Compound | $R^1$ | $R^2$ | $R^3$ |
|---|---|---|---|
| treprostinil monophosphate (ring) | H | —PO$_3$H$_3$ | H |
| treprostinil monovaline (ring) | H | —COCH(CH(CH$_3$)$_2$)NH$_2$ | H |
| treprostinil monoalanine (ring) | H | —COCH(CH$_3$)NH$_2$ | H |
| treprostinil monoalanine (chain) | H | H | —COCH(CH$_3$)NH$_2$ |

Experimental

Dosing Solution Preparation

All dosing vehicles were prepared less than 2 hours prior to dosing.
1. Treprostinil Monophosphate (Ring)
A dosing solution of treprostinil monophosphate (ring) was prepared by dissolving 1.01 mg of treprostinil monophosphate (ring) in 0.167 mL of dimethylacetamide (DMA) until dissolved. This solution was further diluted with 1.50 mL of PEG 400:Polysorbate 80:Water, 40:1:49. The final concentration of the dosing vehicle was 0.603 mg/mL of prodrug equivalent to 0.5 mg/mL of Treprostinil. The dosing vehicle was a clear solution at the time of dosing.
2. Treprostinil Monovaline (Ring)
A 50 mg/mL solution of treprostinil monovaline (ring) was prepared in dimethylacetamide (DMA). A 25 µL aliquot of the 50 mg/mL stock solution was then diluted with 175 µL of DMA and 1.8 mL of PEG 400:Polysorbate 80:Water, 40:1:49. The final concentration of the dosing vehicle was 0.625 mg/mL of prodrug equivalent to 0.5 mg/mL of Treprostinil. The dosing vehicle was a clear solution at the time of dosing.
3. Treprostinil Monoalanine (Ring)
A solution of treprostinil monoalanine (ring) was prepared by dissolving 1.05 mg of treprostinil monoalanine (ring) in 0.178 mL of dimethylacetamide (DMA) until dissolved. This solution was further diluted with 1.60 mL of PEG 400:Polysorbate 80:Water, 40:1:49. The final concentration of the dosing vehicle was 0.590 mg/mL of treprostinil monoalanine (ring) equivalent to 0.5 mg/mL of Treprostinil. The dosing vehicle was a clear solution at the time of dosing.
4. Treprostinil Monoalanine (Chain)
A solution of treprostinil monoalanine (chain) was prepared by dissolving 0.83 mg of treprostinil monoalanine (chain) in 0.14 mL of dimethylacetamide (DMA) until dissolved. This solution was further diluted with 1.26 mL of PEG 400:Polysorbate 80:Water, 40:1:49. The final concentration of the dosing vehicle was 0.591 mg/mL of treprostinil monoalanine (chain) equivalent to 0.5 mg/mL of Treprostinil. The dosing vehicle was a clear solution at the time of dosing.

Animal Dosing

The plasma concentrations of Treprostinil following oral administration of each prodrug were evaluated in male Sprague-Dawley rats. Twelve rats were purchased from Hilltop Lab Animals (Scottdale, Pa.). The animals were shipped from Hilltop to Absorption Systems' West Chester University facility (West Chester, Pa.). They were housed for at least twenty-four hours prior to being used in the study. The animals were fasted for approximately 16 hours prior to dosing. The twelve rats used in this study were divided into four groups. All groups were dosed on day 1 of the study. The weight of the animals and the dosing regimen are presented in Table 11.

TABLE 11

| Rat # | Weight (g) | Compound | Dose Volume (mL/kg) | Dose* (mg/kg) |
|---|---|---|---|---|
| 130 | 327 | treprostinil monophosphate (ring) | 1 | 0.603 |
| 131 | 321 | treprostinil monophosphate (ring) | 1 | 0.603 |
| 132 | 310 | treprostinil monophosphate (ring) | 1 | 0.603 |
| 133 | 328 | treprostinil monovaline (ring) | 1 | 0.625 |
| 134 | 326 | treprostinil monovaline (ring) | 1 | 0.625 |
| 135 | 346 | treprostinil monovaline (ring) | 1 | 0.625 |
| 136 | 321 | treprostinil monoalanine (chain) | 1 | 0.591 |
| 137 | 319 | treprostinil monoalanine (chain) | 1 | 0.591 |
| 138 | 330 | treprostinil monoalanine (chain) | 1 | 0.591 |
| 139 | 316 | treprostinil monoalanine (ring) | 1 | 0.590 |
| 140 | 330 | treprostinil monoalanine (ring) | 1 | 0.590 |
| 141 | 339 | treprostinil monoalanine (ring) | 1 | 0.590 |

*This dose of prodrug = 0.500 mg/kg of treprostinil

Animals were dosed via an indwelling duodenal cannula. Blood samples were taken from a jugular vein cannula at the following time points: 0 (pre-dose) 5, 15, 30, 60, 120, 240, 360 and 480 minutes.

The blood samples were withdrawn and placed into tubes containing 30 µL of a solution of 500 units per mL of heparin in saline, and centrifuged at 13,000 rpm for 10 minutes. Approximately 2004 of plasma was then removed and dispensed into appropriately labeled polypropylene tubes containing 44 of acetic acid in order to stabilize any prodrug remaining in the samples. The plasma samples were frozen at −20° C. and were transported on ice to Absorption Systems Exton Facility. There they were stored in a −80° C. freezer pending analysis.

Analysis of Plasma Samples

Plasma samples were analyzed using the methods described above. In brief, Treprostinil was extracted from the plasma via solid phase extraction then analyzed by LC/MS/MS. The lower limit of quantification (LLOQ) of the analytical method was 0.03 ng/mL.

Acceptance Criteria for Analytical Runs

Four standard curves, with a minimum of five points per curve, and a minimum of two quality control samples (QCs) at 3 concentrations were dispersed throughout each run. Each prodrug set was bracketed by a standard curve used for back-calculation. The standards and QCs must be within ±15% (20% for the LLOQ) accuracy and precision for the run to be accepted. At least 75% of all standards and QCs must pass the acceptance criteria.

Pharmacokinetic Analysis

Pharmacokinetic analysis was performed on the plasma concentration of Treprostinil for each individual rat at each time point and on the average plasma concentration for all three rats in the group for each time point.

The data were subjected to non-compartmental analysis using the pharmacokinetic program WinNonLin v. 3.1 (2).

Results

Study Observations

No adverse reactions were observed following intraduodenal administration of treprostinil monophosphate (ring), treprostinil monovaline (ring), treprostinil monoalanine (ring) or treprostinil monoalanine (chain).

Ex-Vivo Plasma Stability of Prodrugs in Acidified Rat Plasma

In order to terminate any conversion of prodrug to active after samples were withdrawn, the plasma was acidified. Acetic acid (v/v) was added to each plasma sample immediately after separation of the red blood cells to a concentration of 2%. In-vitro plasma stability of each prodrug was performed to insure that the compound was stable in acidified plasma. To perform this assay 2% acetic acid was added to blank rat plasma obtained from Lampire Biological. The acidified rat plasma was brought to room temperature for three minutes prior to addition of prodrug. The initial concentration of each prodrug was 1000 ng/mL. A 100 µL aliquot of plasma (n=3 per time point) was taken at 0, 60 and 120 minutes. Sample preparation of each plasma sample was performed as described above and the concentration of Treprostinil monitored.

Treprostinil concentrations did not increase in any of the acidified plasma samples spiked with prodrug over the two-hour period of the experiment.

Sample Analysis

Average Treprostinil plasma concentrations following administration of treprostinil monophosphate (ring), treprostinil monovaline (ring), treprostinil monoalanine (ring) or treprostinil monoalanine (chain) are shown in Table 12.

TABLE 12

| | AVERAGE ± SD (N = 3) PLASMA TREPROSTINIL CONCENTRATIONS (NG/ML) | | | | | | | | |
|---|---|---|---|---|---|---|---|---|---|
| Oral Dosing Solution | Pre-dose | 5 (min) | 15 (min) | 30 (min) | 60 (min) | 120 (min) | 240 (min) | 360 (min) | 480 (min) |
| treprostinil monophosphate (ring) | 0 | 8.62 ± 3.0 | 6.57 ± 1.7 | 3.31 ± 1.2 | 4.31 ± 0.8 | 2.07 ± 0.4 | 0.91 ± 0.5 | 0.26 ± 0.08 | 0.3 ± 0.08 |
| treprostinil monovaline (ring) | 0 | 0.76 ± 0.2 | 0.91 ± 0.7 | 1.52 ± 0.6 | 1.53 ± 0.6 | 1.65 ± 0.7 | 0.66 ± 0.1 | 0.15 ± 0.03 | 0.05 ± 0.02 |

TABLE 12-continued

| Oral Dosing Solution | Pre-dose | 5 (min) | 15 (min) | 30 (min) | 60 (min) | 120 (min) | 240 (min) | 360 (min) | 480 (min) |
|---|---|---|---|---|---|---|---|---|---|
| | AVERAGE ± SD (N = 3) PLASMA TREPROSTINIL CONCENTRATIONS (NG/ML) | | | | | | | | |
| treprostinil monoalanine (ring) | 0 | 2.42 ± 0.6 | 2.52 ± 0.4 | 2.91 ± 0.6 | 3.25 ± 1.5 | 1.69 ± 0.4 | 0.55 ± 0.2 | 0.20 ± 0.1 | 0.22 ± 0.2 |
| treprostinil monoalanine (chain) | 0 | 9.53 ± 2.6 | 3.92 ± 0.6 | 3.83 ± 0.7 | 2.74 ± 0.9 | 0.86 ± 0.4 | 0.29 ± 0.2 | 0.08 ± 0.04 | 0.19 ± 0.3 |

FIGS. 8-12 contain graphical representations of the plasma concentration versus time curves for Treprostinil in rat following administration of each prodrug. Table 13 lists each figure and the information displayed.

TABLE 13

| FIG. | Description |
|---|---|
| 8 | Intraduodenal dose of treprostinil monophosphate (ring) |
| 9 | Intraduodenal dose of treprostinil monovaline (ring) |
| 10 | Intraduodenal dose of treprostinil monoalanine (ring) |
| 11 | Intraduodenal dose of treprostinil monoalanine (chain) |
| 12 | Intraduodenal dose of each prodrug compared to treprostinil alone from Example 1 |

Pharmacokinetic Analysis

Bioavailability of the prodrug was determined relative to that of the active compound based on a previous study in which Treprostinil was dosed to rats. The following formula was used to determine relative bioavailability (F):

Relative $F = (AUC_{(ProdrugDose)}/Dose)/(AUC_{(Treprostinil\ Dose)}/Dose)*100$

Absolute bioavailability was also estimated using data from an intravenous dose of Treprostinil in rats determined in Example 1. Results are listed in Table 14.

TABLE 14

List of Figures

| FIG. | Description |
|---|---|
| 8 | Intraduodenal Dose of treprostinil monophosphate (ring) |
| 9 | Intraduodenal Dose of treprostinil monovaline (ring) |
| 10 | Intraduodenal Dose of treprostinil monoalanine (ring) |
| 11 | Intraduodenal Dose of treprostinil monoalanine (chain) |
| 12 | Intraduodenal Dose of Each Prodrug Compared to Treprostinil Alone from Example 1 |

Conclusions

The relative intraduodenal bioavailabilities of four prodrugs of Treprostinil were determined in rats. All the compounds had relative intraduodenal bioavailabilities less than that of the active compound. treprostinil monophosphate (ring) and treprostinil monoalanine (ring) had the highest relative intraduodenal bioavailability at 56% and 38% respectively. The $T_{max}$ for treprostinil monophosphate (ring) and treprostinil monoalanine (chain) occurred 5 minutes post-dosing. treprostinil monovaline (ring) and treprostinil monoalanine (ring) had longer absorption times with $T_{max}$ values of 120 and 60 minutes respectively. Maximum Treprostinil concentrations were highest following treprostinil monophosphate (ring) and treprostinil monoalanine (chain) dosing. They reached approximately 9 ng/mL 5 minutes post-dosing. The bioavailabilities are much greater when dosed intraduodenally than when dosed orally as measured by treprostinil plasma levels.

REFERENCES

1. WinNonlin User's Guide, version 3.1, 1998-1999, Pharsight Co., Mountain View, Calif. 94040.

Example 4

In this Example, Treprostinil concentrations will be determined in male Sprague-Dawley rats following a single oral or intraduodenal dose of the following compounds of structure II:

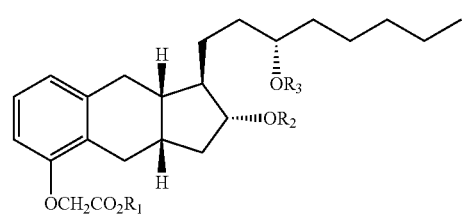

having the following substituents:

| Cpd. | $R^1$ | $R^2$ | $R^3$ |
|---|---|---|---|
| A | —$CH_2CONH_2$ | H | H |
| B | —$CH_2CON(CH_2)_2OH$ | H | H |
| C | —$CH_2CON(CH_3)_2$ | H | H |
| D | —$CH_2CONHOH$ | H | H |
| E | —$CH_2C_6H_4NO_2$ (p)* | H | H |
| F | —$CH_2C_6H_4OCH_3$ (p)* | H | H |
| G | —$CH_2C_6H_4Cl$ (o)* | H | H |
| H | —$CH_2C_6H_4(NO_2)_2$ (o,p)* | H | H |

-continued

| Cpd. | R¹ | R² | R³ |
| --- | --- | --- | --- |
| I | —CH₂C₆H₄F (p)* | H | H |
| J | H | —PO₃H₃ | H |
| K | H | H | —PO₃H₃ |
| L | H | —COCH₂NH₂ | H |
| M | H | H | —COCH₂NH₂ |
| N | H | —COCH(CH₃)NH₂ | H |
| O | H | H | —COCH(CH₃)NH₂ |
| P | H | —COCH(CH₃)NH₂ | —COCH(CH₃)NH₂ |

*o denotes ortho substitution, m denotes meta substitution and p denotes para substitution.

Examples of these compounds include:

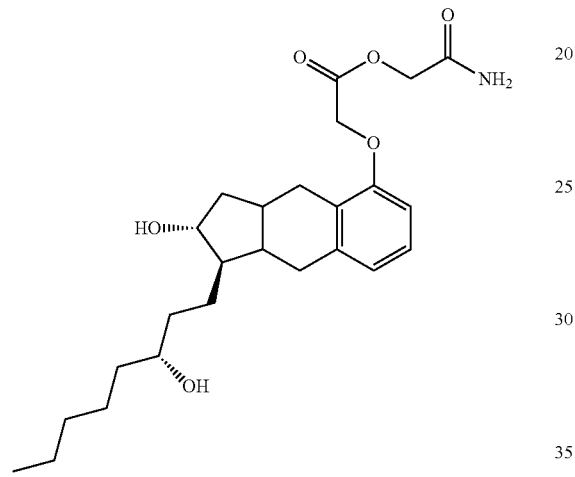

A

C₂₅H₃₇NO₆
Exact Mass: 447.26
Mol. Wt.: 447.56
C, 67.09; H, 8.33; N, 3.13; O, 21.45
Treprostinil glycolamide ester

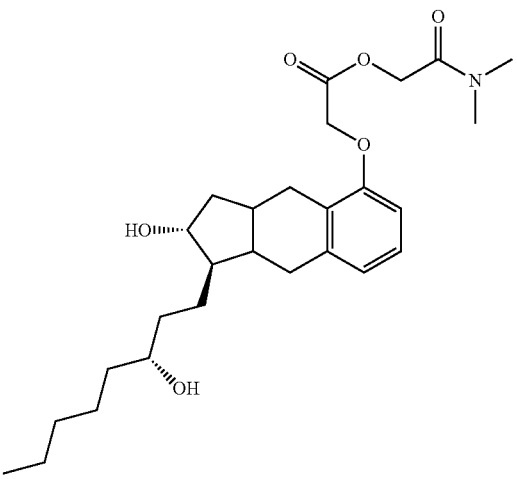

C

C₂₇H₄₁NO₆
Exact Mass: 475.29
Mol. Wt.: 475.62
C, 68.18; H, 8.69; N, 2.94; O, 20.18
Treprostinil N,N-dimethyl glycolamide

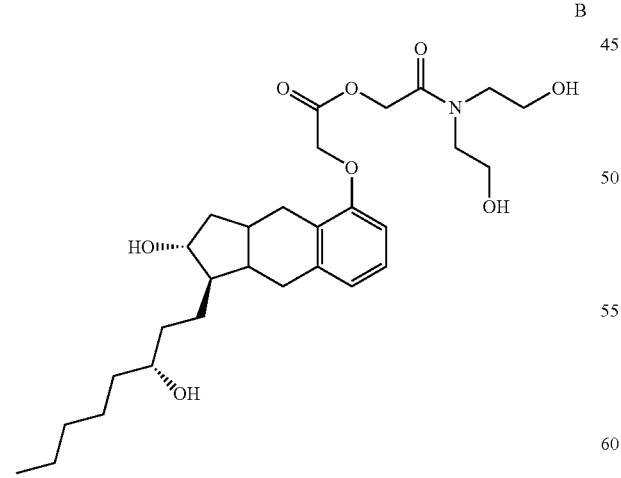

B

C₂₉H₄₅NO₈
Exact Mass: 535.31
Mol. Wt.: 535.67
C, 65.02; H, 8.47; N, 2.61; O, 23.89
Treprostinil N,N-diethanol glycolamide ester

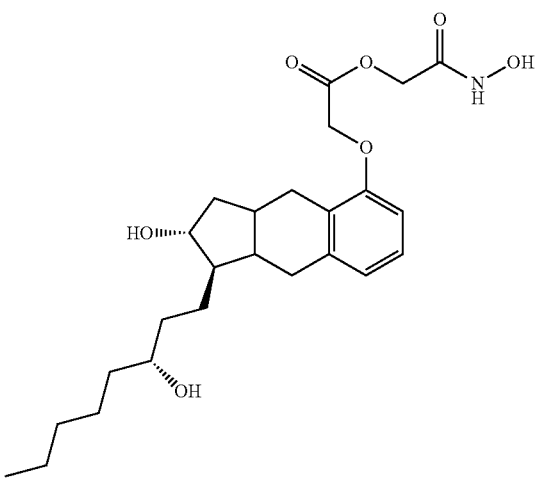

D

C₂₅H₃₇NO₇
Exact Mass: 463.26
Mol. Wt.: 463.56
C, 64.77; H, 8.05; N, 3.02; O, 24.16
Treprostinil N-hydroxy glycolamide ester -continued

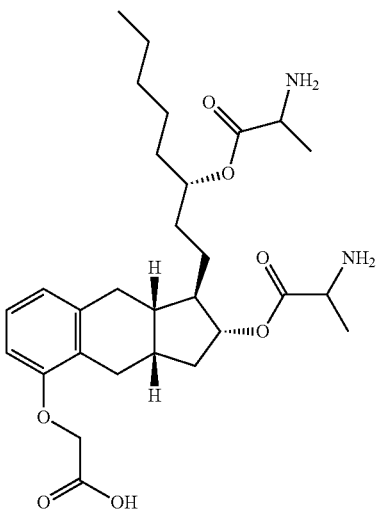

C₂₉H₄₄N₂O₇
Exact Mass: 532.31
Mol. Wt.: 532.67
C, 65.39; H, 8.33; N, 5.26; O, 21.03

Prodrug preparation and analysis will take place as described in Examples 1 and 2 above. Additionally, the oral bioavailability of treprostinil, treprostinil sodium and the compounds shown in Example 2 and this Example will be administered in close proximity to or simultaneously with various different p-glycoprotein inhibiting compounds at varying concentrations and tested to determine the effect of the p-glycoprotein inhibitors on the oral bioavailability of the compounds. The p-glycoprotein inhibitors will be administered both intravenously and orally.

Example 5

Clinical Studies with Treprostinil Diethanolamine

Introduction

Prior to proceeding directly into clinical studies with a sustained release (SR) solid dosage form of UT-15C (treprostinil diethanolamine), a determination of the pharmacokinetics of an oral "immediate release" solution was performed. The first clinical study (01-101) evaluated the ability of escalating doses of an oral solution of UT-15C to reach detectable levels in plasma, potential dose-plasma concentration relationship, bioavailability and the overall safety of UT-15C. Volunteers were dosed with the solutions in a manner that simulated a sustained release formulation releasing drug over approximately 8 hours.

The second clinical study (01-102) assessed the ability of two SR solid dosage form prototypes (i.e., 1. microparticulate beads in a capsule and, 2. tablet) to reach detectable levels in plasma and the potential influence of food on these plasma drug concentrations. The SR prototypes were designed to release UT-15C over approximately an 8 hour time period.

Details of the two clinical studies are described below.
Clinical Study 01-101
A Safety, Tolerability, and Pharmacokinetic Study of Multiple Escalating Doses of UT-15C (Treprostinil Diethanolamine) Administered as an Oral Solution in Healthy Adult Volunteers (Including Study of Bioavailability).

The oral solution of UT-15C was administered to 24 healthy volunteers to assess the safety and pharmacokinetic profile of UT-15C as well as its bioavailability. To mimic a SR release profile, doses were administered every two hours for four doses at either 0.05 mg per dose (total=0.2 mg), 0.125 mg per dose (total=0.5 mg), 0.25 mg per dose (total=1.0 mg), or 0.5 mg per dose (total=2.0 mg). Study endpoints included standard safety assessments (adverse events, vital signs, laboratory parameters, physical examinations, and electrocardiograms) as well as pharmacokinetic parameters.

All subjects received all four scheduled doses and completed the study in its entirety. Treprostinil plasma concentrations were detectable in all subjects following administration of an oral solution dose of UT-15C. Both $AUC_{inf}$ and $C_{max}$ increased in a linear fashion with dose for each of the four dose aliquots. The highest concentration observed in this study was 5.51 ng/mL after the third 0.25 mg solution dose aliquot of the 2.0 mg UT-15C total dose. Based on historical intravenous treprostinil sodium data, the mean absolute bioavailability values for the 0.2 mg, 0.5 mg, 1.0 mg and 2.0 mg doses of UT-15C were estimated to be 21%, 23%, 24% and 25%, respectively. The results of this study are respectively shown in FIGS. 13A-13D.

UT-15C was well tolerated by the majority of subjects at all doses given. There were no clinically significant, treatment emergent changes in hematology, clinical chemistry, urinalysis, vital signs, physical exams, and ECGs. The most frequently reported adverse events were flushing, headache, and dizziness. This safety profile with UT-15C (treprostinil diethanolamine) is consistent with the reported safety profile and product labeling of Remodulin (treprostinil sodium) and other prostacyclin analogs. Thus, changing the salt form of treprostinil did not result in any unexpected safety issues following the protocol specified dosing regimen (i.e. single dose every 2 hours for four total doses on a single day).
Clinical Study 01-102
A Safety, Tolerability, and Pharmacokinetic Study Comparing a Single Dose of a Sustained Release Capsule and Tablet Formulation of UT-15C (Treprostinil Diethanolamine) Administered to Healthy Adult Volunteers in the Fasted and Fed State The 01-102 study was designed to evaluate and compare the safety and pharmacokinetic profiles of a (1) UT-15C SR tablet prototype and, (2) UT-15C SR capsule prototype (microparticulate beads in a capsule) in both the fasted and fed state. Each of the SR dosage forms were designed to release UT-15C (1 mg) over an approximate 8-hour time period. Fourteen healthy adult volunteers were assigned to receive the SR tablet formulation while an additional fourteen volunteers were assigned to receive the SR capsule formulation. Subjects were randomized to receive a single dose (1 mg) of their assigned SR prototype in both the fasted and fed state. A crossover design was employed with a seven day wash-out period separating the fed/fasted states. For the fed portion of the study, subjects received a high calorie, high fat meal. Study endpoints included standard safety assessments (adverse events, vital signs, laboratory parameters, physical examinations, and electrocardiograms) as well as pharmacokinetic parameters.

Figure 14:
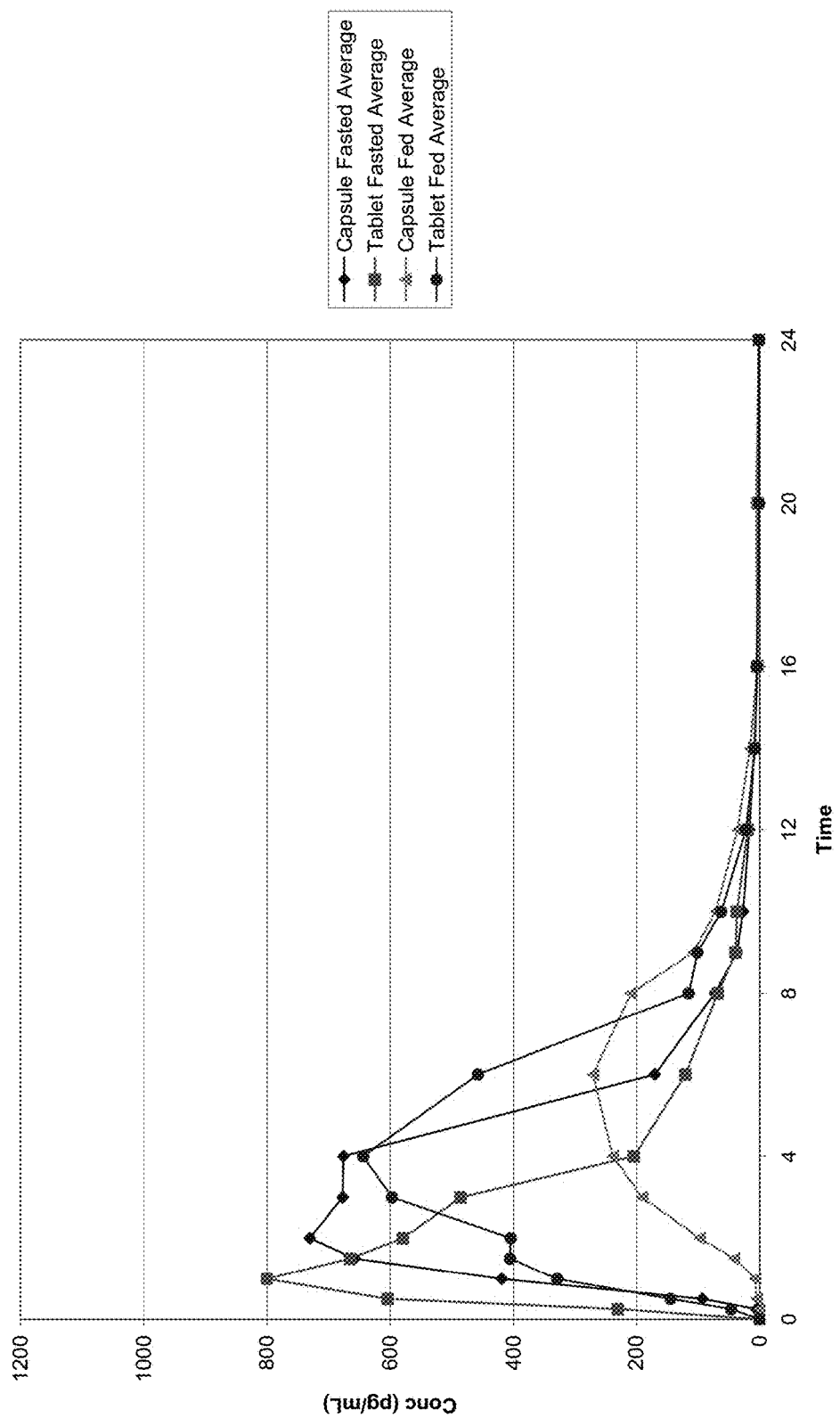
FIG. 14 shows pharmacokinetic profiles of UT-15C sustained release tablets and sustained release capsules, fasted and fed state.

All subjects administered UT-15C SR tablets and capsules had detectable treprostinil plasma concentrations. Calculations of area under the curve from zero to twenty-four hours ($AUC_{0-24}$) indicate that total exposure to UT-15C SR occurred in the following order: Tablet Fed>Capsule Fasted>Tablet Fasted>Capsule Fed. FIG. 14 displays the pharmacokinetic profiles of the two formulations in the fasted and fed states.

UT-15C SR tablets and capsules were tolerated by the majority of subjects. All adverse events were mild to moderate in severity and were similar to those described in Study 01-101 and in Remodulin's product labeling. Additionally, there were no treatment-emergent changes in vital signs, laboratory parameters, physical examinations, or electrocardiograms throughout the study.

These results demonstrate that detectable and potentially therapeutic drug concentrations can be obtained from a solid dosage form of UT-15C and that these concentrations can be maintained over an extended period of time through sustained release formulation technology.

Polymorphs of Treprostinil Diethanolamine

Two crystalline forms of UT-15C were identified as well as an amorphous form. The first, which is metastable, is termed Form A. The second, which is thermodynamically more stable, is Form B. Each form was characterized and interconversion studies were conducted to demonstrate which form was thermodynamically stable. Form A is made according to the methods in Table 15. Form B is made from Form A, in accordance with the procedures of Table 16.

TABLE 15

| Solvent | Conditions[a] | Habit/Description | XRPD Result[b] | Sample ID |
|---|---|---|---|---|
| tetrahydrofuran | FE | opaque white solids; morphology unknown, birefringent | A | 1440-72-02 |
| | SE | glassy transparent solids | A (PO) | 1440-72-03 |
| | SC (60° C.) | translucent, colorless glassy sheets of material, birefringent | A | 1440-72-16 |
| Toluene | slurry (RT), 6 d | white solids; opaque masses of smaller particles | A + B | 1440-72-01 |
| toluene:IPA (11.4:1) | SC(60° C.) | white solids; spherical clusters of fibers, birefringent | A | 1480-21-03 |
| Water | FE | opaque white solids; morphology unknowm, birefringent | A | 1440-72-07 |
| | SE | opaque ring of solids, birefringent | A + B | 1440-72-08 |
| | freeze dry | white, glassy transparent solids | A + B | 1480-58-02 |
| water:ethanol (1:1) | FE | opaque white solids; morphology unknown, birefringent | A + 11.5 pk | 1440-72-09 |
| | FE | clear and oily substance with some opaque solids | B | 1480-79-02 |
| | SE | glassy opaque ring of solid | A | 1440-72-10 |

[a]FE = fast evaporation; SE = slow evaporation; SC = slow cool
[b]IS = insufficient sample; PO = preferred orientation; LC = low crystallinity; pk = peak
c. XRPD = X-ray powder diffraction

TABLE 16

| Solvent | Conditions | Habit/Description | XRPD Result | Sample ID |
|---|---|---|---|---|
| ethanol/water (1:1) | FE | glassy appearing solids of unknown morphology; birefringent | —[b] | 1519-68-01 |
| 1,4-dioxane | slurry (50° C.), 6 d | white solids; opaque masses of material; morphology unknown | B | 1519-73-02[a] |
| | slurry (50° C.), 2 d | small grainy solids; with birefringence | B | 1557-12-01 |
| | subsample of 1557-12-01 | — | B | 1557-15-01 |
| | subsample of 1557-12-01 | white solids | B | 1557-15-02 |
| | slurry (50° C.), 2 d | — | B | 1557-17-01 |
| isopropanol | slurry (RT), 1 d | white solids | —[b] | 1519-96-03 |
| tetrahydrofuran | slurry (RT), 1 d | — | —[b] | 1519-96-02 |
| toluene | slurry (50° C.), 6 d | white solids | B | 1519-73-01 |

[a]Seeds of sample #1480-58-01 (A + B) added
[b]Samples not analyzed

Characterization of Crystal Forms:

Form A

Figure 15:
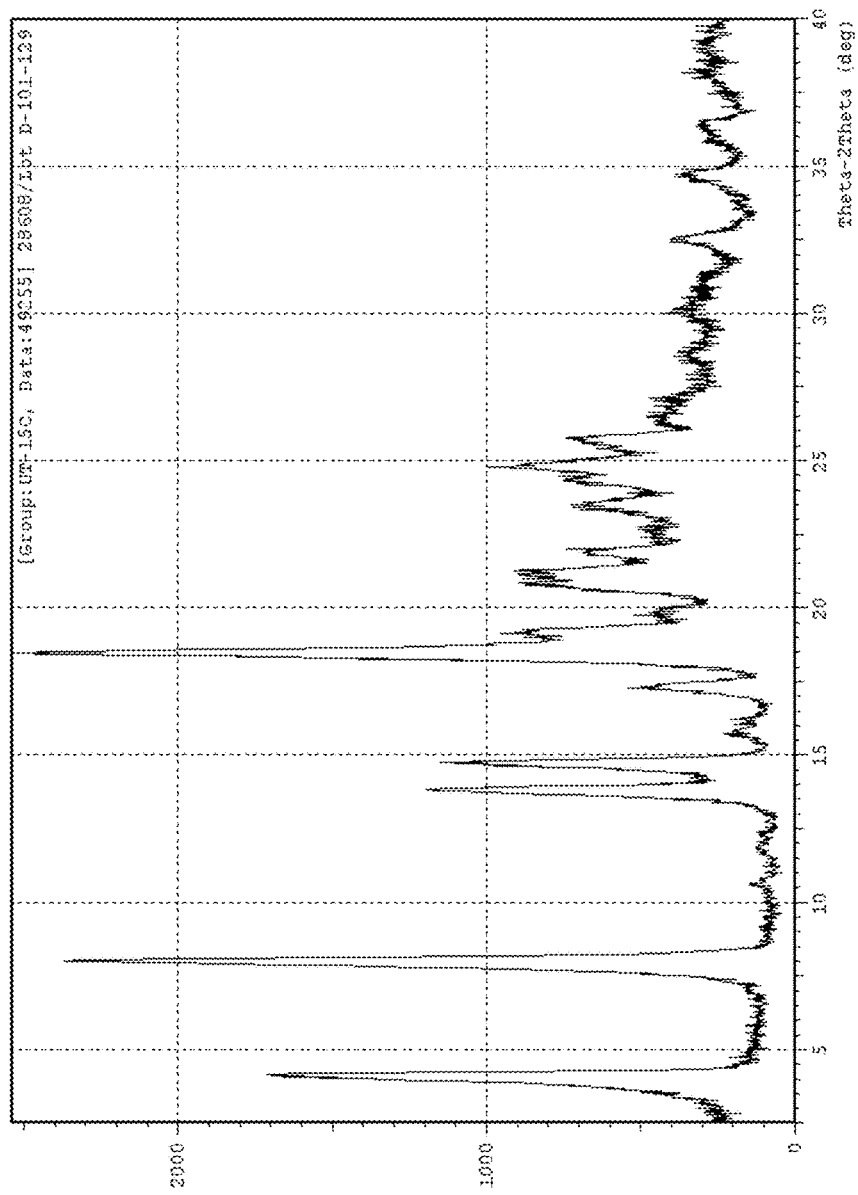
FIG. 15 shows an X ray powder diffraction spectrum of the polymorph Form A.
Figure 16:
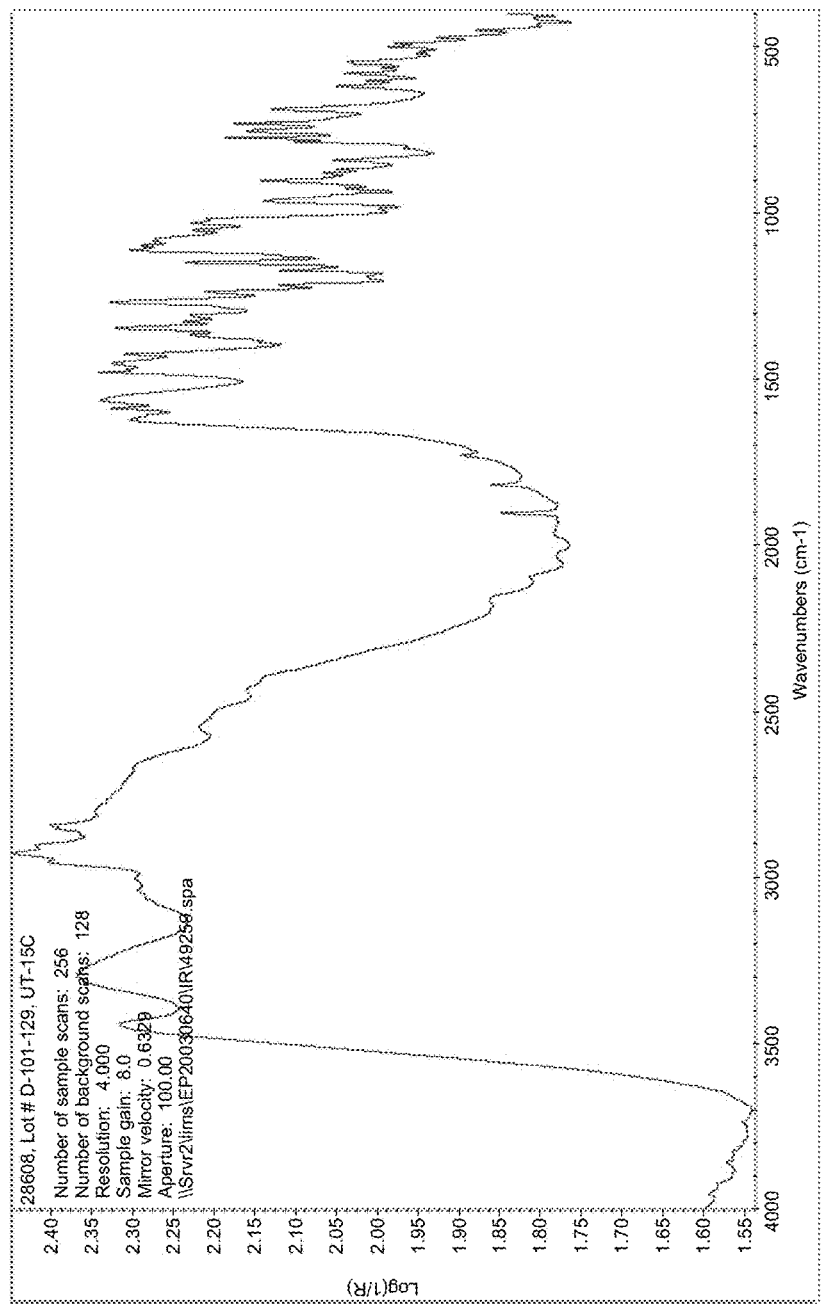
FIG. 16 shows an IR spectrum of the polymorph Form A.
Figure 17:
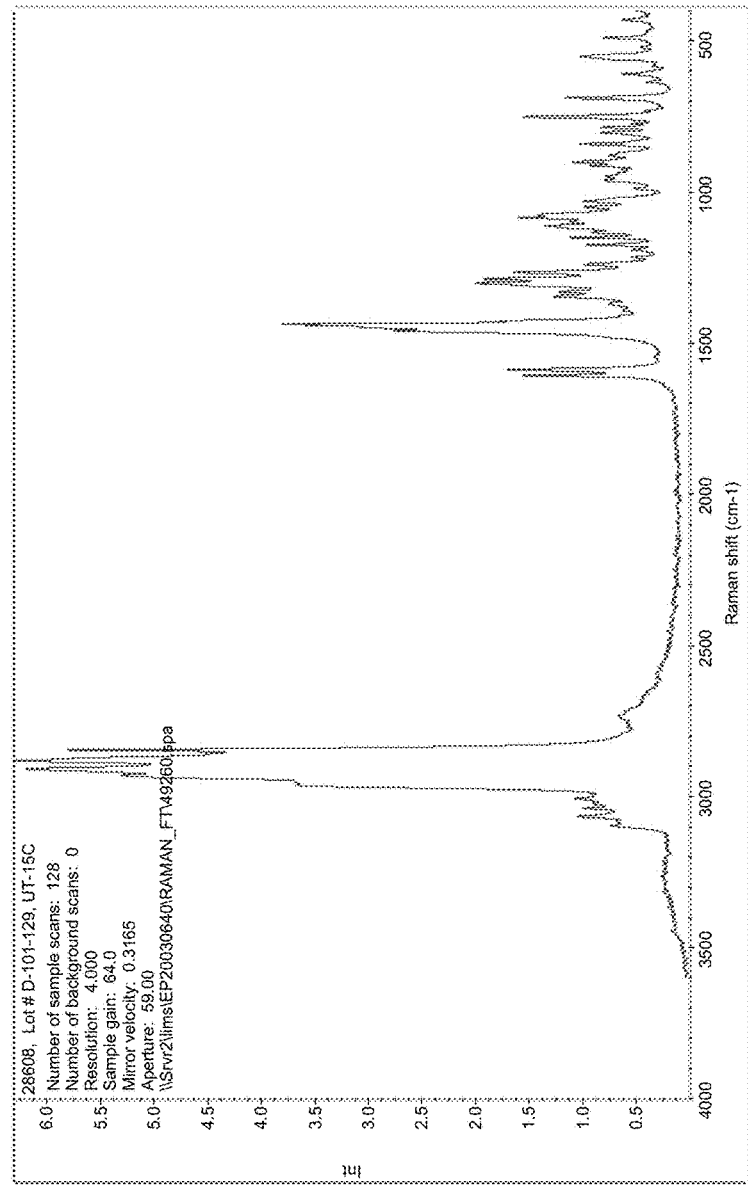
FIG. 17 shows a Raman spectrum of the polymorph Form A.
Figure 18:
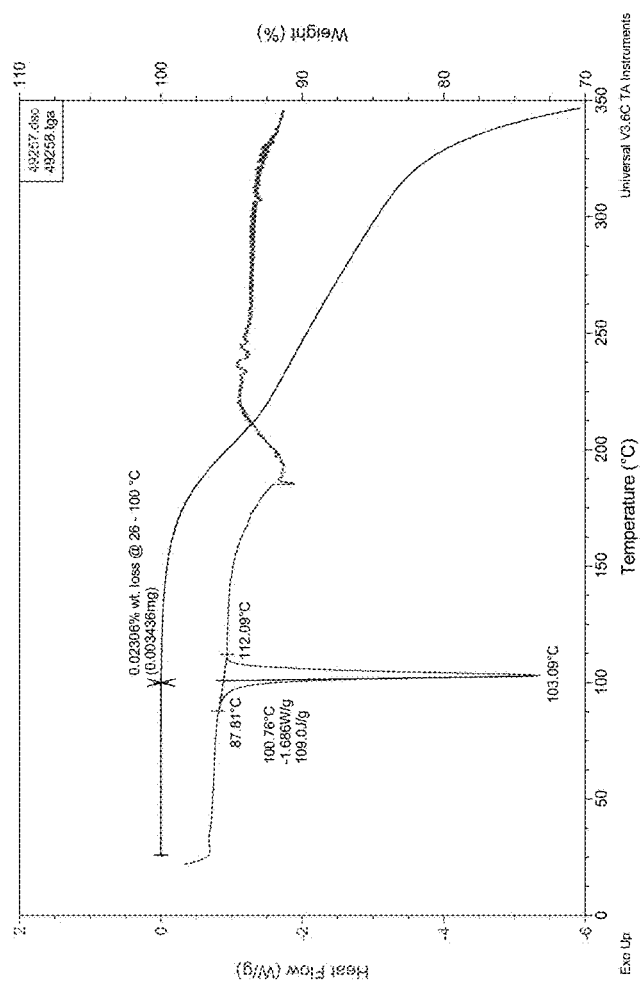
FIG. 18 shows thermal data of the polymorph Form A.
Figure 19:
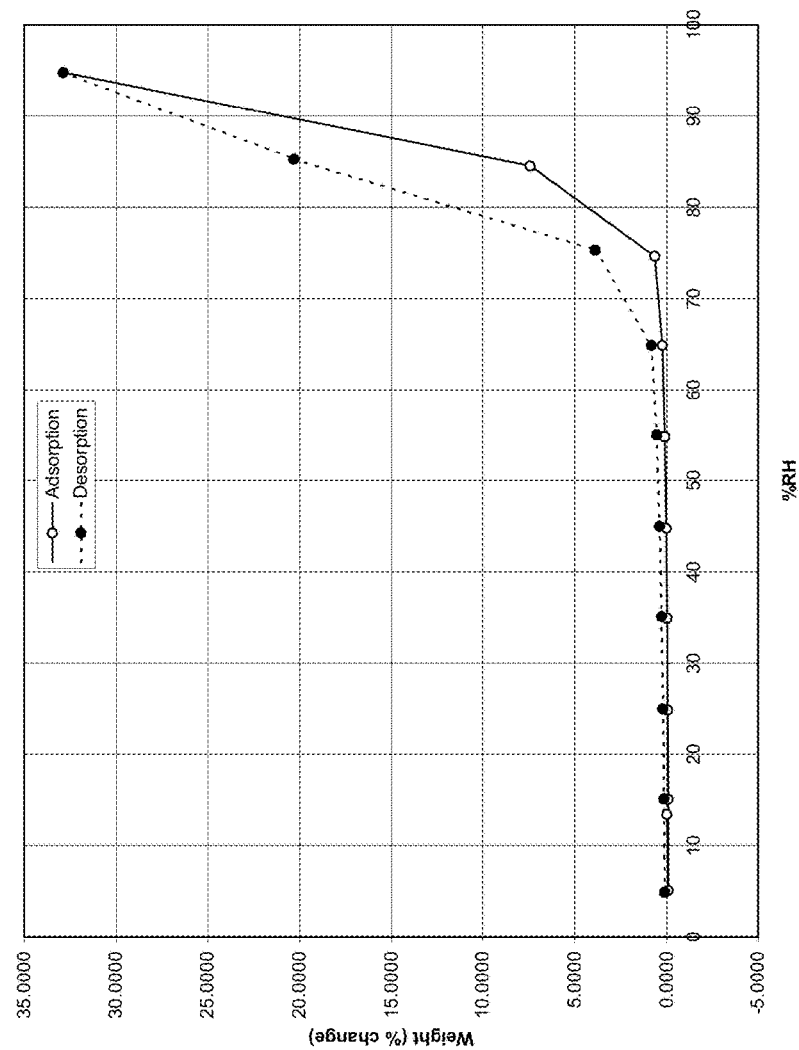
FIG. 19 shows moisture sorption data of the polymorph Form A.

The initial material synthesized (termed Form A) was characterized using X-ray powder diffraction (XRPD), differential scanning calorimetry (DSC), thermogravimetry (TG), hot stage microscopy, infrared (IR) and Raman spectroscopy, and moisture sorption. Representative XRPD of Form A is shown in FIG. 15. The IR and Raman spectra for Form A are shown in FIGS. 16 and 17, respectively. The thermal data for Form A are shown in FIG. 18. The DSC thermogram shows an endotherm at 103° C. that is consistent with melting (from hot stage microscopy). The sample was observed to recrystallize to needles on cooling from the melt. The TG data shows no measurable weight loss up to 100° C., indicating that the material is not solvated. The moisture sorption data are shown graphically in FIG. 19. Form A material shows significant weight gain (>33%) during the course of the experiment (beginning between 65 to 75% RH), indicating that the material is hygroscopic. In addition, hygroscopicity of treprostinil diethanolamine was evaluated in humidity chambers at approximately 52% RH and 68% RH. The materials were observed to gain 4.9% and 28% weight after 23 days in the ~52% RH and ~68% RH chambers, respectively.

Based on the above characterization data, Form A is a crystalline, anhydrous material which is hygroscopic and melts at 103° C.

Form B

Figure 20:
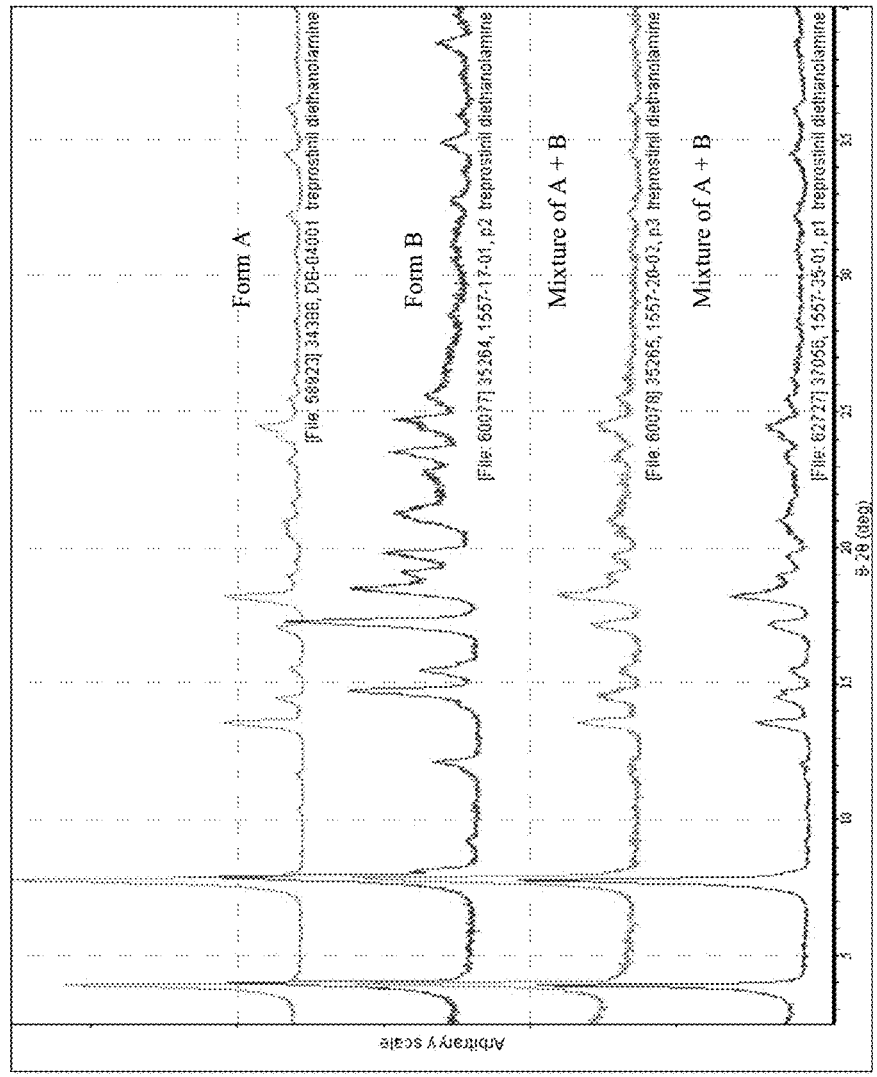
FIG. 20 shows an X ray powder diffraction spectrum of the polymorph Form B.

Treprostinil diethanolamine Form B was made from heated slurries (50° C.) of Form A in 1,4 dioxane and toluene, as shown in Table 16. Material isolated from 1,4-dioxane was used to fully characterize Form B. A representative XRPD pattern of Form B is shown in FIG. 20. Form A and Form B XRPD patterns are similar, however, significant differences are observed in the range of approximately 12-17°2θ (FIG. 20).

Figure 21:
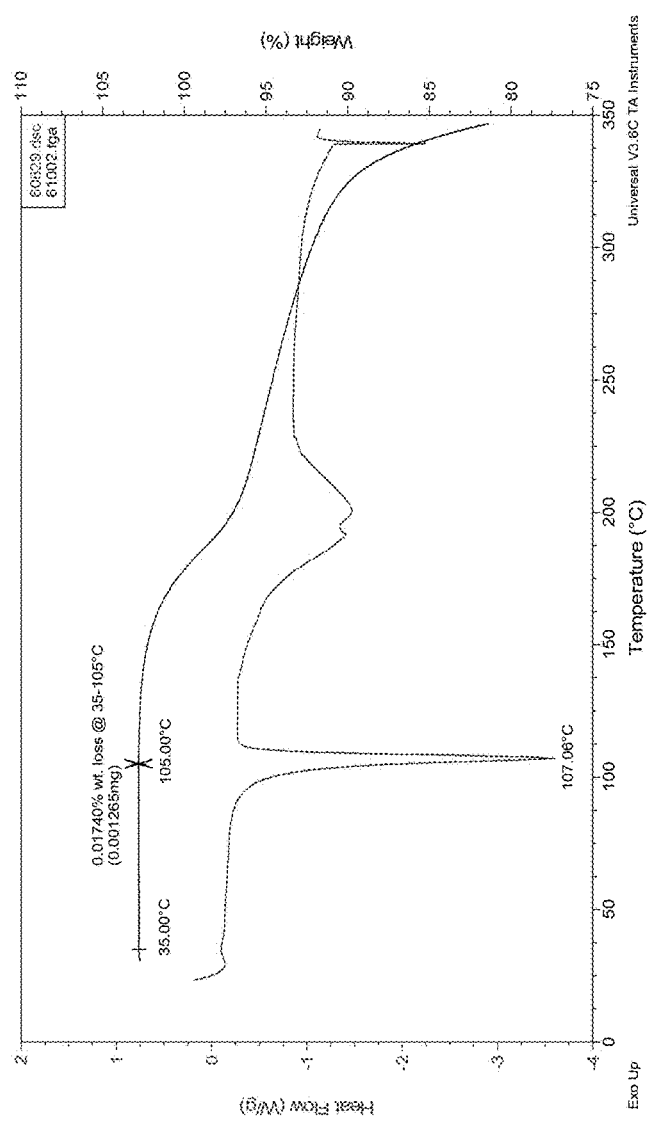
FIG. 21 shows thermal data of the polymorph Form B.

The thermal data for Form B are shown in FIG. 21. The DSC thermogram (Sample ID 1557-17-01) shows a single endotherm at 107° C. that is consistent with a melting event (as determined by hotstage microscopy). The TG shows minimal weight loss up to 100° C.

Figure 22:
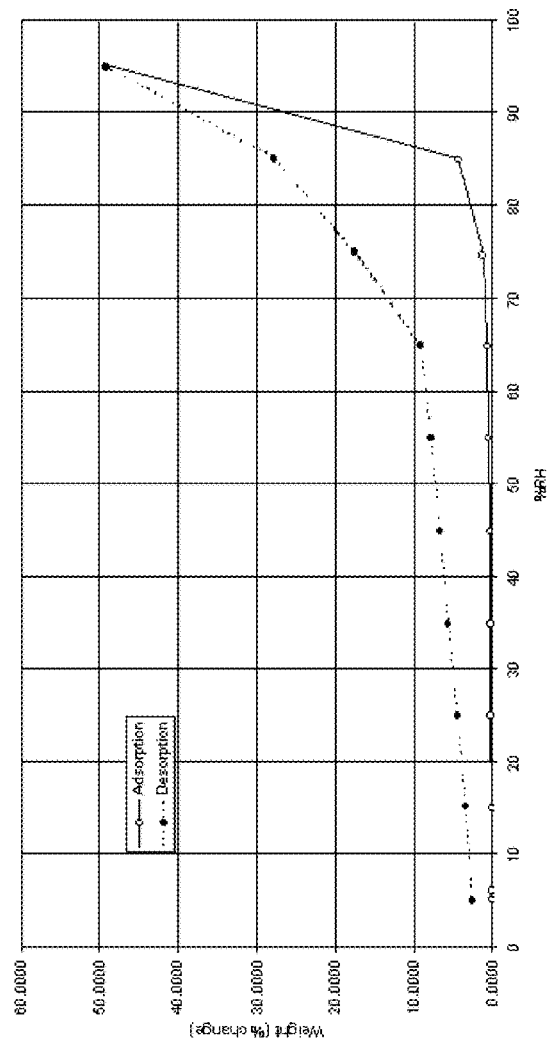
FIG. 22 shows moisture sorption data of the polymorph Form B.

The moisture sorption/desorption data for Form B are shown in FIG. 22. There is minimal weight loss at 5% RH and the material absorbs approximately 49% water at 95% RH. Upon desorption from 95% down to 5% RH, the sample loses approximately 47%.

Form A and Form B can easily be detected in the DSC curve. Based on the above characterization data, Form B appears to be a crystalline material which melts at 107° C.

Thermodynamic Properties:

Inter-conversion experiments were carried out in order to determine the thermodynamically most stable form at various temperatures. These studies were performed in two different solvents, using Forms A and B material, and the data are summarized in Table 17. Experiments in isopropanol exhibit full conversion to Form B at ambient, 15° C., and 30° C. after 7 days, 11 days, and 1 day, respectively. Experiments in tetrahydrofuran also exhibit conversion to Form B at ambient, 15° C., and 30° C. conditions. Full conversion was obtained after 11 days at 15° C., and 1 day at 30° C. At ambient conditions, however, a minor amount of Form A remained after 7 days based on XRPD data obtained. Full conversion would likely occur upon extended slurry time. Based on these slurry inter-conversion experiments, Form B appears to be the most thermodynamically stable form. Form A and Form B appear to be related monotropically with Form B being more thermodynamically stable.

TABLE 17

Interconversion Studies of Treprostinil Diethanolamine

| Sample No. | Forms | Solvent | Experiment/ Starting Materials | Temperature | Time |
|---|---|---|---|---|---|
| 1557-22-01 | A vs. B | isopropanol | solid mixture # 1557-20-01[a] | ambient | 7 days |
| 1557-47-02 | A vs. B | | solid mixture # 1557-35-01[d] | 15° C. | 11 days |
| 1557-33-02 | A vs. B | | solid mixture # 1557-35-01[d] | 30° C. | 1 day |
| 1557-21-02[e] | A vs. B | | solid mixture # 1557-20-01[b] | 50° C. | — |
| 1557-20-03 | A vs. B | tetrahydrofuran | solid mixture # 1557-20-01[c] | ambient | 7 days |
| 1557-47-01 | A vs. B | | solid mixture # 1557-35-01[d] | 15° C. | 11 days |
| 1557-33-01 | A vs. B | | solid mixture # 1557-35-01[d] | 30° C. | 1 day |
| 1557-21-01[e] | A vs. B | | solid mixture # 1557-20-01[c] | 50° C. | — |

[a]saturated solution Sample ID 1557-21-03
[b]saturated solution Sample ID 1519-96-03
[c]saturated solution Sample ID 1519-96-02
[d]saturated solution prepared just prior to addition of solids
[e]samples not analyzed as solubility (at 50° C.) of treprostinil diethanolamine was very high and solutions became discolored.

All references disclosed herein are specifically incorporated by reference thereto.

While preferred embodiments have been illustrated and described, it should be understood that changes and modifications can be made therein in accordance with ordinary skill in the art without departing from the invention in its broader aspects as defined herein.

What is claimed is:

1. A compound having structure I:

wherein $R^1$ is independently selected from the group consisting of H, and groups wherein $OR^1$ are substituted or unsubstituted glycolamide esters, and wherein $R^2$ and $R^3$ may be the same or different and are independently selected from the group consisting of H, phosphate and groups wherein $OR^2$ and $OR^3$ form esters of amino acids, with the proviso that all of $R^1$, $R^2$, and $R^3$ are not H;

an enantiomer of the compound; or a pharmaceutically acceptable salt of the compound.

2. The compound of claim 1, wherein $R^1$ is H.

3. The compound of claim 2, wherein at least one of $R^2$ and $R^3$ is phosphate.

4. The compound of claim 3, wherein each of $R^2$ and $R^3$ is phosphate.

5. The compound of claim 2, wherein $R^2$ is H and $R^3$ is phosphate.

6. The compound of claim 2, wherein $R^2$ is phosphate and $R^3$ is H.

7. The compound of claim 2, wherein at least one of $OR^2$ and $OR^3$ forms an ester of an amino acid.

8. The compound of claim 7, wherein $OR^2$ forms an ester of an amino acid and $R^3$ is H.

9. The compound of claim 7, wherein $R^2$ is H and $OR^3$ forms an ester of an amino acid.

10. A pharmaceutical composition comprising:
    (A) a compound having structure I:

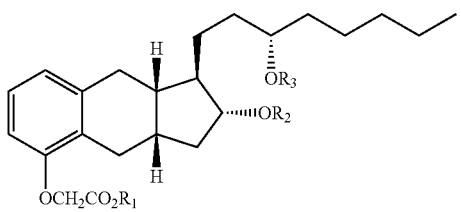

wherein $R^1$ is independently selected from the group consisting of H, substituted and unsubstituted benzyl groups, and groups wherein $OR^1$ are substituted or unsubstituted glycolamide esters, and wherein $R^2$ and $R^3$ may be the same or different and are independently selected from the group consisting of H, phosphate and groups wherein $OR^2$ and $OR^3$ form esters of amino acids, with the proviso that all of $R^1$, $R^2$, and $R^3$ are not H;

an enantiomer of the compound; or a pharmaceutically acceptable salt of the compound; and (B) a pharmaceutically acceptable excipient.

11. The composition of claim 10, wherein $R^1$ is H.

12. The composition of claim 11, wherein at least one of $R^2$ and $R^3$ is phosphate.

13. The composition of claim 12, wherein each of $R^2$ and $R^3$ is phosphate.

14. The composition of claim 11, wherein $R^2$ is H and $R^3$ is phosphate.

15. The composition of claim 11, wherein $R^2$ is phosphate and $R^3$ is H.

16. The composition of claim 11, wherein at least one of $OR^2$ and $OR^3$ forms an ester of an amino acid.

17. The compound of claim 16, wherein $OR^2$ forms an ester of an amino acid and $R^3$ is H.

18. The compound of claim 16, wherein $R^2$ is H and $OR^3$ forms an ester of an amino acid.

19. A method of treating pulmonary hypertension in a human subject comprising administering to a subject in need thereof an effective amount of a compound having structure I:

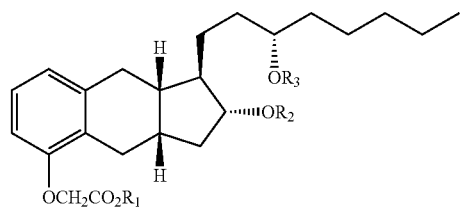

wherein $R^1$ is independently selected from the group consisting of H, substituted or unsubstituted alkyl groups, substituted and unsubstituted benzyl groups, and groups wherein $OR^1$ are substituted or unsubstituted glycolamide esters, and wherein $R^2$ and $R^3$ may be the same or different and are independently selected from the group consisting of H, phosphate and groups wherein $OR^2$ and $OR^3$ form esters of amino acids, with the proviso that all of $R^1$, $R^2$ and $R^3$ are not H;

an enantiomer of the compound; or a pharmaceutically acceptable salt of the compound.

20. The method of claim 19, wherein $R^1$ is H.

21. The method of claim 20, wherein at least one of $R^2$ and $R^3$ is phosphate.

22. The method of claim 21, wherein each of $R^2$ and $R^3$ is phosphate.

23. The method of claim 20, wherein $R^2$ is H and $R^3$ is phosphate.

24. The method of claim 20, wherein $R^2$ is phosphate and $R^3$ is H.

25. The method of claim 20, wherein at least one of $OR^2$ and $OR^3$ forms an ester of an amino acid.

26. The method of claim 25, wherein $OR^2$ forms an ester of an amino acid and $R^3$ is H.

27. The method of claim 25, wherein $R^2$ is H and $OR^3$ forms an ester of an amino acid.

28. The method of claim 19, wherein said administering is performed orally.

29. The method of claim 19, wherein said administering is performed subcutaneously.

30. The method of claim 19, wherein both $R^2$ and $R^3$ are H.

31. The method of claim 30, wherein $R^1$ is a substituted or unsubstituted alkyl group.

32. The method of claim 31, wherein $R^1$ is a substituted alkyl group.

33. The method of claim 32, wherein $R^1$ is an alkyl group in which one or more bonds to one or more carbon or one or more hydrogen atoms is replaced by a bond to an oxygen atom in a carbonyl, carboxyl or ester group.

34. The method of claim 33, wherein $R^1$ is an alkyl group in which one or more bonds to one or more carbon or one or more hydrogen atoms is replaced by a bond to an oxygen atom in a carboxyl group.

* * * * *